United States Patent
Auvin et al.

(10) Patent No.: US 9,682,941 B2
(45) Date of Patent: Jun. 20, 2017

(54) SUBSTITUTED BIPHENYL ANALOGUES AS DUAL INHIBITORS OF AROMATASE AND SULFATASE

(71) Applicant: ESTRYX PHARMA LIMITED, Combe, Witney, Oxfordshire (GB)

(72) Inventors: Serge Auvin, Palaiseau (FR); Olivier Lavergne, Palaiseau (FR); Qi Chao, San Diego, CA (US); Yufeng Chen, Zhejiang (CN)

(73) Assignee: ESTRYX PHARMA LIMITED, Combe, Witney, Oxfordshire (GB)

( * ) Notice: Subject to any disclaimer, the term of this patent is extended or adjusted under 35 U.S.C. 154(b) by 0 days.

(21) Appl. No.: 15/104,884

(22) PCT Filed: Dec. 31, 2013

(86) PCT No.: PCT/CN2013/091085
§ 371 (c)(1),
(2) Date: Jun. 15, 2016

(87) PCT Pub. No.: WO2015/100609
PCT Pub. Date: Jul. 9, 2015

(65) Prior Publication Data
US 2017/0001964 A1    Jan. 5, 2017

(51) Int. Cl.
| | | |
|---|---|---|
| *C07D 401/12* | (2006.01) | |
| *C07D 235/16* | (2006.01) | |
| *A61K 31/4184* | (2006.01) | |
| *A61K 31/4188* | (2006.01) | |
| *A61K 31/4192* | (2006.01) | |
| *A61K 31/444* | (2006.01) | |
| *C07D 249/18* | (2006.01) | |
| *C07D 235/06* | (2006.01) | |
| *C07D 401/06* | (2006.01) | |
| *C07D 235/22* | (2006.01) | |
| *C07D 403/06* | (2006.01) | |
| *C07D 471/04* | (2006.01) | |
| *C07D 403/12* | (2006.01) | |

(52) U.S. Cl.
CPC ........ *C07D 235/16* (2013.01); *A61K 31/4184* (2013.01); *A61K 31/4188* (2013.01); *A61K 31/4192* (2013.01); *A61K 31/444* (2013.01); *C07D 235/06* (2013.01); *C07D 235/22* (2013.01); *C07D 249/18* (2013.01); *C07D 401/06* (2013.01); *C07D 401/12* (2013.01); *C07D 403/06* (2013.01); *C07D 403/12* (2013.01); *C07D 471/04* (2013.01)

(58) Field of Classification Search
CPC .. C07D 235/06; C07D 235/16; C07D 235/22; C07D 249/18; C07D 401/06; C07D 403/06; C07D 403/12; C07D 471/04; A61K 31/4184; A61K 31/4188; A61K 31/4192; A61K 31/444

USPC ..... 544/332, 333, 405; 546/117, 118, 273.4; 548/257, 309.7; 514/255.05, 256, 300, 514/303, 338, 359, 394
See application file for complete search history.

(56) References Cited

FOREIGN PATENT DOCUMENTS

| CN | 102596919 A | 7/2012 |
|---|---|---|
| WO | WO 2005/118560 A1 | 12/2005 |
| WO | WO 2007/068905 A1 | 6/2007 |
| WO | WO 2011/023989 A1 | 3/2011 |

OTHER PUBLICATIONS

G.A. Olah et al., "Fluorine-containing reagents in organic synthesis," Journal Fluorine Chemistry 1986, vol. 33, issue 1-4, pp. 377-396.
International Search Report and Written Opinion issued in International Patent Application No. PCT/CN2013/091085 mailed Sep. 29, 2014.
L.W. Lawrence Woo, et al., "Development of steroid sulfatase inhibitors," Molecular and Cellular Endocrinology, 2011, vol. 340, issue 2, pp. 175-185.
Peter G.M. Wuts et al., "Greene's Protective Groups in Organic Synthesis", Wiley, 2007, pp. 1-27.
Philip L. Gould, "Salt selection for basic drugs", International Journal Pharmaceutics, 1986, vol. 33, issues 1-3, pp. 201-217.

*Primary Examiner* — Deepak Rao
(74) *Attorney, Agent, or Firm* — Arent Fox LLP

(57) ABSTRACT

The present invention relates to new biphenyl derivatives of formula

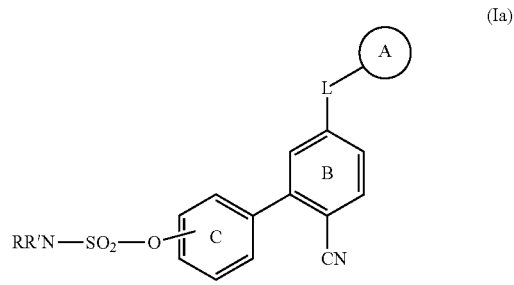

(Ia)

These compounds acting as aromatase and sulfatase inhibitors, they are particularly useful for treating pathological conditions or diseases in which aromatase and sulfatase are involved. Moreover, the present invention provides processes for the preparation of these compounds. The invention also relates to pharmaceutical compositions containing said products and their use for the preparation of a medicament, in particular for the treatment of diseases characterized by aromatase and sulfatase activity such as hormone-dependent cancers.

16 Claims, No Drawings

SUBSTITUTED BIPHENYL ANALOGUES AS DUAL INHIBITORS OF AROMATASE AND SULFATASE

CROSS REFERENCE TO RELATED APPLICATION

This application is a 35 U.S.C. 371 National Phase of PCT Application No. PCT/CN2013/091085 filed Dec. 31, 2013, the disclosure of this prior application is hereby incorporated in their entirety by reference.

The present invention relates to new biphenyl derivatives. These compounds acting as aromatase and sulfatase inhibitors, they are particularly useful for treating pathological conditions or diseases in which aromatase and sulfatase are involved. Moreover, the present invention provides processes for the preparation of these compounds. The invention also relates to pharmaceutical compositions containing said products and their use for the preparation of a medicament, in particular for the treatment of diseases characterized by aromatase and sulfatase activity such as hormone-dependent cancers.

Development of hormone dependent cancers is highly dependent on estrogens and androgens production. Different cancer types are included in this category, mostly breast, endometrial and prostate cancers. Steroid sulfatase and aromatase have been identified as key enzymes involved in estrogens and androgens production. As such, they are amenable to targeting as oncology targets to inhibit hormone dependent cancer growth. Aromatase inhibition is a well-established therapeutic strategy and is used routinely in the clinic for the treatment of ER+ breast cancer. Aromatase inhibitors block the conversion of androstenedione to estrone (E1). Steroid sulfatase is the enzyme which produces E1 from E1S and DHEA from DHEAS. Inhibition of this enzyme seems thus promising to block E1 production. Sulfatase inhibitors have been described in the literature (Molecular and Cellular Endocrinology (2011), 340(2), 175-185). Combining the 2 approaches with the administration of 2 different compounds although interesting to fully block E1 production, could bring some therapeutic issues. Drug-drug interactions and emergence of resistance to one or the other agent is one of such issues. Dual inhibitors consisting in one compound containing the 2 activities, is an alternative. The applicant identified compounds containing potent both sulfatase and aromatase inhibition capacities. Moreover, they show a very low CYP inhibition property.

A subject of the present invention is therefore a compound of the formula (Ia)

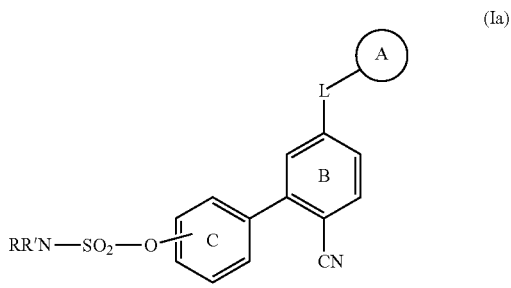

wherein

A represents an aromatic bicyclic ring of up to 10 ring members, containing at least two nitrogen atoms as ring member, and being optionally substituted by one or more substituents selected from halo, alkyl and haloalkyl;

B represents an aromatic monocyclic ring of 6 ring members, containing optionally nitrogen atoms as ring member;

C represents an aromatic monocyclic ring of 6 ring members, containing optionally nitrogen atoms as ring member and optionally substituted by an alkyl-thiol, the radical RR'NSO$_2$—O— being in meta or para position;

R and R' represent, independently, hydrogen or alkyl;

L is a linker selected from —CH$_2$—, —NH—, —N(alkyl)- and —N(cycloalkyl-methyl)-; or any pharmaceutically acceptable salt thereof.

In the definitions given above, the expression halo by itself or as part of another substitutent represents the fluoro, chloro, bromo or iodo radical, preferably chloro, fluoro or bromo, and more preferably fluoro. The expression alkyl by itself or as part of another substituent means a linear or branched alkyl radical of one to six carbon atoms, i.e. a $C_1$-$C_6$ alkyl. A $C_1$-$C_6$ alkyl includes methyl, ethyl, n-propyl, i-propyl, butyl and its isomers (e.g. n-butyl, i-butyl and t-butyl); pentyl and its isomers, hexyl and its isomers. The expression haloalkyl means an alkyl radical as defined above substituted by at least one halo as defined above such as for instance, trifluoromethyl or difluoroethyl.

The term "cycloalkyl" by itself or as part of another substituent is a cyclic alkyl group, saturated, and comprising from three or more carbon atoms in the ring and generally, according to the present invention comprise from 3 to 6 atoms such as, for instance, cyclopropyl, cyclobutyl, cyclopentyl, cyclohexyl. The expression alkyl-thiol represents a radical wherein the alkyl is as defined above such as methyl-thiol (CH$_3$—S—), ethyl-thiol. An aromatic monocyclic ring is a ring containing 5 to 6 ring members. Such ring containing nitrogen atoms may be selected from pyrrole, imidazole, pyrazole, pyridine, pyrazine, pyrimidine, pyridazine. An aromatic bicyclic ring is a ring containing 5 to 10 ring members and represents 2 fused cycles. Such ring containing at least 2 nitrogen atom may be selected from indazole, purine, phtalazine, naphtyridine, quinoxaline, quinazoline, clinnoline and ptéridine. In case the aromatic ring, mono- or bicyclic, contains nitrogen atoms, it does not contain any other heteroatom such as oxygen or sulfur. Boc is tert-butyl carbamate.

In a preferred embodiment, the radical RR'N—SO$_2$—O— of the C ring is at the meta position. In a preferred embodiment, RR'N—SO$_2$—O— of the C ring is at the meta position and R and R' represent, independently, hydrogen or methyl. In an other preferred embodiment, RR'N—SO$_2$—O— of the C ring is at the meta position and represents MeHN—SO$_2$—O— or H$_2$N—SO$_2$—O—.

In a preferred embodiment, the radical RR'N—SO$_2$—O— of the C ring is at the para position. The compounds of formula (Ia) wherein the radical RR'N—SO$_2$—O— of the C ring is at the para position are called compounds of formula (Ib).

A subject of the present invention is therefore a compound of the formula (Ia)

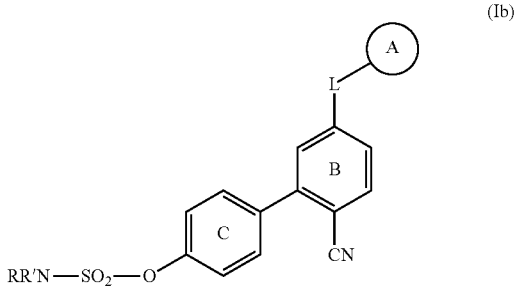

wherein

A represents an aromatic bicyclic ring of up to 10 ring members, containing at least two nitrogen atoms as ring member, and being optionally substituted by one or more substituents selected from halo, alkyl and haloalkyl;

B represents an aromatic monocyclic ring of 6 ring members, containing optionally nitrogen atoms as ring member;

C represents an aromatic monocyclic ring of 6 ring members, containing optionally nitrogen atoms as ring member and optionally substituted by an alkyl-thiol, the radical RR'SO$_2$—O— being in meta or para position;

R and R' represent independently hydrogen and alkyl;

L is a linker selected from —CH$_2$—, —NH—, —N(alkyl)- and —N(cycloalkyl-methyl)-; or any pharmaceutically acceptable salt thereof.

In a preferred embodiment, the present invention relates to compounds of formula (Ib) wherein R and R' represent, independently, hydrogen or methyl. In an other preferred embodiment, the present invention relates to compounds of formula (Ib) wherein RR'N—SO$_2$—O— represents MeHN—SO$_2$—O— or H$_2$N—SO$_2$—O—.

The compounds of formula (Ia) wherein the radical RR'N—SO$_2$—O— of the C ring is at the para position and R and R' represent hydrogen, are called compounds of formula (I).

In another preferred embodiment, a subject of the invention is a compound of general formula (I)

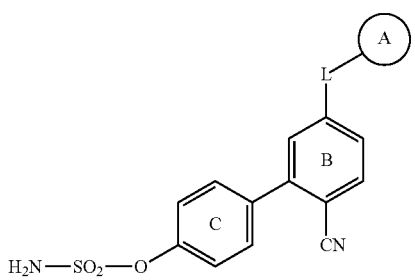

wherein

A represents an aromatic bicyclic ring of up to 10 ring members, containing at least two nitrogen atoms as ring member, and being optionally substituted by one or more substituents selected from halo;

B represents an aromatic monocyclic ring, containing optionally nitrogen atoms as ring member;

C represents an aromatic monocyclic ring containing optionally nitrogen atoms as ring member;

L is a linker selected from —CH$_2$—, —NH— or —N(Me)-; or any pharmaceutically acceptable salt thereof.

Preferably, the invention relates to compounds of formula I as defined above, wherein L is a linker selected from —CH$_2$— and —NH—; or any pharmaceutically acceptable salt thereof. More preferably, L is —CH$_2$—. In another preferred embodiment, L is —NH—.

Preferably, the invention relates to compounds of formula (Ia), (Ib) and (I) in particular, as defined above, wherein A represents an aromatic bicyclic ring of up to 9 ring members, containing at least two nitrogen atoms as ring member, and being optionally substituted by one or more substituents selected from halo; or any pharmaceutically acceptable salt thereof.

Preferably, the invention relates to compound of the formula (Ia), (Ib) and (I) in particular, as defined above, wherein A represents an aromatic bicyclic ring of 9 ring members, containing at least two nitrogen atoms as ring member, and being optionally substituted by one or more substituents selected from halo; or any pharmaceutically acceptable salt thereof.

In a preferred embodiment, A represents an aromatic bicyclic ring of 9 ring members, containing from two to four nitrogen atoms as ring member, and being optionally substituted by one or more substituents selected from halo.

In another preferred embodiment, A represents an aromatic bicyclic ring of 9 ring members, containing at least two nitrogen atoms as ring member, and being optionally substituted by one or more substituents selected from halo, the bicyclic ring being the fusion of a ring of 5 ring members and a ring of 6 ring members.

According to the present invention, a bicyclic ring being the fusion of a ring of 5 ring members and a ring of 6 ring members may illustrated by the following ring squeleton

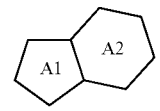

Preferably, the present invention relates to a compound of the formula (Ia), (Ib) and (I) in particular, as defined above, wherein A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members; or any pharmaceutically acceptable salt thereof.

In another preferred embodiment, A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members, the ring of 5 ring members containing at least 2 nitrogen atoms.

More preferably, A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members, the ring of 5 ring members being linked to the linker L.

Preferably, the present invention relates to a compound of the formula (Ia), (Ib) and (I) in particular, as defined above, wherein A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members, the ring of 5 ring members containing at least 2 nitrogen atoms and being linked to the linker L; or any pharmaceutically acceptable salt thereof.

In another preferred embodiment, A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members, the ring of 5 ring members containing at least 2 nitrogen atoms and being linked to the linker L by a nitrogen ring member.

In another preferred embodiment, A represents an aromatic bicyclic ring selected from

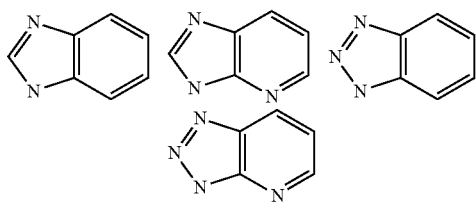

optionally substituted by one or more substituents selected from halo.

Preferably, the present invention relates to a compound of the formula (Ia), (Ib) and (I) in particular, as above defined, wherein A represents an aromatic bicyclic ring selected from

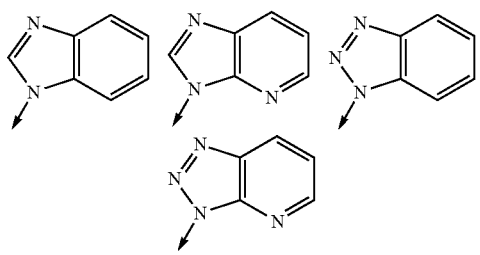

and being optionally substituted by one or more substituents selected from halo; or any pharmaceutically acceptable salt thereof.

In a more preferred embodiment, A represents an unsubstituted aromatic bicyclic ring of formula

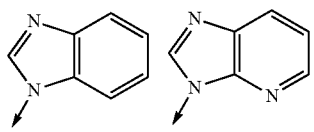

More preferably, the present invention relates a compound of the formula (Ia), (Ib) and (I) in particular, as defined above, wherein A represents a unsubstituted ring; or any pharmaceutically acceptable salt thereof.

In another more preferred embodiment, the present invention relates to a compound of the formula (Ia), (Ib) and (I) in particular, as defined above, wherein A represents a ring substituted by one or two fluoro radicals; or any pharmaceutically acceptable salt thereof.

In another preferred embodiment, the present invention relates to a compound of the formula (Ia), (Ib) and (I) in particular, as defined above, wherein the B ring contains no nitrogen atom as ring member; or any pharmaceutically acceptable salt thereof.

In another preferred embodiment, the present invention relates to a compound of the formula (Ia), (Ib) and (I) in particular, as defined above, wherein the B ring contains at least one nitrogen atom as ring member; or any pharmaceutically acceptable salt thereof.

In a more preferred embodiment, the invention relates to a compound of the formula (Ia), (Ib) and (I) in particular, as defined above, wherein the B ring contains from one or two nitrogen atoms as ring member; or any pharmaceutically acceptable salt thereof.

In another preferred embodiment, B represents an aromatic ring containing one nitrogen atom as ring member.

In another preferred embodiment, B represents an aromatic ring containing two nitrogen atoms as ring member.

In another more preferred embodiment, B represents an aromatic monocyclic ring selected from

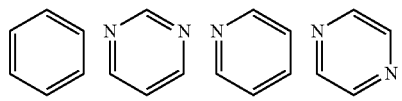

In another more preferred embodiment, the invention relates to a compound of the formula (Ia), (Ib) and (I) in particular, as defined above, wherein B represents an aromatic monocyclic ring selected from

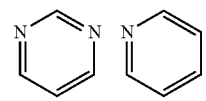

or any pharmaceutically acceptable salt thereof.

In another more preferred embodiment, B represents an aromatic monocyclic ring selected from

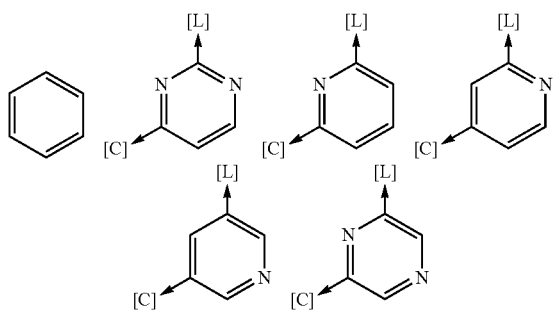

and more particularly an aromatic monocyclic ring selected from

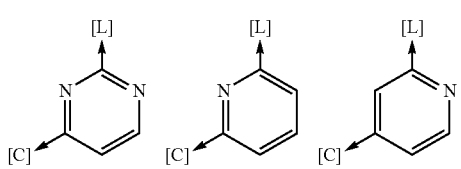

-continued

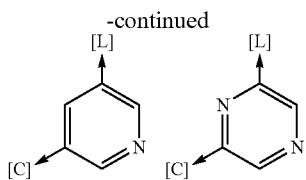

In another preferred embodiment, the invention relates to a compound of the formula (Ia), (Ib) and (I) in particular, as defined above, wherein the C ring contains no nitrogen atom as ring member; or any pharmaceutically acceptable salt thereof.

In another preferred embodiment, the invention relates to a compound of the formula (Ia), (Ib) and (I) in particular, as defined above, wherein the C ring contains at least one nitrogen atom as ring member; or any pharmaceutically acceptable salt thereof. In a more preferred embodiment, C represents an aromatic monocyclic ring of 6 ring members containing from one or two nitrogen atoms as ring member.

In another preferred embodiment, the invention relates to a compound of the formula (Ia), (Ib) and (I) in particular, as defined above, wherein C represents an aromatic monocyclic ring containing one nitrogen atoms as ring member; or any pharmaceutically acceptable salt thereof.

In another preferred embodiment, C represents an aromatic monocyclic ring selected from

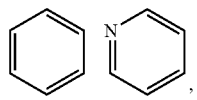

and more preferably, C represents an aromatic monocyclic ring selected from

In another more preferred embodiment C represents an aromatic monocyclic ring selected from

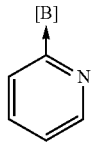

In another preferred embodiment, the invention relates to a compound of the formula (Ia), (Ib) and (I) in particular, as defined above, wherein the B and C rings contain no nitrogen atom as ring member; or any pharmaceutically acceptable salt thereof.

In another preferred embodiment, the invention relates to a compound of the formula (I), as defined above, wherein the B and C rings contain no nitrogen atom as ring member; or any pharmaceutically acceptable salt thereof.

In another preferred embodiment, the invention relates to a compound of the formula (I) as above defined, wherein at least one of the B and C rings contains at least one nitrogen atom as ring member; or any pharmaceutically acceptable salt thereof.

In another preferred embodiment, the B ring contains at least one nitrogen atom as ring member and the C ring contains no nitrogen atom.

In a preferred embodiment, the present invention relates to a compound of the formula (Ic) corresponding to compound of formula (I) as above defined, wherein
A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members, the ring of 5 ring members being linked to the linker L;
B ring contains up to two nitrogen atom as ring member;
C ring contains up to one nitrogen atom as ring member and is optionally substituted by alkylthiol; and
L is a linker selected from —CH$_2$—, —NH— and —N(CH$_3$)— when A contains two nitrogen atoms, or L is a linker selected from —CH$_2$— and —NH— when A contains three or four nitrogens; or any pharmaceutically acceptable salt thereof.

In another preferred embodiment, the present invention relates to a compound of the formula (Ic) as above defined, wherein C ring contains no nitrogen atom as ring member. In another preferred embodiment, the present invention relates to a compound of the formula (Ic) as above defined, wherein C ring contains no nitrogen atom as ring member and is optionally substituted by alkylthiol.

In a preferred embodiment, the present invention relates to a compound of the formula (Ic) as above defined, wherein C ring contains one nitrogen atom as ring member. In another preferred embodiment, the present invention relates to a compound of the formula (Ic) as above defined, wherein
either A contains two nitrogens and is optionally substituted by one or more substituents selected from halo, and L is a linker selected from —CH$_2$—, —NH— and —N(CH$_3$)—;
or A contains three to four nitrogens and L is a linker selected from —CH$_2$— and —NH—; and
B and C rings contain no nitrogen atom as ring member and C is substituted by alkyl-thiol; or any pharmaceutically acceptable salt thereof.

In another preferred embodiment, the present invention relates to a compound of the formula (Ic) as above defined, wherein at least one of B and C rings contains at least one nitrogen atom as ring member; or any pharmaceutically acceptable salt thereof.

In another preferred embodiment, the present invention relates to a compound of the formula (Ic) as above defined, wherein
A represents an aromatic bicyclic ring of 9 ring members, containing two nitrogen atoms as ring member, and being optionally substituted by one or more substituents selected from halo, the bicyclic ring being the fusion of a ring of 5 ring members and a ring of 6 ring members, the ring of 5 ring members being linked to the linker L;
C represents

optionally substituted by alkylthiol, or

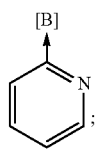

at least one of B and C rings contains at least one nitrogen atom as ring member;
and
either L is a linker selected from —CH$_2$— and —NH— and B represent

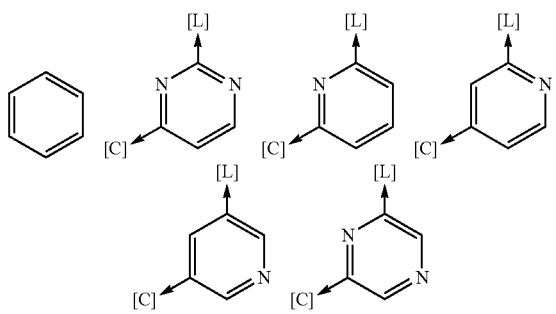

or
L is the linker —N(CH$_3$)— and B represents

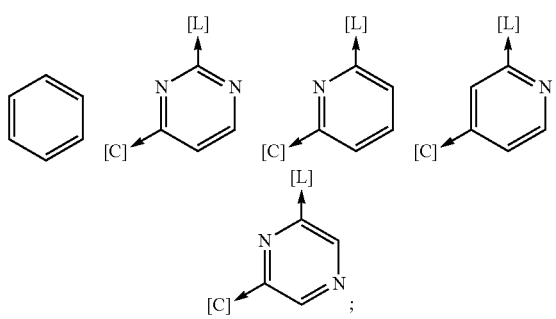

or any pharmaceutically acceptable salt thereof.

In another preferred embodiment, the present invention relates to a compound of the formula (Ic) as above defined, wherein A represents an aromatic bicyclic ring of 9 ring members, containing from three to four nitrogen atoms as ring member, and being optionally substituted by one or more substituents selected from halo, the bicyclic ring being the fusion of a ring of 5 ring members and a ring of 6 ring members, the ring of 5 ring members being linked to the linker L;

C represents

optionally substituted by alkylthiol, or

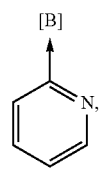

and
at least one of B and C rings contains at least one nitrogen atom as ring member;
and either L is the linker —CH$_2$— and B represent

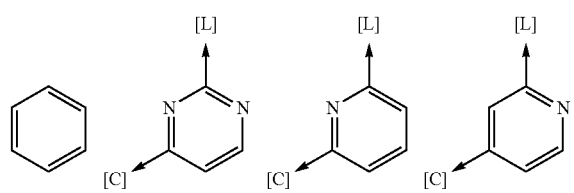

or either L is the linker —NH— and B represent

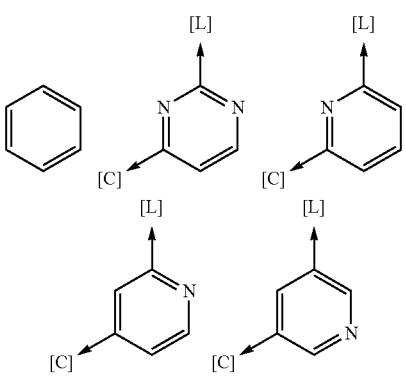

In another preferred embodiment, the present invention relates to a compound of the formula (Ic) as above defined, wherein
A represents

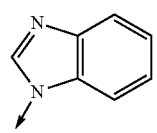

optionally substituted by one or more substituents selected from halo or

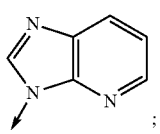

L is a linker selected from —CH$_2$— and —NH—; and
at least one of B and C rings contains at least one nitrogen atom as ring member; or any pharmaceutically acceptable salt thereof.

In another more preferred embodiment, the present invention relates to a compound of the formula (Ic) as above defined, wherein
A represents

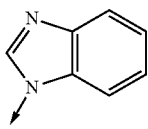

optionally substituted by one or more substituents selected from halo;
L is a linker selected from —CH₂— and —NH—;
B represents

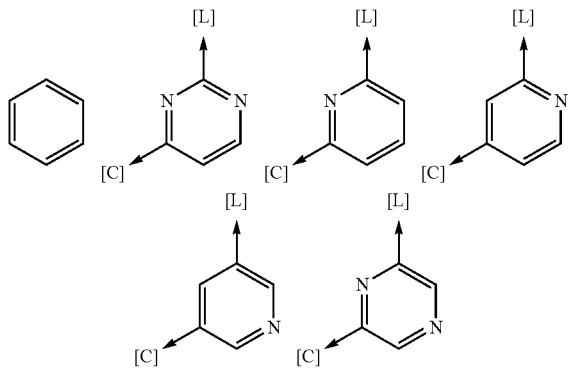

C represents

optionally substituted by alkylthiol, or

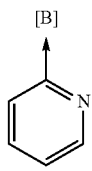

at least one of B and C rings contains at least one nitrogen atom as ring member;
and in a more preferred embodiment,
B represents

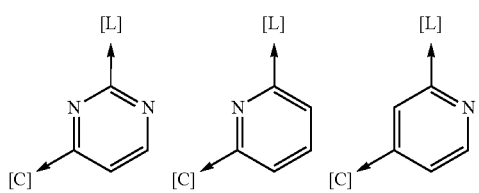

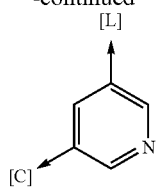

C represents

or any pharmaceutically acceptable salt thereof.
In another more preferred embodiment, the present invention relates to a compound of the formula (Ic) as above defined, wherein
A represents

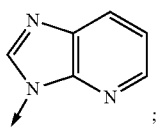

L is the linker —CH₂—:
B represents

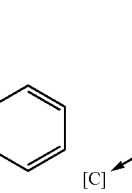 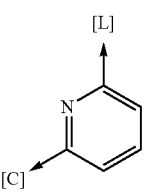 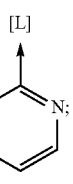

C represents

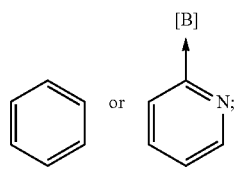

at least one of B and C rings contains at least one nitrogen atom as ring member; or any pharmaceutically acceptable salt thereof.

Preferably, the compound of the present invention is selected from the following compounds:
5'-((1H-Benzo[d]imidazol-1-yl)methyl)-2'-cyano-[1,1'-biphenyl]-4-yl sulfamate;
5'-(1H-Benzo[d]imidazol-1-ylamino)-2'-cyano-[1,1'-biphenyl]-4-yl sulfamate;
2'-Cyano-5'-((2-methyl-1H-benzo[d]imidazol-1-yl)methyl) biphenyl-4-yl sulfamate;
5'-((1H-Benzo[d][1,2,3]triazol-1-yl)methyl)-2'-cyano-[1,1'-biphenyl]-4-yl sulfamate;

5'-((1H-Benzo[d]imidazol-1-yl)(methyl)amino)-2'-cyano-[1,1'-biphenyl]-4-yl sulfamate;
5'-((1H-Benzo[d]imidazol-1-yl)(cyclopropylmethyl)amino)-2'-cyano-[1,1'-biphenyl]-4-yl sulfamate;
2'-Cyano-5'-((2-(trifluoromethyl)-1H-benzo[d]imidazol-1-yl)methyl)biphenyl-4-yl sulfamate;
5'-((3H-[1,2,3]Triazolo[4,5-b]pyridin-3-yl)methyl)-2'-cyano-[1,1'-biphenyl]-4-yl sulfamate;
4-(2-((1H-Benzo[d]imidazol-1-yl)methyl)-5-cyanopyrimidin-4-yl)phenyl sulfamate;
4-(6-((1H-Benzo[d]imidazol-1-yl)methyl)-3-cyanopyridin-2-yl)phenyl sulfamate;
5'-(1H-Benzo[d][1,2,3]triazol-1-ylamino)-2'-cyanobiphenyl-4-yl sulfamate;
5'-((3H-Imidazo[4,5-b]pyridin-3-yl)methyl)-2'-cyano-[1,1'-biphenyl]-4-yl sulfamate;
5'-((1H-Benzo[d][1,2,3]triazol-1-yl)(methyl)amino)-2'-cyanobiphenyl-4-yl sulfamate;
4-(6-((3H-Imidazo[4,5-b]pyridin-3-yl)methyl)-3-cyanopyridin-2-yl)phenyl sulfamate;
4-(2-(1H-Benzo[d]imidazol-1-ylamino)-5-cyanopyrimidin-4-yl)phenyl sulfamate;
4-(2-((1H-Benzo[d]imidazol-1-yl)(methyl)amino)-5-cyanopyrimidin-4-yl)phenyl sulfamate;
4-(2-((1H-Benzo[d]imidazol-1-yl)methyl)-5-cyanopyridin-4-yl)phenyl sulfamate;
5'-((1H-Benzo[d]imidazol-1-yl)methyl)-2'-cyano-3-(methylthio)-[1,1'-biphenyl]-4-yl sulfamate;
5'-((1H-benzo[d]imidazol-1-yl)methyl)-2'-cyano-4-(methylthio)-[1,1'-biphenyl]-3-yl sulfamate
5'-((1H-Benzo[d]imidazol-1-yl)amino)-2'-cyano-3-(methylthio)-[1,1'-biphenyl]-4-yl sulfamate
5'-((1H-Benzo[d]imidazol-1-yl)amino)-2'-cyano-4-(methylthio)-[1,1'-biphenyl]-3-yl sulfamate
4-(6-(1H-Benzo[d]imidazol-1-ylamino)-3-cyanopyridin-2-yl)phenyl sulfamate;
4-(6-((1H-Benzo[d]imidazol-1-yl)(methyl)amino)-3-cyanopyridin-2-yl)phenyl sulfamate;
2'-Cyano-5'-((5,6-difluoro-1H-benzo[d]imidazol-1-yl)methyl)biphenyl-4-yl sulfamate;
4-(2-((3H-Imidazo[4,5-b]pyridin-3-yl)methyl)-5-cyanopyrimidin-4-yl)phenyl sulfamate;
4-(2-(1H-Benzo[d]imidazol-1-ylamino)-5-cyanopyridin-4-yl)phenyl sulfamate;
5'-((1H-Benzo[d]imidazol-1-yl)(methyl)amino)-2'-cyano-3-(methylthio)-[1,1'-biphenyl]-4-yl sulfamate;
5'-((1H-Benzo[d]imidazol-1-yl)(methyl)amino)-2'-cyano-4-(methylthio)-[1,1'-biphenyl]-3-yl sulfamate;
4-(2-((1H-Benzo[d]imidazol-1-yl)(methyl)amino)-5-cyanopyridin-4-yl)phenyl sulfamate;
6-(5-((1H-Benzo[d]imidazol-1-yl)methyl)-2-cyanophenyl)pyridin-3-yl sulfamate;
4-(5-((1H-Benzo[d]imidazol-1-yl)methyl)-2-cyanopyridin-3-yl)phenyl sulfamate;
4-(6-(1H-Benzo[d]imidazol-1-ylamino)-3-cyanopyrazin-2-yl)phenyl sulfamate;
6-(5-((3H-Imidazo[4,5-b]pyridin-3-yl)methyl)-2-cyanophenyl)pyridin-3-yl sulfamate;
4-(6-((1H-Benzo[d]imidazol-1-yl)(methyl)amino)-3-cyanopyrazin-2-yl)phenyl sulfamate
5'-(3H-[1,2,3]Triazolo[4,5-b]pyridin-3-ylamino)-2'-cyano-[1,1'-biphenyl]-4-yl sulfamate;
4-(2-((3H-Imidazo[4,5-b]pyridin-3-yl)methyl)-5-cyanopyridin-4-yl)phenyl sulfamate;
6-(5-((1H-Benzo[d]imidazol-1-yl)(methyl)amino)-2-cyanophenyl)pyridin-3-yl sulfamate;

4-(5-(1H-Benzo[d]imidazol-1-ylamino)-2-cyanopyridin-3-yl)phenyl sulfamate;
4-(5-((1H-Benzo[d]imidazol-1-yl)(methyl)amino)-2-cyanopyridin-3-yl)phenyl sulfamate
4-(6-(3H-Imidazo[4,5-b]pyridin-3-ylamino)-3-cyanopyrazin-2-yl)phenyl sulfamate;
6-(5-(1H-Benzo[d]imidazol-1-ylamino)-2-cyanophenyl)pyridin-3-yl sulfamate;
6'-((1H-Benzo[d]imidazol-1-yl)methyl)-3'-cyano-[2,2'-bipyridin]-5-yl sulfamate;
4-(5-(3H-Imidazo[4,5-b]pyridin-3-ylamino)-2-cyanopyridin-3-yl)phenyl sulfamate;
4-(6-((3H-Imidazo[4,5-b]pyridin-3-yl)(methyl)amino)-3-cyanopyrazin-2-yl)phenyl sulfamate;
4-(5-((3H-Imidazo[4,5-b]pyridin-3-yl)(methyl)amino)-2-cyanopyridin-3-yl)phenyl sulfamate;
4-(6-(3H-Imidazo[4,5-b]pyridin-3-ylamino)-3-cyanopyridin-2-yl)phenyl sulfamate;
4-(2-(3H-Imidazo[4,5-b]pyridin-3-ylamino)-5-cyanopyrimidin-4-yl)phenyl sulfamate;
4-(2-((3H-Imidazo[4,5-b]pyridin-3-yl)(methyl)amino)-5-cyanopyrimidin-4-yl)phenyl sulfamate;
4-(6-((3H-Imidazo[4,5-b]pyridin-3-yl)(methyl)amino)-3-cyanopyridin-2-yl)phenyl sulfamate;
4-(5-((3H-imidazo[4,5-b]pyridin-3-yl)methyl)-2-cyanopyridin-3-yl)phenyl sulfamate;
4-(2-Cyano-5-((5,6-difluoro-1H-benzo[d]imidazol-1-yl)methyl)pyridin-3-yl)phenyl sulfamate;
4-(5-Cyano-2-((5,6-difluoro-1H-benzo[d]imidazol-1-yl)methyl)pyrimidin-4-yl)phenyl sulfamate;

or a therapeutically acceptable salt thereof;

and more preferably from 4-(2-((1H-Benzo[d]imidazol-1-yl)methyl)-5-cyanopyrimidin-4-yl)phenyl sulfamate;
4-(2-((1H-Benzo[d]imidazol-1-yl)methyl)-5-cyanopyridin-4-yl)phenyl sulfamate;
4-(6-(1H-Benzo[d]imidazol-1-ylamino)-3-cyanopyridin-2-yl)phenyl sulfamate;
2'-Cyano-5'-((5,6-difluoro-1H-benzo[d]imidazol-1-yl)methyl)biphenyl-4-yl sulfamate;
4-(2-(1H-Benzo[d]imidazol-1-ylamino)-5-cyanopyridin-4-yl)phenyl sulfamate;
4-(5-((1H-Benzo[d]imidazol-1-yl)methyl)-2-cyanopyridin-3-yl)phenyl sulfamate;
5'-(3H-[1,2,3]Triazolo[4,5-b]pyridin-3-ylamino)-2'-cyano-[1,1'-biphenyl]-4-yl sulfamate;

or a therapeutically acceptable salt thereof.

In the present Application, the symbol-> * corresponds to the attachment point of the radical.

When the attachment site is not specified on the radical, this means that the attachment is carried out on one of the sites available on this radical for such an attachment.

Depending on the definitions of the variable groups A and L, the compounds (Ia), (Ib) and (I) according to the invention can be prepared according to the reaction schemes provided hereinafter.

The compounds of the invention with general formula (I) where A, B, C, and L are as defined above can be obtained by reaction of a phenolic general compound GP1, where A, B, C and L are defined as above, with a sulfamoylating agent such as sulfamoyl chloride in a polar aprotic solvent such as N,N-dimethylacetamide at room temperature.

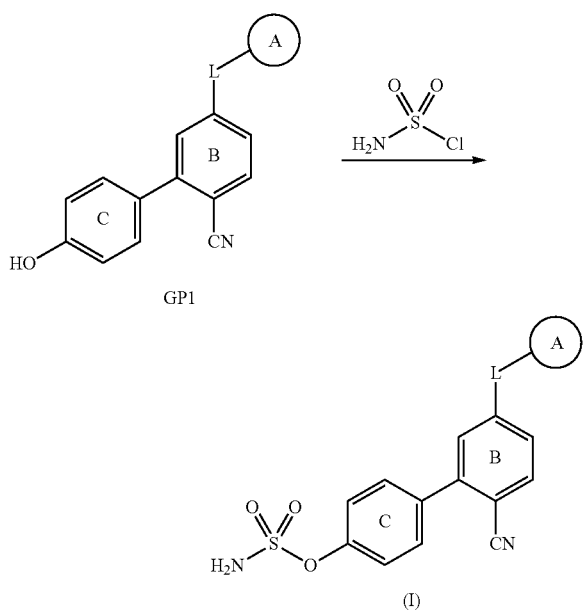

GP1

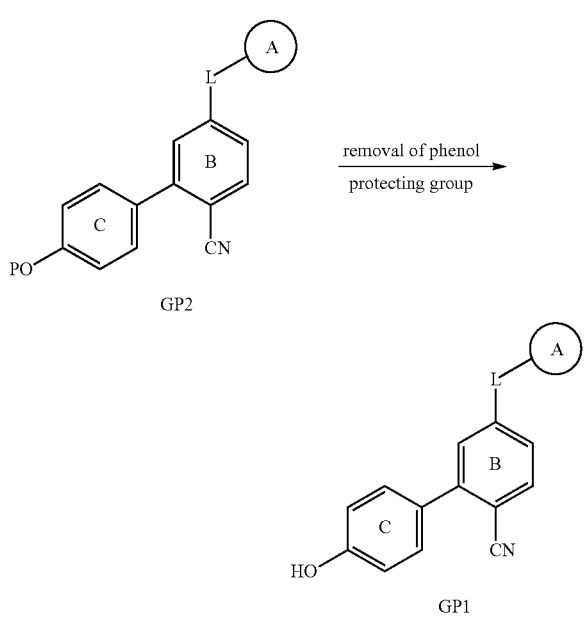

GP2 removal of phenol protecting group →

GP1

Although sulfamoyl chloride is reputed to be commercially available it can be conveniently prepared on site by careful decomposition of chlorosulfonyl isocyanate with formic acid. It must be noted that one equivalent of highly toxic gaz carbon monoxide is generated in this process which should therefore be conducted with due attention to safety precautions. In case at least one of R and R' is not hydrogen, appropriate alkyl or dialkyl sulfamoyle derivatives can be used as sulfamoylating agent.

Phenolic general compounds GP1 where A, B, C and L are defined as above can be obtained from general compound GP2 where A, B, C and L are defined as above and PO represents a protected phenol function.

The concept of protecting group is well known to the skilled person of the art as illustrated by reference books such as "Greene's Protective Groups in Organic Synthesis" by Peter G. M. Wuts and Theodora W. Greene, Wiley, 2007. The phenol protecting groups used in the following exemples are ethers derived from the following groups: methyl (Me), benzyl (Bn), and (trimethylsilyl)ethoxymethyl (SEM). A wide array of general methods is available to the skilled of the art to remove phenol protecting groups and provide the corresponding free phenol. These methods usually involve activation of the phenolic ether function with strong Brønsted acids such as trifluoroacetic acid or concentrated hydrobromic acid, or Lewis acids such as or boron tribromide. The Bn group can also be removed by hydrogenolysis in the presence of a palladium catalyst. The SEM group can be removed via a beta-elimination mechanism triggered by the nucleophilic displacement of the trimethylsilyl function by fluoride ions. Tetrabutylammonium fluoride is a widely used reagent as source of fluoride ions.

General compound GP2 where A, B, C and P are defined as above, and L is —N(alkyl)- or —N(cycloalkyl-methyl)- can be obtained from GP2 where A, B, C and P are as defined above, and L is —NH—, by alkylation or (cycloalkyl)-methylation. In case of methylation (i.e. alkyl is methyl), the scheme is as follows:

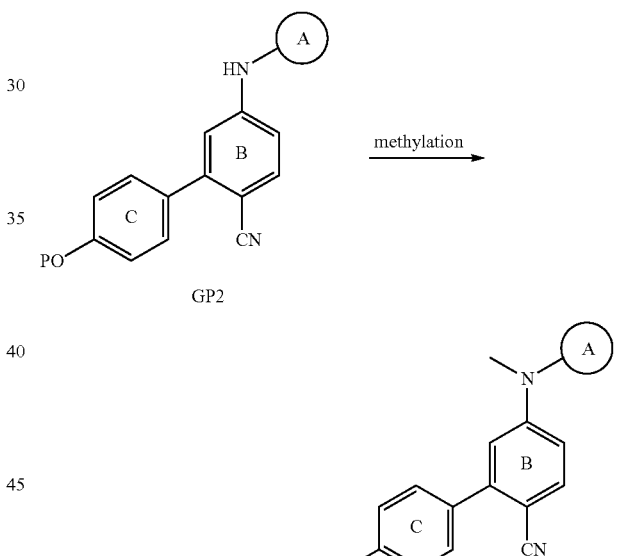

GP2 methylation →

GP2

Such reaction is obtained, for instance, by treatment of the corresponding substrate with an electrophilic alkyl or (cycloalkyl)-methyl reagent such as alkyl iodide, alkyl sulfate or (bromomethyl)cyclopropane, in the presence of a strong base such as sodium hydride, potassium tert-butoxide, potassium carbonate, or cesium carbonate, in an aprotic solvent such as THF or DMF, at a temperature between 0° C. and 60° C., preferably at room temperature. Protected phenolic general compounds GP2, where A, B, C and L are as defined above and PO represents a protected phenolic function, can be obtained from general compound GP3 where C and PO are as defined above and compound GP4 where A, B and L are as defined above, and X is an halogen. M represents the organometallic functional group in compound GP3, selected among boron- or tin-based functions.

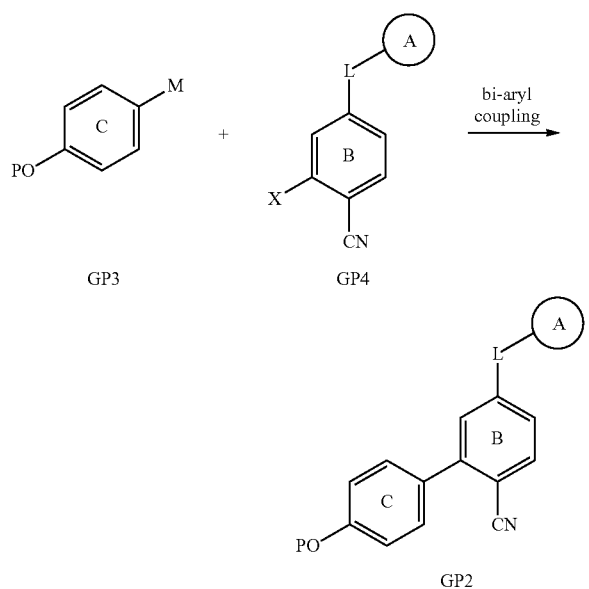

GP3  GP4

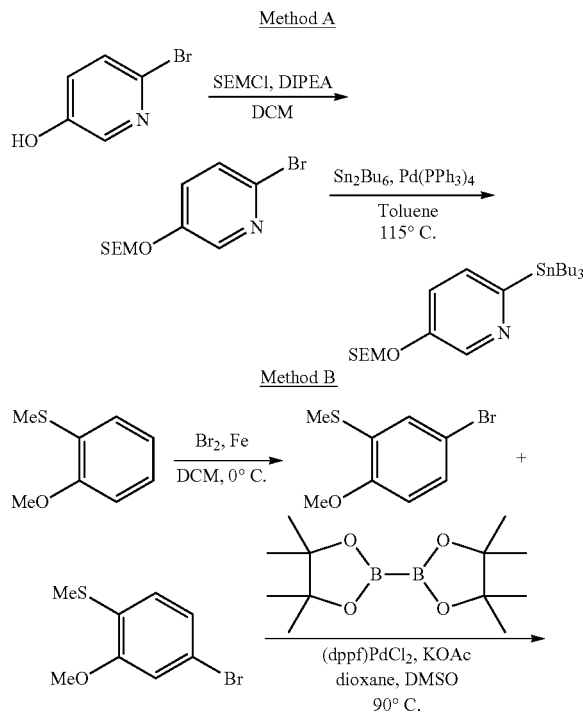

GP2

These bi-aryl coupling, well-known by those skilled in the art, are usually performed in the presence palladium-phosphine catalysts provided by reagents such as for example, $Pd(PPh_3)_4$, $Pd(OAc)_2$/XPhos, in the presence of inorganic bases such as potassium carbonate, cesium carbonate, potassium phosphate. The reactions are conducted in solvents or solvent mixtures comprising such as toluene, dioxane, ethanol, water, at temperature of 80° C. to 120° C.

General compounds GP3 may be commercially available such as, for example, 4-methoxyphenylboronic acid, 4-benzyloxyphenylboronic acid and their corresponding pinacol boronic esters. Other general compounds GP3 can be prepared according to with the following methods.

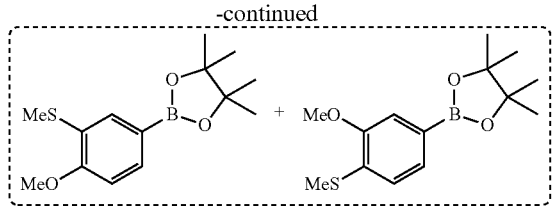

As depicted above, bromination of o-methylthio-anisole provides two distinct region-isomers which are transformed into the desired boronic derivatives as a mixture and engaged as such into further chemical transformation toward the corresponding final product bearing a methylsulfide. Separation of the region-isomers is usually carried-on at the penultimate stage, where the phenol protecting group is removed, and sulfamoylation is performed with isomerically pure substrates. It will appear obvious to the skill in the art that isomeric separation could take place at earlier stage in the process.

General compound GP4 where A, B are defined as above, X is an halogen and L is $CH_2$, can be obtained from the corresponding general compound GP5, where B and X are define as above, bearing a benzylic halide (Y) by nucleophilic displacement with the sp3 nitrogen atom of the azole part of the A ring.

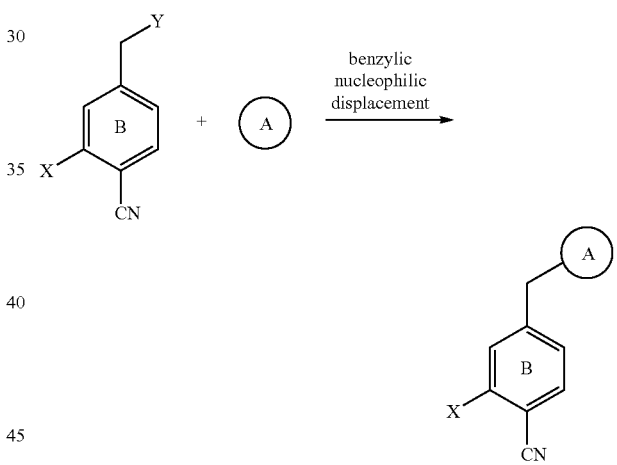

For example, the following heterocycles A1, A2, A3, A4, A5 and A6 which are known to the man skilled in the art, may be engaged in such process.

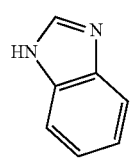

A1

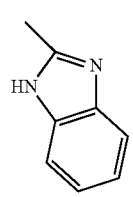

A2

-continued

A3 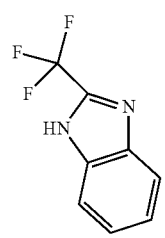

A4 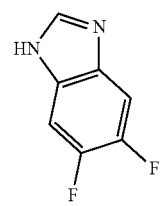

A5 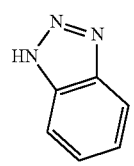

A6 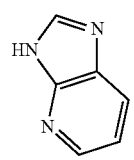

Examples of general compound GP5 may be prepared by the following methods;

-continued

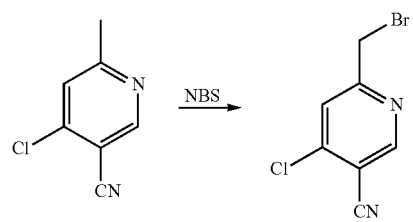

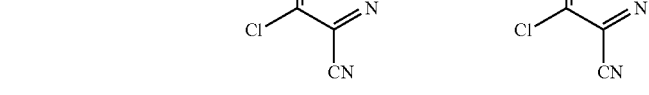

General compound GP4 where A, B are defined as above, X is an halogen and L is CH$_2$ can be obtained from the corresponding general compound GP5, where B and X are define as above, bearing a benzylic halide Y, by benzylic amination, followed by nucleophilic aromatic substitution with the resulting benzylic amine, and completion of the A-ring synthesis with the appropriate functional group manipulation and cyclisation. An example of such transformation is given as follow:

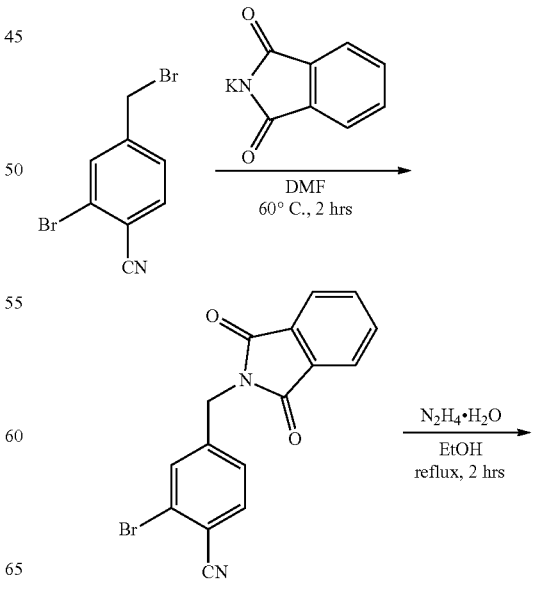

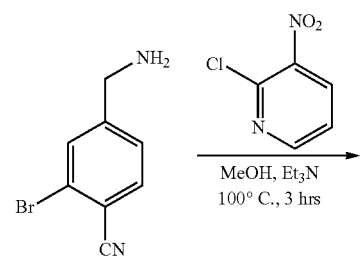

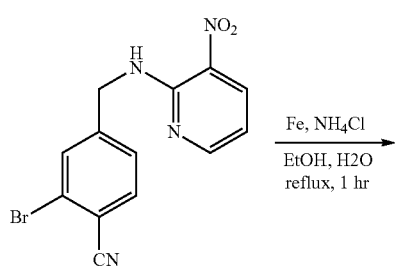

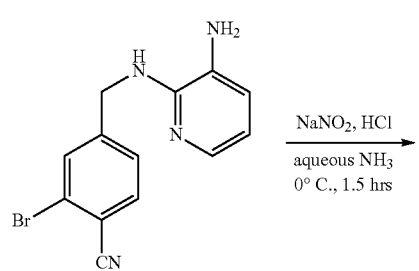

General compound GP4 where A, B are as defined above, X is a halogen and L is —NH— can be obtained from GP6, where B and X are as defined above and F is a fluorine atom, by nucleophilic aromatic substitution with a hydrazine derivative of heterocycle A

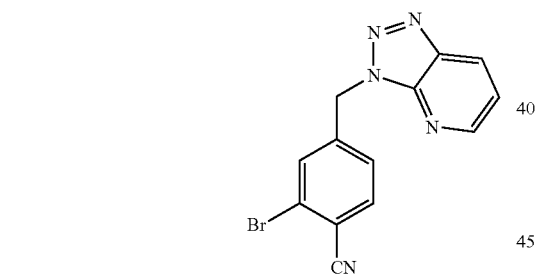

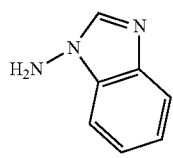

GP4 such as, for example, H$_2$N-A1, H$_2$N-A5, H$_2$N-A6, and H$_2$N-A7

H$_2$N-A1

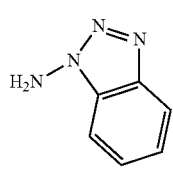

H$_2$N-A5

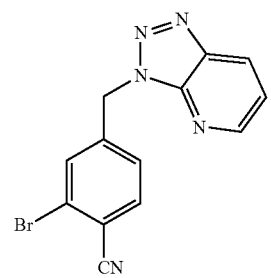

H$_2$N-A6

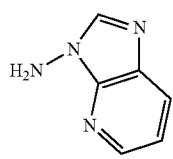

H$_2$N-A7

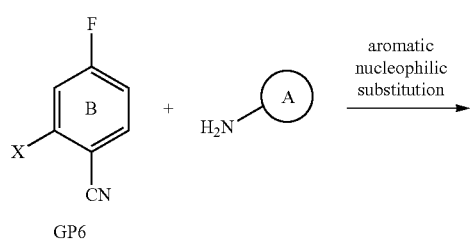

The new compounds H$_2$N-A6, and H$_2$N-A7 may be prepared as follows:

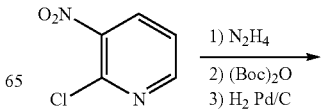

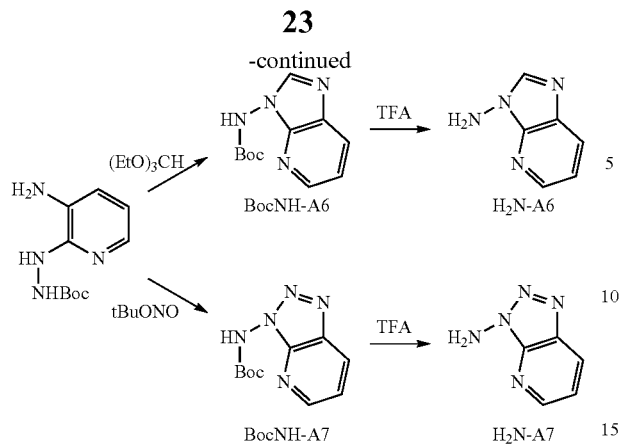

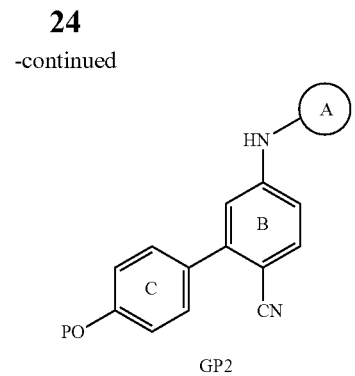

General compound GP4 where A, B are as defined above, X is a halogen and L is —N(Me)- can be obtained from GP4 where A, B are defined as above, X is a halogen and L is —NH—, by methylation or more generally alkylation. Such reaction is obtained, for instance, by treatment of the corresponding substrate with an electrophilic methyl or alkyl reagent such as methyl iodide, methyl sulfate or (bromomethyl)cyclopropane, in the presence of a strong base such as sodium iodide, potassium tert-butoxide, potassium carbonate, or cesium carbonate, in an aprotic solvent such as THF or DMF, at a temperature between 0° C. and 60° C., preferably at room temperature.

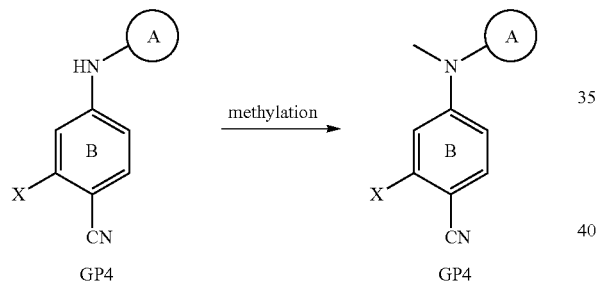

Protected phenolic general compounds GP2, where A, B, C are defined as above, and PO represents a protected phenolic function can be obtained from general compound GP7 where B, C and PO are defined as above by aromatic amination with a hydrazine derivative of heterocycle A such as, for example, H₂N-A1, H₂N-A5, H₂N-A6, and H₂N-A7, or their Boc-derivatives, to replace the Z substituent, a halogen atom. Such aromatic amination reactions take place either by nucleophilic aromatic substitution or by palladium catalyzed aromatic amination, both reaction mechanisms are well known to the skilled person.

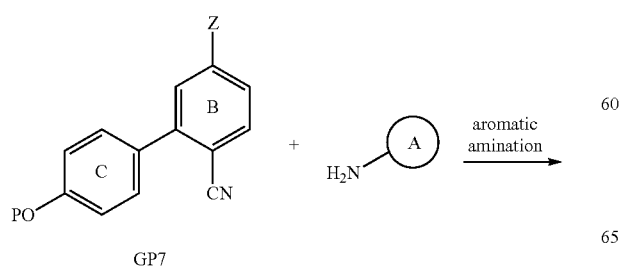

General compound GP7 where B, C, Z and PO are as defined above can be from general compound GP3 where C, M and PO are as defined above and general compound GP8 where X is a halogen. B1 ring represents a compound precursor to the B ring of GP7 wherein further functional groups manipulations are needed to bring in the cyano and Z substituents of GP7.

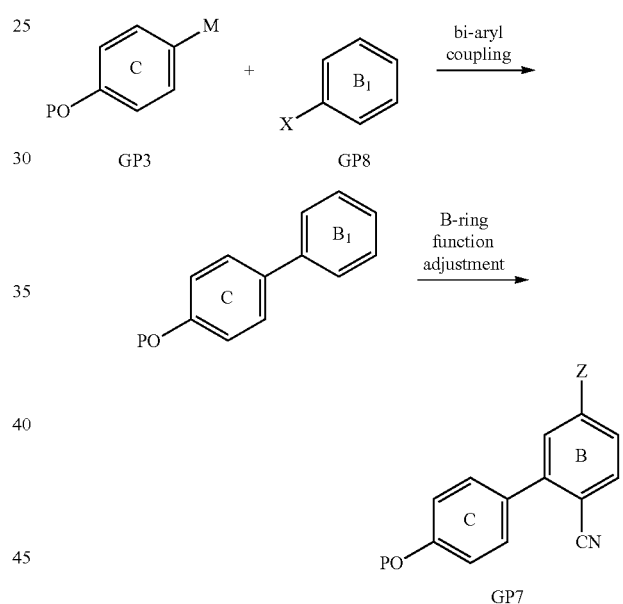

Examples of such processes are shown below:

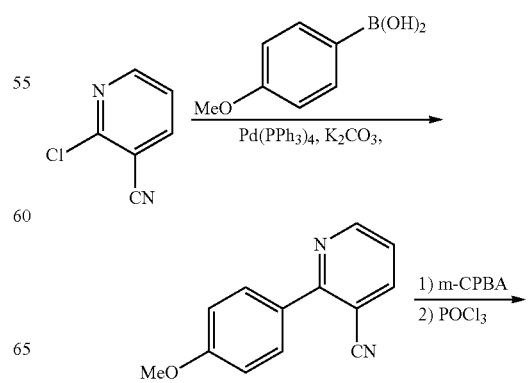

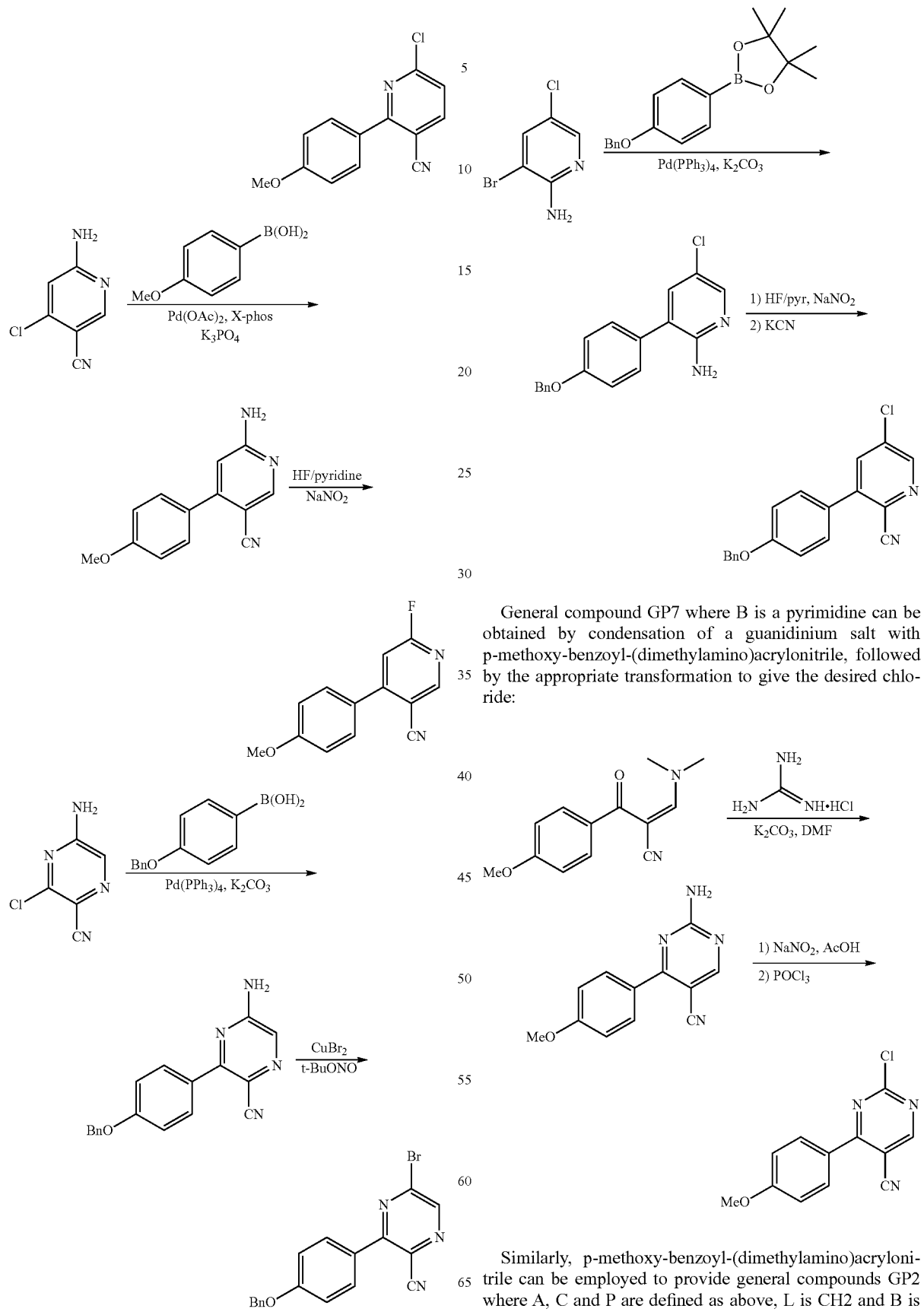

General compound GP7 where B is a pyrimidine can be obtained by condensation of a guanidinium salt with p-methoxy-benzoyl-(dimethylamino)acrylonitrile, followed by the appropriate transformation to give the desired chloride:

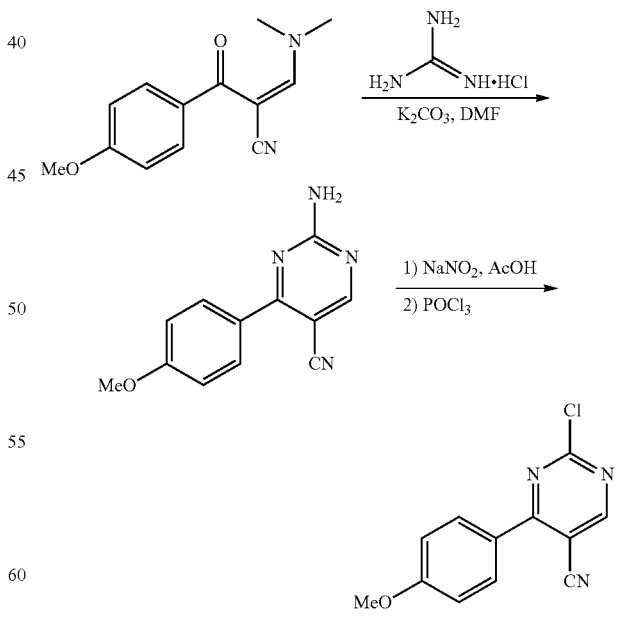

Similarly, p-methoxy-benzoyl-(dimethylamino)acrylonitrile can be employed to provide general compounds GP2 where A, C and P are defined as above, L is CH2 and B is a pyrimidine:

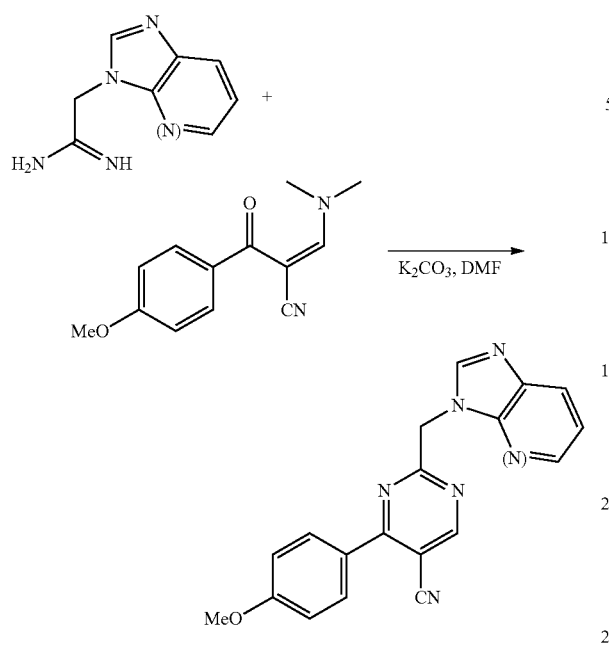

The reaction schemes above illustrate specifically the preparation of compounds (Ia) wherein the $H_2N-SO_2-O-$ radical is at the para position of C ring (i.e compounds of formula (I)). Of course, the reaction schemes may be easily transposed for the compounds (Ia) with the $H_2N-SO_2-O-$ radical at the meta position of C ring by those skilled in the art of organic chemistry.

The present invention relates also to a process for the preparation of a compound of formula (I), said process comprising a) either coupling a compound of formula GP3a

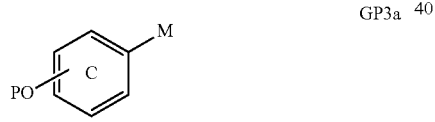

GP3a wherein C is as defined above, PO represents a protected phenol function in meta or para position in the C ring, and M an organometallic functional group, with a compound of formula GP4a

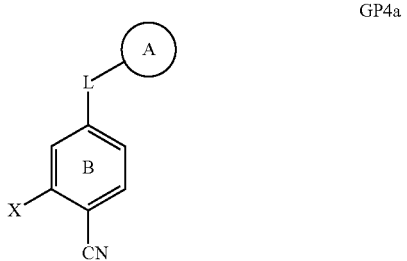

GP4a wherein A, B and L are defined as above and X is an halogen, with a catalyst in the presence of an inorganic base, in solvents or solvent mixtures at temperature of 80° C. to 120° C., or a compound of formula GP7a

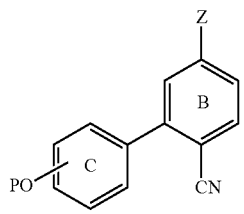

GP7a wherein B, C and L are as defined above, Z represents a halogen atom and PO a protected phenol function in meta or para position in the C ring, by aromatic amination with a hydrazine derivative of formula

wherein A is as defined above and Y represents hydrogen or Boc, to form a compound of formula GP2a

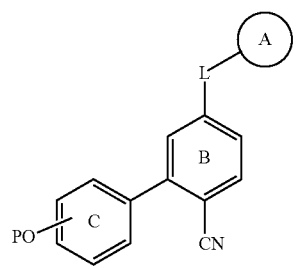

GP2a b) then removing the phenol protecting group of the compound GP2a, to form the corresponding phenolic compound GP1a

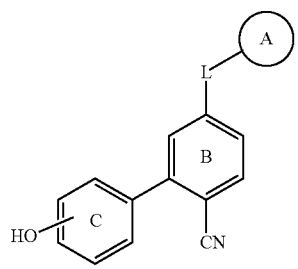

GP1a wherein A, B, C and L are as defined above, and c) finally reacting the phenolic general compound GP1a with a sulfamoylating agent in a polar aprotic solvent at room temperature, to form the compound of formula (Ia)

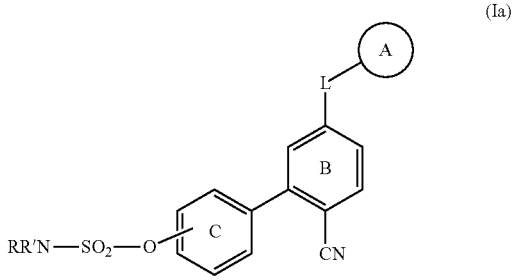

wherein A, B, C, R, R' and L are as defined above.

The present invention relates also to compounds of formula (II)

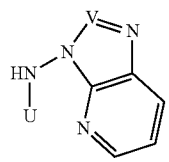

wherein V represents N, CH or C(alkyl), U represents H, alkyl, alkyl-C(O)— or Boc. These compounds are useful as intermediate for the preparation of compounds of formula (Ia).

In a preferred embodiment, the present invention relates also to compounds of formula (II) as described above wherein V represents N, CH or C(alkyl), U represents H, alkyl or Boc.

The present invention relates also to compounds of formula (III)

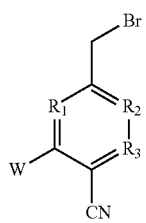

wherein at least one of $R_1$, $R_2$ and $R_3$ is N and the others CH—, W represents chloro, iodo, bromo, mesylate or tosylate, These compounds are useful as intermediate for the preparation of compounds of formula (Ia).

In a preferred embodiment, the present invention relates also to compounds of formula (III) as described above, wherein at least one of $R_1$, $R_2$ and $R_3$ is N and the others CH— and W represents chloro or bromo.

The compounds of the present invention have useful pharmacological properties. It has thus been discovered that the compounds Ia of the present invention are dual inhibitors of aromatase and sulfatase.

The compounds of the present invention can thus be used in different therapeutic applications. They can advantageously be used for treating the pathological states or diseases in which aromatase and sulfatase are involved such as endometriosis, fibrosis, benign prostatic hyperplasia (BPH) and gynecolotgical pathologies, cancer in particular ovarian, breast, prostate, cervical or gastric cancer. Hereafter, in the experimental part, an illustration will be found of the pharmacological properties of the compounds of the invention.

A subject of the present invention is also pharmaceutical compositions containing, as active ingredient, at least one product of formula (Ia) as defined above, as well as the pharmaceutically acceptable salts of said product of formula (Ia), in combination with a pharmaceutically acceptable support.

By pharmaceutically acceptable salt, is understood in particular addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, pamoate and stearate. Also within the scope of the present invention, when they can be used, the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example, powders, granules, tablets, gelatin capsules or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or the glycols, as well as their mixtures, in varying proportions, in water, added to pharmaceutically acceptable oils or greases. The sterile liquid compositions can be used for intramuscular, intraperitoneal or sub-cutaneous injections and the sterile compositions can also be administered by intravenous route.

All the technical and scientific terms used in the present text have the meaning known to a person skilled in the art. Moreover, all the patents (or patent applications) as well as the other bibliographical references are incorporated by way of reference.

EXPERIMENTAL PART

EXAMPLE 1

5'-((1H-Benzo[d]imidazol-1-yl)methyl)-2'-cyano-[1,1'-biphenyl]-4-yl sulfamate

Step A. 2-Bromo-4-(bromomethyl)benzonitrile

A solution of 2-bromo-4-methylbenzonitrile (29 g, 151 mmol), benzoyl peroxide (2.2 g, 9.2 mmol), and N-bromosuccinimide (NBS) (34 g, 151 mmol) in CCl$_4$ (500 mL) was stirred at 85° C. for 4 hours. The reaction mixture was cooled to 23° C., filtered, and concentrated under reduced pressure. The residue was recrystallized form Petroleum Ether:EtOAc (10:1) to afford 2-bromo-4-(bromomethyl)benzonitrile as a white solid (25 g, 60%). MS (ESI) m/z: 274 [M+H]$^+$.

Step B. 4-((1H-Benzo[d]imidazol-1-yl)methyl)-2-bromobenzonitrile

A mixture of 2-bromo-4-(bromomethyl)benzonitrile (2 g, 7.4 mmol), 1H-benzo[d]imidazole (1.05 g, 8.8 mmol), and $K_2CO_3$ (3.06 g, 22.2 mmol) in MeCN (30 mL) was heated at 40° C. for 3 hours. The reaction mixture was cooled, concentrated under reduced pressure and purified by chromatography using $CH_2Cl_2$:EtOAc (1:1) as eluting solvents to afford 4-((1H-benzo[d]imidazol-1-yl)methyl)-2-bromobenzonitrile as a yellow solid (1.2 g, 50%). MS (ESI) m/z: 312 [M+H]$^+$.

Step C. 5-((1H-Benzo[d]imidazol-1-yl)methyl)-4'-methoxy-[1,1'-biphenyl]-2-carbonitrile A mixture of 4-((1H-benzo[d]imidazol-1-yl)methyl)-2-bromobenzonitrile (1.2 g, 3.8 mmol), 4-methoxyphenylboronic acid (0.53 g, 4.2 mmol), Pd(PPh$_3$)$_4$ (0.037 g, 0.03 mmol), and $K_2CO_3$ (1.3 g, 9.6 mmol) in 1,4-dioxane (25 mL) and $H_2O$ (5 mL) was purged with nitrogen and heated at 80° C. overnight. The reaction mixture was concentrated under reduced pressure and the residue purified by silica gel chromatography using $CH_2Cl_2$:EtOAc (1:1) as eluting solvents to afford 5-((1H-benzo[d]imidazol-1-yl)methyl)-4'-methoxy-[1,1'-biphenyl]-2-carbonitrile as a yellow solid (1.5 g, 95%). $^1$H NMR (500 MHz, CDCl$_3$) δ (ppm) 7.96 (s, 1H), 7.79 (d, J=8 Hz, 1H), 7.63 (d, J=7.5 Hz, 1H), 7.35 (d, J=9 Hz, 2H), 7.26-7.19 (m, 4H), 7.07 (d, J=8 Hz, 1H), 6.92-6.89 (m, 2H), 5.40 (s, 2H), 3.78 (s, 3H). MS (ESI) m/z: 340 [M+H]$^+$.

Step D. 5-((1H-Benzo[d]imidazol-1-yl)methyl)-4'-hydroxy-[1,1'-biphenyl]-2-carbonitrile A mixture of 5-((1H-benzo[d]imidazol-1-yl)methyl)-4'-methoxy-[1,1'-biphenyl]-2-carbonitrile (1.3 g, 3.8 mmol) in HBr (48 wt. % in $H_2O$, 20 mL) was heated at 120° C. for 1 hour in a microwave oven. The reaction mixture was concentrated under reduced pressure and basified by adding a saturated aqueous solution of NaHCO$_3$ to afford 5-((1H-benzo[d]imidazol-1-yl)methyl)-4'-hydroxy-[1,1'-biphenyl]-2-carbonitrile as a white solid (0.62 g, 44%). $^1$HNMR (500 MHz, DMSO-d$_6$) δ (ppm) 8.47 (s, 1H), 7.85 (d, J=7.5 Hz, 1H), 7.68-7.66 (m, 1H), 7.57-7.54 (m, 2H), 7.36 (d, J=9 Hz, 2H), 7.31-7.29 (m, 1H), 7.24-7.19 (m, 2H), 6.89 (d, J=8.5 Hz, 2H), 5.64 (s, 2H); MS (ESI) m/z: 326 [M+H]$^+$.

Step E. 5'-((1H-Benzo[d]imidazol-1-yl)methyl)-2'-cyano-[1,1'-biphenyl]-4-yl sulfamate E.1: Sulfamoyl Chloride
Caution: this experiment must be performed under a fume hood since a strong release of carbon dioxide and carbon monoxide occurs.

Chlorosulfonyl isocyanate (17.4 mL, 200 mmol) was introduced into a 250 mL round bottom flask. Under an inert atmosphere, formic acid (7.54 mL, 200 mmol) was slowly added followed by toluene (60 mL). The resulting mixture was stirred 10 hours at 23° C. The solvent was removed to dryness under reduced pressure to afford the final product as a crystalline solid (23 g, quantitative yield). The compound was used in the next steps without further purification.

E.2: 5'-((1H-Benzo[d]imidazol-1-yl)methyl)-2'-cyano-[1,1'-biphenyl]-4-yl sulfamate
A mixture of 5-((1H-benzo[d]imidazol-1-yl)methyl)-4'-hydroxy-[1,1'-biphenyl]-2-carbonitrile (150 mg, 0.46 mmol) and sulfamoyl chloride (800 mg, 6.9 mmol) in DMA (8 mL) was stirred at room temperature overnight. The reaction mixture was concentrated under reduced pressure. The residue was purified by preparative HPLC to afford 5'-((1H-benzo[d]imidazol-1-yl)methyl)-2'-cyano-[1,1'-biphenyl]-4-yl sulfamate as white solid (20 mg, 11%). $^1$HNMR (500 MHz, CD$_3$OD) δ (ppm) 8.26 (s, 1H), 7.71 (d, J=8 Hz, 1H), 7.61 (d, J=4 Hz, 1H), 7.48-7.46 (m, 2H), 7.35-7.32 (m, 4H), 7.26-7.24 (m, 1H), 7.20-7.18 (m, 4H), 5.58 (s, 2H); MS (ESI) m/z: 405 [M+H]$^+$.

Example 2

5'-(1H-Benzo[d]imidazol-1-ylamino)-2'-cyano-[1,1'-biphenyl]-4-yl sulfamate

Step A. 1H-Benzo[d]imidazol-1-amine

To a solution of 1H-benzo[d]imidazole (11.8 g, 100 mmol) and KOH (16.8 g, 300 mmol) in water (50 mL) at 45° C. was slowly added a solution of aminooxysulfonic acid (20 g, 160 mmol) in $H_2O$ (80 mL), which pH was adjusted to about 7 with NaHCO$_3$. The mixture was stirred for 10 minutes, cooled with ice-bath, stirred 0° C. for 15 minutes, and then heated at 55° C. for 30 minutes, filtered, and dried to afford 1H-benzo[d]imidazol-1-amine as a white solid (8 g, 62%). MS (ESI) m/z: 134 [M+H]$^+$.

Step B. 4-(1H-Benzo[d]imidazol-1-ylamino)-2-bromobenzonitrile

To a solution of t-BuOK (6.21 g, 55 mmol) in DMSO (50 mL) at 25° C. was added dry 1H-benzo[d]imidazol-1-amine (7.32 g, 55 mmol). After stirring for 30 minutes, 2-bromo-4-fluorobenzonitrile (2 g, 10 mmol) was slowly added and the mixture further stirred at 25° C. for 2 hours. The reaction mixture was quenched with water, filtered, concentrated under reduced pressure to afford the title compound as a white solid (3 g, 19%). MS (ESI) m/z: 313 [M+H]$^+$.

Step C. 5-(1H-Benzo[d]imidazol-1-ylamino)-4'-methoxy-[1,1'-biphenyl]-2-carbonitrile A mixture of 4-(1H-benzo[d]imidazol-1-ylamino)-2-bromobenzonitrile (624 mg, 2 mmol), 4-methoxyphenylboronic acid (453 mg, 3 mmol), Pd(PPh$_3$)$_4$ (115 mg, 0.10 mmol), and $K_2CO_3$ (550 g, 4 mmol) in 1,4-dioxane (15 mL) and $H_2O$ (5 mL) was purged with nitrogen and heated at 90° C. for 3 hours. The reaction mixture was cooled and filtered. The filtrate was evaporated, purified by silica gel chromatography using Petroleum Ether:EtOAc. The title compound was obtained as yellow solid (670 mg, 98%). MS (ESI) m/z: 341 [M+H]$^+$.

Step D. 5-(1H-Benzo[d]imidazol-1-ylamino)-4'-hydroxy-[1,1'-biphenyl]-2-carbonitrile To a solution of 5-(1H-benzo[d]imidazol-1-ylamino)-4'-methoxy-[1,1'-biphenyl]-2-carbonitrile (280 mg, 0.82 mmol) in $CH_2Cl_2$ (5 mL) at −78° C. was added BBr$_3$ (3.0 N, 1.7 mL, 5 mmol). The mixture was stirred at 20° C. for 20 hours. Then the mixture was quenched with water and its pH was adjusted to about 8 with an aqueous saturated solution of Na$_2$CO$_3$ to form a solid. After filtration and drying, the title compound was obtained as red solid (220 mg, 82%). $^1$H NMR (500 MHz, DMSO-d$_6$) δ (ppm) 10.31 (s, 1H), 9.78 (s, 1H), 8.47 (s, 1H), 7.76-7.74 (m, 1H), 7.69 (d, J=8.5 Hz, 1H), 7.34-7.26 (m, 5H), 6.84 (d, J=8.5 Hz, 2H), 6.51 (s, 1H), 6.42 (d, J=7.5 Hz, 1H); MS (ESI) m/z: 327[M+H]$^+$.

Step E. 5'-(1H-Benzo[d]imidazol-1-ylamino)-2'-cyano-[1,1'-biphenyl]-4-yl sulfamate The procedure described in Example 1 step E was repeated using 5-(1H-benzo[d]imidazol-1-ylamino)-4'-hydroxy-[1,1'-biphenyl]-2-carbonitrile (140 mg) to obtain the title compound as white solid (40 mg, 23%). $^1$H NMR (500 MHz, DMSO-d$_6$) δ (ppm) 10.41 (s, 1H), 8.47 (s, 1H), 8.09 (s, 2H), 7.78-7.74 (m, 2H), 7.54 (d, J=8.5 Hz, 2H), 7.38 (d, J=9.0 Hz, 2H), 7.33-7.28 (m, 3H), 6.52 (s, 2H); MS (ESI) m/z: 406 [M+H]$^+$.

Example 3

2'-Cyano-5'-((2-methyl-1H-benzo[d]imidazol-1-yl)methyl)biphenyl-4-yl sulfamate

Compound of Example 3 was prepared in the same manner as described for compound of Example 1 starting from 2-bromo-4-(bromomethyl)benzonitrile and 2-methyl-1H-benzo[d]imidazole. The title compound was obtained as a white solid (30 mg). $^1$HNMR (500 MHz, DMSO-d$_6$) δ (ppm) 7.92 (d, J=8.5 Hz, 1H), 7.62 (d, J=8.5 Hz, 2H), 7.57-7.55 (m, 1H), 7.48-7.46 (m, 1H), 7.42 (d, J=8.5 Hz, 2H), 7.36 (s, 1H), 7.15-7.19 (m, 3H), 5.65 (s, 2H), 2.53 (s, 3H); MS (ESI) m/z: 419 [M+H]$^+$.

Example 4

5'-((1H-Benzo[d][1,2,3]triazol-1-yl)methyl)-2'-cyano-[1,1'-biphenyl]-4-yl sulfamate Step A. 4-((1H-Benzo[d][1,2,3]triazol-1-yl)methyl)-2-bromobenzonitrile A solution of 2-bromo-4-(bromomethyl)benzonitrile (2.5 g, 9 mmol) [Example 1 Step A], 1H-benzo[d][1,2,3]triazole (1.1 g, 10 mmol), and K$_2$CO$_3$ (3.8 g, 27 mmol) in CH$_3$CN (50 mL) was stirred for 12 hours at 25° C. The reaction mixture was cooled to 0° C., filtered, and concentrated under reduced pressure. The residue was purified by silica gel chromatography using Petroleum Ether:EtOAc (30:1 to 3:1) as eluting solvents to afford 4-((1H-benzo[d][1,2,3]triazol-1-yl)methyl)-2-bromobenzonitrile as a yellow solid (1.52 g, 53%). MS (ESI) m/z: 313 [M+H]$^+$.

Step B. 5'-((1H-Benzo[d][1,2,3]triazol-1-yl)methyl)-2'-cyano-[1,1'-biphenyl]-4-yl sulfamate The procedures described in Example 2 steps C, D and E were repeated using 4-((1H-benzo[d][1,2,3]triazol-1-yl)methyl)-2-bromobenzonitrile to obtain the title compound as a yellow solid (38 mg, 27%). $^1$H NMR (500 MHz, DMSO-d$_6$) δ (ppm) 8.14 (brs, 2H), 8.08 (d, J=8.5 Hz, 1H), 7.95 (d, J=8 Hz, 1H), 7.92 (d, J=8.5 Hz, 1H), 7.65 (d, J=9 Hz, 2H), 7.62 (s, 1H), 7.58 (t, 1H), 7.43 (d, J=8.5 Hz, 2H), 7.42 (d, J=6 Hz, 2H), 6.13 (s, 2H); MS (ESI) m/z: 406 [M+H]$^+$.

Example 5

5'-((1H-Benzo[d]imidazol-1-yl)(methyl)amino)-2'-cyano-[1,1'-biphenyl]-4-yl sulfamate Step A. 5-((1H-Benzo[d]imidazol-1-yl)(methyl)amino)-4'-methoxy-[1,1'-biphenyl]-2-carbonitrile To a solution of NaH (60 mg, 1.50 mmol) in THF (7 mL) at 0° C. was added 5-(1H-benzo[d]imidazol-1-ylamino)-4'-methoxy-[1,1'-biphenyl]-2-carbonitrile (340 mg, 1 mmol) [Example 2 Step C]. The mixture was stirred for 15 minutes before addition, at 0° C., of iodomethane (284 mg, 2 mmol) in a dropwise manner. After a 2-hour stirring at 25° C., the reaction mixture was quenched with MeOH and concentrated under reduced pressure. The residue was purified by preparative HPLC to afford the title compound as a white solid (300 mg, 84%). MS (ESI) m/z: 355 [M+H]$^+$.

Step B. 5'-((1H-Benzo[d]imidazol-1-yl)(methyl)amino)-2'-cyano-[1,1'-biphenyl]-4-yl sulfamate The procedures described in Example 2 steps D and E were repeated using 5-((1H-benzo[d]imidazol-1-yl)(methyl)amino)-4'-methoxy-[1,1'-biphenyl]-2-carbonitrile (170 mg) to obtain the title compound as white solid (120 mg, 57%). $^1$H NMR (500 MHz, DMSO-d$_6$) δ (ppm) 8.58 (s, 1H), 7.79-7.77 (m, 2H), 7.59 (d, J=8.5 Hz, 2H), 7.40-7.30 (m, 6H), 6.69 (d, J=2.0 Hz, 1H), 6.50-6.48 (m, 1H), 3.64 (s, 3H); MS (ESI) m/z: 420 [M+H]$^+$.

Example 6

5'-((1H-Benzo[d]imidazol-1-yl)(cyclopropylmethyl)amino)-2'-cyano-[1,1'-biphenyl]-4-yl sulfamate Compound of Example 6 was prepared in the same manner as described for compound of Example 5 starting from 5-(1H-benzo[d]imidazol-1-ylamino)-4'-methoxy-[1,1'-biphenyl]-2-carbonitrile [Example 2 Step C] and (bromomethyl)cyclopropane. The title compound was obtained as white solid (150 mg). $^1$H NMR (500 MHz, DMSO-d$_6$) δ (ppm) 8.55 (s, 1H), 8.11 (s, 2H), 7.79-7.76 (m, 2H), 7.59 (d, J=9.0 Hz, 2H), 7.40-7.28 (m, 5H), 6.72 (d, J=2.5 Hz, 1H), 6.54-6.52 (m, 1H), 4.02-3.97 (m, 1H), 3.8-3.76 (m, 1H), 0.86-0.82 (m, 1H), 0.33 (d, J=8.0 Hz, 2H), 0.12-0.10 (m, 1H), 0.01-0.04 (m, 1H); MS (ESI) m/z: 460 [M+H]$^+$.

Example 7

2'-Cyano-5'-((2-(trifluoromethyl)-1H-benzo[d]imidazol-1-yl)methyl)biphenyl-4-yl sulfamate Compound of Example 7 was prepared in the same manner as described for compound of Example 1 starting from 2-bromo-4-(bromomethyl)benzonitrile and 2-(trifluoromethyl)-1H-benzo[d]imidazole. The title compound was obtained as a gray solid (30 mg, 17%). $^1$HNMR (500 MHz, DMSO-d$_6$) δ (ppm) 8.14 (s, 2H), 7.93-7.89 (m, 2H), 7.73 (d, J=8 Hz, 1H), 7.62 (d, J=8.5 Hz, 2H), 7.47 (d, J=7.5 Hz, 1H), 7.44-7.41 (m, 4H), 7.11 (d, J=8 Hz, 1H), 5.89 (s, 2H); MS (ESI) m/z: 473 [M+H]$^+$.

Example 8

5'-((3H-[1,2,3]Triazolo[4,5-b]pyridin-3-yl)methyl)-2'-cyano-[1,1'-biphenyl]-4-yl sulfamate Step A. 2-Bromo-4-((1,3-dioxoisoindolin-2-yl)methyl)benzonitrile A solution of 2-bromo-4-(bromomethyl)benzonitrile (25 g, 90 mmol) and potassium phthalimide (18 g, 97 mmol) in DMF (200 mL) was stirred at 60° C. for 3 hours. The reaction mixture was cooled to room temperature and poured into water (1 L). The precipitate thus formed was filtered and the filter cake was collected to afford a crude 2-bromo-4-((1,3-dioxoisoindolin-2-yl)methyl)benzonitrile as a white solid, which was used without further purification. MS (ESI) m/z: 341 [M+H]$^+$.

Step B. 4-(Aminomethyl)-2-bromobenzonitrile

A solution of 2-bromo-4-((1,3-dioxoisoindolin-2-yl)methyl)benzonitrile (crude product) and hydrazine hydrate (38 mL) in EtOH (500 mL) was heated at reflux for 2 hours. The reaction mixture was cooled, filtered, and concentrated under reduced pressure to afford a crude 4-(aminomethyl)-2-bromobenzonitrile as yellow solid, which was used without further purification. MS (ESI) m/z: 211 [M+H]$^+$.

Step C. 2-Bromo-4-((3-nitropyridin-2-ylamino)methyl)benzonitrile

To a solution of 4-(aminomethyl)-2-bromobenzonitrile in dry t-BuOH (200 mL) at 25° C., was added sodium (6.3 g) in several small portions. After the mixture was stirred at 50° C. for 0.5 hour, 2-chloro-3-nitropyridine (14 g, 89 mmol) was added in several portions. The reaction mixture was heated at reflux for 3 hours and concentrated under reduced pressure. The residue was purified by silica gel chromatography using Petroleum Ether:EtOAc (10:1 to 5:1) as eluting solvents to afford 2-bromo-4-((3-nitropyridin-2-ylamino)methyl)benzonitrile as a red solid (7.5 g, 27% for 3 steps). MS (ESI) m/z: 332 [M+H]$^+$.

Step D. 4-((3-Aminopyridin-2-ylamino)methyl)-2-bromobenzonitrile

To a solution of 2-bromo-4-((3-nitropyridin-2-ylamino)methyl)benzonitrile (7.5 g, 23 mmol) in EtOH (50 mL) and H$_2$O (30 mL) at reflux, was added iron powder (3.8 g, 69 mmol) and NH$_4$Cl (12 g, 222 mmol). The mixture was heated one more hour under reflux before cooling to 25° C. and filtration through a celite cake. After concentration under reduced pressure, the crude 4-((3-aminopyridin-2-ylamino)methyl)-2-bromobenzonitrile was obtained and used in the next step without further purification. MS (ESI) m/z: 303 [M+H]$^+$.

Step E. 4-((3H-[1,2,3]Triazolo[4,5-b]pyridin-3-yl)methyl)-2-bromobenzonitrile A solution of 4-((3-aminopyridin-2-ylamino)methyl)-2-bromobenzonitrile in concentrated HCl (50 mL) in an ice bath was treated with sodium nitrite (1.7 g, 24 mmol). The mixture was stirred at 5° C. for 1 hour before adding an ammonium hydroxide solution until pH >7. After extraction with EtOAc (50 mL*3), the combined organic extracts were concentrated under reduced pressure. The residue was purified by silica gel chromatography Petroleum Ether:EtOAc (10:1 to 5:1) to afford 4-((3H-[1,2,3]triazolo[4,5-b]pyridin-3-yl)methyl)-2-bromobenzonitrile as a yellow solid (1.5 g, 21% for two steps). MS (ESI) m/z: 314 [M+H]$^+$.

Step F. 5'-((3H-[1,2,3]Triazolo[4,5-b]pyridin-3-yl)methyl)-2'-cyano-[1, 1'-biphenyl]-4-yl sulfamate The procedures described in Example 2 steps C, D and E were repeated with 4-((3H-[1,2,3]triazolo[4,5-b]pyridin-3-yl)methyl)-2-bromobenzonitrile to obtain the title compound as white solid (55 mg, 13%). $^1$H NMR (500 MHz, DMSO-d$_6$) δ (ppm) 8.80 (dd, J$_1$=1.5 Hz, J$_2$=4.5 Hz, 1H), 8.63 (dd, J$_1$=2 Hz, J$_2$=8.5 Hz, 1H), 8.17 (brs, 2H), 7.95 (d, J=8.5 Hz, 1H), 7.66 (d, J=5 Hz, 2H), 7.65 (s, 1H), 7.47 (dd, J$_1$=1.5 Hz, J$_2$=8 Hz, 1H), 7.45 (d, J=5 Hz, 2H), 7.43 (d, J=5 Hz, 1H), 6.47 (s, 2H). MS (ESI) m/z: 407 [M+H]$^+$.

Example 9

4-(2-((1H-Benzo[d]imidazol-1-yl)methyl)-5-cyanopyrimidin-4-yl)phenyl sulfamate

Step A. 2-(1H-Benzo[d]imidazol-1-yl)acetonitrile

A mixture of 1H-benzo[d]imidazole (5.9 g, 50 mmol), ClCH$_2$CN (4.55 g, 60 mmol), and K$_2$CO$_3$ (13.8 g, 100 mmol) in MeCN (50 mL) was heated at 40° C. for 3 hours. The reaction mixture was cooled to 25° C., concentrated under reduced pressure and purified by silica gel chromatography using CH$_2$Cl$_2$:MeOH (150:1) as eluting solvents to afford 2-(1H-benzo[d]imidazol-1-yl)acetonitrile as a gray solid (5.5 g, 70%). MS (ESI) m/z: 158 [M+H]$^+$.

Step B. 2-(1H-Benzo[d]imidazol-1-yl)acetimidamide

A mixture of 2-(1H-benzo[d]imidazol-1-yl)acetonitrile (1 g, 6.37 mmol) and MeONa (0.034 g, 0.64 mmol) in THF (20 mL) and MeOH (20 mL) was heated at 45° C. overnight. After the reaction mixture was cooled to 25° C., NH$_4$Cl (0.68 g, 12.74 mmol) was added followed by MeOH (10 mL). The mixture was stirred at 80° C. for 4 hours, quenched by H$_2$O (5 mL), concentrated under reduced pressure, and recrystallized by H$_2$O and EtOH to afford 2-(1H-benzo[d]imidazol-1-yl)acetimidamide as a gray solid (800 mg, 72%). MS (ESI) m/z: 175 [M+H]$^+$.

Step C. (E)-3-(Dimethylamino)-2-(4-methoxybenzoyl)acrylonitrile

A solution of 3-(4-methoxyphenyl)-3-oxopropanenitrile (1.6 g, 9.1 mmol) and N,N-dimethylformamide dimethylacetal (1.59 g, 11 mmol) in toluene (15 mL) was stirred at 50° C. for 1 hour. The reaction mixture was cooled and concentrated to afford the crude (E)-3-(dimethylamino)-2-(4-methoxybenzoyl)acrylonitrile as a yellow solid (1.8 g, 86%). MS (ESI) m/z: 231 [M+H]$^+$.

Step D. 2-((1H-Benzo[d]imidazol-1-yl)methyl)-4-(4-methoxyphenyl)pyrimidine-5-carbonitrile A mixture of (E)-3-(dimethylamino)-2-(4-methoxybenzoyl)acrylonitrile (230 mg, 1 mmol), 2-(1H-benzo[d]imidazol-1-yl)acetimidamide (174 mg, 1 mmol), and DIPEA (387 mg, 3 mmol) in 2-pentanol (10 mL) was heated at 130° C. for 3 hours. The reaction mixture was cooled, concentrated under reduced pressure and purified by silica gel chromatography using CH$_2$Cl$_2$:MeOH (80:1) as eluting solvents to afford 2-((1H-benzo[d]imidazol-1-yl)methyl)-4-(4-methoxyphenyl)pyrimidine-5-carbonitrile as a yellow solid (300 g, 73%). MS (ESI) m/z: 342 [M+H]$^+$.

Step E. 4-(2-((1H-Benzo[d]imidazol-1-yl)methyl)-5-cyanopyrimidin-4-yl)phenyl sulfamate The procedures described in Example 2 steps D and E were repeated using 2-((1H-benzo[d]imidazol-1-yl)methyl)-4-(4-methoxyphenyl)pyrimidine-5-carbonitrile (230 mg) to obtain the title compound as a white solid (34 mg, 12%). $^1$HNMR (500 MHz, DMSO-d$_6$) δ (ppm) 9.33 (s, 1H), 8.37 (s, 1H), 8.22 (s, 2H), 8.00 (d, J=9 Hz, 2H), 7.69-7.68 (m, 1H), 7.52-7.48 (m, 3H), 7.22-7.21 (m, 2H), 5.93 (s, 2H); MS (ESI) m/z: 407 [M+H]$^+$.

Example 10

4-(6-((1H-Benzo[d]imidazol-1-yl)methyl)-3-cyano-pyridin-2-yl)phenyl sulfamate Step A. 6-(Bromomethyl)-2-chloronicotinonitrile A solution of 2-chloro-6-methylnicotinonitrile (42 g, 276 mmol), benzoyl peroxide (6.7 g, 27.6 mmol), and NBS (62 g, 276.3 mmol) in $CCl_4$ (800 mL) was stirred for 4 hours at 85° C. The reaction mixture was cooled to 25° C., filtered, and concentrated under reduced pressure. The residue was recrystallized from Petroleum Ether:EtOAc (10:1) to afford 6-(bromomethyl)-2-chloronicotinonitrile as a white solid (19 g, 30%). MS (ESI) m/z: 231 [M+H]$^+$.

Step B. 6-((1H-Benzo[d]imidazol-1-yl)methyl)-2-chloronicotinonitrile

A solution of 6-(bromomethyl)-2-chloronicotinonitrile (2.32 g, 10 mmol), 1H-benzo[d]imidazole (1.2 g, 10 mmol), and $K_2CO_3$ (4 g, 30 mmol) in $CH_3CN$ (150 mL) was stirred at 25° C. for 20 hours. The reaction mixture was cooled, filtered, and concentrated under reduced pressure. The residue was purified by silica gel chromatography using MeOH:$CH_2Cl_2$ (1:200-1:30) to afford 6-((1H-benzo[d]imidazol-1-yl)methyl)-2-chloronicotinonitrile as a yellow oil (300 mg, 11%). MS (ESI) m/z: 269 [M+H]$^+$.

Step C. 4-(6-((1H-Benzo[d]imidazol-1-yl)methyl)-3-cyanopyridin-2-yl)phenyl sulfamate The procedures described in Example 2 steps C, D and E were repeated using 6-(bromomethyl)-2-chloronicotinonitrile to obtain the title compound as a white solid (80 mg, 20%). $^1$H NMR (500 MHz, DMSO-d$_6$) δ (ppm) 8.42-8.41 (m, 2H), 8.16 (s, 1H), 7.88-7.86 (m, 2H), 7.69-7.67 (m, 2H), 7.56-7.54 (m, 1H), 7.45-7.40 (m, 3H), 7.24-7.21 (m, 2H), 5.78 (s, 2H); MS (ESI) m/z: 406 [M+H]$^+$.

Example 11

5'-(1H-Benzo[d][1,2,3]triazol-1-ylamino)-2'-cyano-biphenyl-4-yl sulfamate

Step A. 1H-Benzo[d][1,2,3]triazol-1-amine

To a solution of benzotriazole (5 g, 42.01 mmol) and potassium hydroxide (11.76 g, 0.21 mol) in water (50 mL) was added hydroxylamine-O-sulfonic acid (9.49 g, 84.02 mmol) in several portions and the temperature of the reaction mixture was kept below 50° C. After the addition, the mixture was stirred at room temperature for 2 hours. The resulting precipitate was removed by filtration and washed thoroughly with EtOAc. The filtrate was concentrated under reduced pressure. The residue was purified by silica gel chromatography using Petroleum Ether:EtOAc (300:1) as eluting solvents to afford 1H-benzo[d][1,2,3]triazol-1-amine as a white solid (1.52 g, 27%). MS (ESI) m/z: 135 [M+H]$^+$.

Step B. 5'-(1H-Benzo[d][1,2,3]triazol-1-ylamino)-2'-cyanobiphenyl-4-yl sulfamate The procedures described in Example 2 Step C, D and E were repeated using 1H-benzo[d][1,2,3]triazol-1-amine to obtain the title compound as a white solid (60 mg). $^1$H NMR (500 MHz, DMSO-d$_6$) δ (ppm) 11.19 (s, 1H), 8.18 (d, 1H), 8.12 (s, 2H), 7.79 (d, 1H), 7.66 (m, 2H), 7.57 (m, 2H), 7.52 (m, 1H), 7.40 (m, 2H), 6.58 (d, 1H), 6.48 (dd, 1H); MS (ESI) m/z: 407 [M+H]$^+$.

Example 12

5'-((3H-Imidazo[4,5-b]pyridin-3-yl)methyl)-2'-cyano-[1,1'-biphenyl]-4-yl sulfamate Step A. 4-((3H-Imidazo[4,5-b]pyridin-3-yl)methyl)-2-bromobenzonitrile A mixture of 3H-imidazo[4,5-b]pyridine (835 mg, 7 mmol), 2-bromo-4-(bromomethyl)benzonitrile (410 mg 3.4 mmol), $K_2CO_3$ (938 mg, 6.8 mmol), and KI (113 mg, 0.68 mmol) in $CH_3CN$ was stirred at room temperature for 12 hours. The reaction mixture was quenched with EtOAc, filtered, and concentrated under reduced pressure. The residue was purified by silica gel chromatography using $CH_2Cl_2$:methanol (30:1) as eluting solvents to afford 4-((3H-imidazo[4,5-b]pyridin-3-yl)methyl)-2-bromobenzonitrile as a white solid (1.14 g, 52%). MS (ESI) m/z: 313 [M+H]$^+$.

Step B. 5'-((3H-Imidazo[4,5-b]pyridin-3-yl)methyl)-2'-cyano-[1,1'-biphenyl]-4-yl sulfamate The procedures described in Example 2 steps C, D and E were repeated using 4-((3H-imidazo[4,5-b]pyridin-3-yl)methyl)-2-bromobenzonitrile to obtain the title compound as a yellow solid (40 mg, 10%). $^1$H NMR (500 MHz, DMSO-d) δ (ppm) 9.68 (s, 1H), 8.37 (d, J=6.5 Hz, 1H), 8.13-8.11 (m, 3H), 7.94 (d, J=5 Hz, 1H), 7.65-7.61 (m, 3H), 7.47-7.42 (m, 3H), 7.31 (m, 1H), 5.67 (s, 2H); MS (ESI) m/z: 406 [M+H]$^+$.

Example 13

5'-((1H-Benzo[d][1,2,3]triazol-1-yl)(methyl)amino)-2'-cyanobiphenyl-4-yl sulfamate Step A. 4-((1H-Benzo[d][1,2,3]triazol-1-yl)(methyl)amino)-2-bromobenzonitrile The procedure described in Example 5 step A was repeated using 4-(1H-benzo[d][1,2,3]triazol-1-ylamino)-2-bromobenzonitrile (563 mg, 1.79 mmol) to obtain the title compound as a white solid (570 mg, 97%). MS (ESI) m/z: 328 [M+H]$^+$.

Step B. 5'-((1H-Benzo[d][1,2,3]triazol-1-yl)(methyl)amino)-2'-cyanobiphenyl-4-yl sulfamate The procedures described in Example 2 steps C, D and E were repeated using 4-((1H-benzo[d][1,2,3]triazol-1-yl)(methyl)amino)-2-bromobenzonitrile to obtain the title compound as a white solid (31 mg). $^1$H NMR (500 MHz, CDCl$_3$) δ (ppm) 8.17 (d, 1H), 7.58-7.64 (m, 2H), 7.47-7.51 (m, 4H), 7.38-7.40 (m, 2H), 6.52 (m, 2H), 5.04 (s, 2H), 3.70 (s, 3H); MS (ESI) m/z: 421 [M+H]$^+$.

Example 14

4-(6-((3H-Imidazo[4,5-b]pyridin-3-yl)methyl)-3-cyanopyridin-2-yl)phenyl sulfamate Step A. 6-((3H-Imidazo[4,5-b]pyridin-3-yl)methyl)-2-chloronicotinonitrile A solution of 6-(bromomethyl)-2-chloronicotinonitrile (2.32 g, 10 mmol) [Example 10 step A], 3H-imidazo[4,5- b]pyridine (1.3 g, 11 mmol), and $K_2CO_3$ (4 g, 30 mmol) in $CH_3CN$ (40 mL) was stirred at 25° C. for 20 hours. The reaction mixture was cooled to 25° C., filtered and concentrated under reduced pressure. The residue was purified by silica gel chromatography using Petroleum Ether:EtOAc (5:1-1:1) to afford the title compound as a yellow oil (600 mg, 30%). MS (ESI) m/z: 270 [M+H]$^+$.

Step B. 4-(6-((3H-Imidazo[4,5-b]pyridin-3-yl)methyl)-3-cyanopyridin-2-yl)phenyl sulfamate The procedures described in Example 2 steps C, D and E were repeated using 6-((3H-imidazo[4,5-b]pyridin-3-yl)methyl)-2-chloronicotinonitrile to obtain the title compound as white solid (105 mg, 47%). $^1$H NMR (500 MHz, DMSO-$d_6$) δ (ppm) 8.64 (s, 1H), 8.41 (d, J=8.0 Hz, 1H), 8.33-8.32 (m, 1H), 8.14-8.12 (m, 1H), 7.82-7.80 (m, 4H), 7.45 (d, J=8.5 Hz, 1H), 7.42-7.40 (m, 3H), 7.32-7.30 (m, 1H), 5.80 (s, 2H); MS (ESI) m/z: 407 [M+H]$^+$.

Example 15

4-(2-(1H-Benzo[d]imidazol-1-ylamino)-5-cyanopyrimidin-4-yl)phenyl sulfamate

Step A. 2-Imino-4-(4-methoxyphenyl)-1,2-dihydropyrimidine-5-carbonitrile

A solution of (E)-3-(dimethylamino)-2-(4-methoxybenzoyl)acrylonitrile (500 mg, 2.2 mmol), guanidine hydrochloride (627 mg, 6.6 mmol), and $K_2CO_3$ (1.82 g, 13.2 mmol) in DMF (15 mL) was stirred at 70° C. for 20 hours. The reaction mixture was quenched with water (20 mL) and filtered. The solid was dried to afford the 2-imino-4-(4-methoxyphenyl)-1,2-dihydropyrimidine-5-carbonitrile as a yellow solid (400 mg, 80%). MS (ESI) m/z: 227 [M+H]$^+$.

Step B. 2-Hydroxy-4-(4-methoxyphenyl)pyrimidine-5-carbonitrile

A solution of 2-imino-4-(4-methoxyphenyl)-1,2-dihydropyrimidine-5-carbonitrile (2.4 g, 10.6 mmol) in AcOH (30 mL) was heated to 70° C., then $NaNO_2$ (5.4 g, 31.8 mmol) in water (10 mL) was added slowly. The mixture was stirred at 70° C. for 20 hours and then quenched with water (20 mL), extracted with EtOAC (200 mL×3), washed with brine and dried ($Na_2SO_4$). After filtration and evaporation, the residue was crystallized in EtOAc to afford 2-hydroxy-4-(4-methoxyphenyl)pyrimidine-5-carbonitrile as a yellow solid (1.9 g, 79%). MS (ESI) m/z: 228 [M+H]$^+$.

Step C. 2-Chloro-4-(4-methoxyphenyl)pyrimidine-5-carbonitrile

A solution of 2-hydroxy-4-(4-methoxyphenyl)pyrimidine-5-carbonitrile (1.6 g, 7 mmol) in $POCl_3$ (30 mL) was heated at 100° C. for 20 hours, then quenched with ice-water slowly and adjusted to pH=4. The mixture was filtered to afford 2-chloro-4-(4-methoxyphenyl) pyrimidine-5-carbonitrile as a yellow solid (1.1 g, 65%). MS (ESI) m/z: 246 [M+H]$^+$.

Step D. 2-(1H-Benzo[d]imidazol-1-ylamino)-4-(4-methoxyphenyl)pyrimidine-5-carbonitrile A solution of 2-chloro-4-(4-methoxyphenyl)pyrimidine-5-carbonitrile (900 mg, 3.7 mmol), 1H-benzo[d]imidazol-1-amine (532 mg, 4 mmol), $Cs_2CO_3$ (2.4 g, 7.4 mmol), $Pd_2(dba)_3$ (200 mg, 0.185 mmol) and Xantphos (384 mg, 0.29 mmol) in 1,4-dioxane (20 mL) under $N_2$ was heated at 90° C. for 20 hours. After cooling to 25° C., the mixture was evaporated under reduced pressure and the residue purified by silica gel chromatography using Petroleum Ether:EtOAc (10:1-1:1) to afford 2-(1H-benzo[d]imidazol-1-ylamino)-4-(4-methoxyphenyl) pyrimidine-5-carbonitrile as a yellow solid (270 mg, 21%). MS (ESI) m/z: 343 [M+H]$^+$.

Step E. 4-(2-(1H-Benzo[d]imidazol-1-ylamino)-5-cyanopyrimidin-4-yl)phenyl sulfamate The procedures described in Example 2 steps D and E were repeated using starting with 2-(1H-benzo[d]imidazol-1-ylamino)-4-(4-methoxyphenyl)pyrimidine-5-carbonitrile (120 mg) to obtain the title compound as a white solid (27 mg, 18%). $^1$H NMR (500 MHz, $CD_3OD$) δ (ppm) 8.85 (brs, 1H), 8.34 (s, 1H), 7.77-7.75 (m, 2H), 7.65-7.60 (m, 1H), 7.50-7.36 (m, 5H); MS (ESI) m/z: 408 [M+H]$^+$.

Example 16

4-(2-((1H-Benzo[d]imidazol-1-yl)(methyl)amino)-5-cyanopyrimidin-4-yl)phenyl sulfamate Step A. 2-((1H-Benzo[d]imidazol-1-yl)(methyl)amino)-4-(4-methoxyphenyl)pyrimidine-5-carbonitrile The procedure described in Example 5 step A was repeated using 2-(1H-benzo[d]imidazol-1-ylamino)-4-(4-methoxyphenyl)pyrimidine-5-carbonitrile (240 mg) and iodomethane, the title compound was obtained as a yellow solid (210 mg, 84%). MS (ESI) m/z: 357 [M+H]$^+$.

Step B. 4-(2-((1H-Benzo[d]imidazol-1-yl)(methyl)amino)-5-cyanopyrimidin-4-yl)phenyl sulfamate The procedures described in Example 2 steps D and E were repeated using 2-((1H-benzo[d]imidazol-1-yl)(methyl)amino)-4-(4-methoxyphenyl)pyrimidine-5-carbonitrile (110 mg) to obtain the title compound as a white solid (17 mg). $^1$H NMR (500 MHz, DMSO-$d_6$) δ (ppm) 8.90 (brs, 1H), 8.54 (s, 1H), 8.25 (brs, 3H), 7.77-7.29 (m, 7H), 3.84 (s, 3H); MS (ESI) m/z: 422 [M+H]$^+$.

Example 17

4-(2-((1H-Benzo[d]imidazol-1-yl)methyl)-5-cyanopyridin-4-yl)phenyl sulfamate

Step A. 4-Chloro-6-methylnicotinonitrile

A solution of 4-hydroxy-6-methylnicotinamide (5 g, 32 mmol) and $PCl_5$ (10.3 g, 50 mmol) in $POCl_3$ (50 mL) was heated to reflux for 20 hours. The reaction mixture was cooled to 25° C. and concentrated under reduced pressure. The residue was purified by silica gel chromatography using Petroleum ether:EtOAc (3:1) as eluting solvents to afford 4-chloro-6-methylnicotinonitrile as white solid (3.2 g, 64%). MS (ESI) m/z: 153 [M+H]+

Step B. 6-(Bromomethyl)-4-chloronicotinonitrile

A mixture of 4-chloro-6-methylnicotinonitrile (3.2 g, 21 mmol), NBS (3.7 g, 21 mmol), and benzoyl peroxide (968 mg, 4 mmol) in CCl$_4$ (50 mL) under nitrogen was heated to reflux for 12 hours. The mixture was cooled to 25° C., filtered and the filtrate was concentrated under reduced pressure. The residue was use in the next step without further purification. MS (ESI) m/z: 231 [M+H]$^+$.

Step C. 4-((1H-Benzo[d]imidazol-1-yl)methyl)-2-chlorobenzonitrile

A mixture of 6-(bromomethyl)-4-chloronicotinonitrile (1.8 g, 7.8 mmol), 1H-imidazo[4,5-c]pyridine (929 mg 7.8 mmol), K$_2$CO$_3$ (2 g, 15.6 mmol), and KI (266 mg, 1.6 mmol) in CH$_3$CN was stirred at 25° C. for 12 hours. The reaction mixture was diluted with EtOAc, filtered, and concentrated under reduced pressure. The residue was purified by silica gel chromatography using CH$_2$Cl$_2$:methanol (30:1) as eluting solvents to afford 4-((1H-benzo[d]imidazol-1-yl)methyl)-2-chloro-benzonitrile as light yellow solid (833 mg, 40%). MS (ESI) m/z: 268 [M+H]$^+$.

Step D. 4-(2-((1H-Benzo[d]imidazol-1-yl)methyl)-5-cyanopyridin-4-yl)phenyl sulfamate The procedures described in Example 2 steps C, D and E were repeated using 4-((1H-benzo[d]imidazol-1-yl)methyl)-2-chlorobenzonitrile to obtain the title compound as light yellow solid (40 mg, 10%). $^1$H NMR (500 MHz, DMSO-d) δ (ppm) 9.04 (s, 1H), 8.40 (s, 1H), 8.19 (s, 2H), 7.78-7.56 (m, 2H), 7.73 (m, 1H), 7.67 (m, 1H), 7.54 (m, 1H), 7.50-7.48 (m, 2H), 7.21-7.20 (m, 2H), 5.76 (s, 2H); MS (ESI) m/z: 406 [M+H]$^+$.

Example 18

5'-((1H-Benzo[d]imidazol-1-yl)methyl)-2'-cyano-3-(methylthio)-[1,1'-biphenyl]-4-yl sulfamate Step A. (5-Bromo-2-methoxyphenyl)(methyl)sulfane and (4-Bromo-2-methoxyphenyl)(methyl)sulfane To a solution of 2-methylthioanisole (2 g, 13 mmol) in CH$_2$Cl$_2$ (50 mL) was added powdered Fe (0.73 g, 1.3 mmol), followed by a dropwise addition of bromine (2.1 g, 13 mmol). After stirred at room temperature for 30 minutes, the starting material has been consumed. The excess bromine was quenched by adding a saturated aqueous solution of NaHSO$_3$ and the mixture was stirred for several minutes. The CH$_2$Cl$_2$ layer was separated, and the aqueous phase extracted with CH$_2$Cl$_2$. The combined CH$_2$Cl$_2$ extracts were dried over MgSO$_4$, filtered, and concentrated under reduced pressure. The residue was purified by silica gel chromatograph using Petroleum Ether to afford a mixture of (5-bromo-2-methoxyphenyl)(methyl)sulfane and (4-bromo-2-methoxyphenyl)(methyl)sulfane as a yellow oil. (1.2 g, 40%). MS (ESI) m/z: 234 [M+H]$^+$.

Step B. 2-(4-Methoxy-3-(methylthio)phenyl)-4,4,5,5-tetramethyl-1,3,2-dioxaborolane and 2-(3-Methoxy-4-(methylthio)phenyl)-4,4,5,5-tetra methyl-1,3,2-dioxaborolane A mixture of (5-bromo-2-methoxyphenyl)(methyl)sulfane and (4-bromo-2-methoxyphenyl)(methyl)sulfane (1100 mg, 4.72 mmol), 4,4,4',4',5,5,5',5'-octamethyl-2,2'-bi(1,3,2-dioxaborolane) (1439 mg, 5.66 mmol), KOAc (925 mg, 9.44 mmol) and Pd(dppf)Cl$_2$ (193 mg, 0.24 mmol) in 1,4-dioxane (50 mL) and DMSO (2 mL) was purged with nitrogen and heated at 90° C. for 14 hours. The reaction mixture was concentrated under reduced pressure. The residue was purified by silica gel chromatography using Petroleum Ether as eluting solvents to afford a mixture of 2-(4-methoxy-3-(methylthio)phenyl)-4,4,5,5-tetramethyl-1,3,2-dioxaborolane and 2-(3-methoxy-4-(methylthio)phenyl)-4,4,5,5-tetramethyl-1,3,2-dioxaborolane as a white solid (1196 mg, 90%). MS (ESI) m/z: 281 [M+H]$^+$.

Step C. 5-((1H-Benzo[d]imidazol-1-yl)methyl)-4'-methoxy-3'-(methylthio)-[1,1'-biphenyl]-2-carbonitrile and 5-((1H-benzo[d]imidazol-1-yl)methyl)-3'-methoxy-4'-(methylthio)-[1,1'-biphenyl]-2-carbonitrile A mixture of 4-((1H-benzo[d]imidazol-1-yl)methyl)-2-bromobenzonitrile (312 mg, 1 mmol), 2-(4-methoxy-3-(methylthio)phenyl)-4,4,5,5-tetra methyl-1,3,2-dioxaborolane/2-(3-methoxy-4-(methylthio)phenyl)-4,4,5,5-tetramethyl-1,3,2-dioxaborolane (290 mg, 1.05 mmol), K$_2$CO$_3$ (276 mg, 2 mmol), and Pd(PPh$_3$)$_4$ (58 mg, 0.05 mmol) in 1,4-dioxane (6 mL) and H$_2$O (1.2 mL) was purged with nitrogen and heated at 90° C. for 14 hours. The reaction mixture was concentrated under reduced pressure. The residue was purified by silica gel chromatography using CH$_2$Cl$_2$:MeOH (50:1) as eluting solvents to afford a mixture of 5-((1H-benzo[d]imidazol-1-yl)methyl)-4'-methoxy-3'-(methylthio)-[1,1'-biphenyl]-2-carbonitrile and 5-((1H-benzo[d]imidazol-1-yl)methyl)-3'-methoxy-4'-(methylthio)-[1,1'-biphenyl]-2-carbonitrile as a yellow solid (349 mg, 90.6%). MS (ESI) m/z: 386 [M+H]$^+$.

Step D. 5-((1H-Benzo[d]imidazol-1-yl)methyl)-4'-hydroxy-3'-(methylthio)-[1,1'-biphenyl]-2-carbonitrile and 5-((1H-Benzo[d]imidazol-1-yl)methyl)-3'-hydroxy-4'-(methylthio)-[1,1'-biphenyl]-2-carbonitrile A mixture of 5-((1H-benzo[d]imidazol-1-yl)methyl)-4'-methoxy-3'-(methylthio)-[1,1'-biphenyl]-2-carbonitrile and 5-((1H-benzo[d]imidazol-1-yl)methyl)-3'-methoxy-4'-(methylthio)-[1,1'-biphenyl]-2-carbonitrile (349 mg, 0.91 mmol) in CH$_2$Cl$_2$ (40 mL) was cooled to −78° C. during the addition of BBr$_3$ (2 mL, 22 mmol). The reaction mixture was stirred at 23° C. for 4 hours before being poured into water where pH was adjusted to 7 with dry NaHCO$_3$. The organic layer was decanted and the aqueous layer was extracted with CH$_2$Cl$_2$ (40 mL×2). The organic solutions were collected, dried over anhydrous sodium sulfate, filtered and evaporated under reduced pressure. The residue was purified by silica gel column using Petroleum Ether: EtOAc (1:1) and by preparative HPLC to afford 5-((1H-benzo[d]imidazol-1-yl) methyl)-4'-hydroxy-3'-(methylthio)-[1,1'-biphenyl]-2-carbonitrile as a white solid (120 mg, 35.5%). $^1$H NMR (500 MHz, DMSO-d$_6$) δ (ppm) 10.39 (s, 1H), 8.47 (s, 1H), 7.89-7.88 (d, J=8.0 Hz, 1H), 7.70-7.67 (d, J=7.0 Hz, 1H), 7.56-7.55 (d, J=7.0 Hz, 1H), 7.52 (s, 1H), 7.38-7.36 (d, J=8.0 Hz, 1H), 7.23-7.20 (m, 3H), 6.96-6.94 (d, J=8.0 Hz, 1H), 6.93 (s, 1H), 5.66 (s, 2H), 2.41 (s, 3H); MS (ESI) m/z: 372 [M+H]+ and 5-((1H-benzo[d]imidazol-1-yl)methyl)-3'-hydroxy-4'-(methylthio)-[1,1'-biphenyl]-2-carbonitrile as a white solid (70 mg, 20.7%). MS (ESI) m/z: 372 [M+H]$^+$.

Step E. 5'-((1H-Benzo[d]imidazol-1-yl)methyl)-2'-cyano-3-(methylthio)-[1,1'-biphenyl]-4-yl sulfamate A mixture of 5-((1H-benzo[d]imidazol-1-yl)methyl)-4'-hydroxy-3'-(methylthio)-[1,1'-biphenyl]-2-carbonitrile (100 mg, 0.27 mmol) and sulfamoyl chloride (310 mg, 2.7 mmol) [see Example 1 step E] in DMA (5 mL) was stirred overnight at 23° C. The solution was concentrated under reduced pressure and the residue was purified by preparative HPLC to afford 5'-((1H-benzo[d]imidazol-1-yl)methyl)-2'-cyano-3-(methylthio)-[1,1'-biphenyl]-4-yl sulfamate as a white solid (40 mg, 33%). $^1$H NMR (500 MHz, DMSO-d$_6$) δ (ppm) 8.48 (s, 1H), 8.28 (s, 2H), 7.95-7.93 (d, J=8.0 Hz, 1H), 7.68-7.65 (m, 2H), 7.59-7.57 (d, J=6.9 Hz, 1H), 7.51-7.49 (d, J=8.4 Hz, 1H), 7.45-7.42 (m, 2H), 7.38-7.36 (d, J=8.4 Hz, 1H), 7.25-7.18 (m, 2H), 5.67 (s, 2H), 2.47 (s, 3H); MS (ESI) m/z: 451 [M+H]$^+$.

Example 19

5'-((1H-benzo[d]imidazol-1-yl)methyl)-2'-cyano-4-(methylthio)-[1,1'-biphenyl]-3-yl sulfamate Compound of Example 19 was prepared in the same manner as described for compound of Example 18 starting from 5-((1H-benzo[d]imidazol-1-yl)methyl)-3'-hydroxy-4'-(methylthio)-[1,1'-biphenyl]-2-carbonitrile. The title compound was obtained as a white solid (16 mg, 18.8%). $^1$H NMR (500 MHz, CD$_3$OD) δ (ppm) 8.37 (s, 1H), 7.83-7.81 (d, J=8.0 Hz, 1H), 7.73-7.71 (m, 1H), 7.61 (s, 1H), 7.55 (s, 1H), 7.50-7.45 (m, 3H), 7.34-7.30 (m, 3H), 5.69 (s, 2H), 2.53 (s, 3H); MS (ESI) m/z: 451 [M+H]$^+$.

Example 20

5'-((1H-Benzo[d]imidazol-1-yl)amino)-2'-cyano-3-(methylthio)-[1,1'-biphenyl]-4-yl sulfamate Compound of Example 20 was prepared in the same manner as described for compound of Example 18 starting from a mixture of 2-(4-methoxy-3-(methylthio)phenyl)-4,4,5,5-tetramethyl-1,3,2-dioxaborolane/2-(3-methoxy-4-(methylthio)phenyl)-4,4,5,5-tetramethyl-1,3,2-dioxaborolane and 4-(1H-benzo[d]imidazol-1-ylamino)-2-bromobenzonitrile [Example 2 step B]. The title compound was obtained as a white solid (34 mg, 23%). $^1$H NMR (500 MHz, DMSO-d$_6$) δ (ppm) 10.42 (s, 1H), 8.46 (s, 1H), 8.24 (s, 2H), 7.78-7.77 (d, J=8.5 Hz, 2H), 7.46-7.45 (d, J=8.4 Hz, 1H), 7.36 (s, 1H), 7.32-7.28 (m, 4H), 6.58 (s, 1H), 6.52-6.51 (d, J=9.5 Hz, 1H), 2.43 (s, 3H); MS (ESI) m/z: 452 [M+H]$^+$.

Example 21

5'-((1H-Benzo[d]imidazol-1-yl)amino)-2'-cyano-4-(methylthio)-[1,1'-biphenyl]-3-yl sulfamate Compound of Example 21 was prepared in the same manner as described for compound of Example 19 starting from 5-((1H-benzo[d]imidazol-1-yl)amino)-3'-hydroxy-4'-(methylthio)-[1,1'-biphenyl]-2-carbonitrile. The title compound was obtained as white solid (25 mg). $^1$H NMR (500 MHz, DMSO-d$_6$) δ (ppm) 10.41 (s, 1H), 8.46 (s, 1H), 8.20 (s, 2H), 7.75-7.74 (d, J=8.7 Hz, 2H), 7.48 (s, 1H), 7.43-7.42 (m, 2H), 7.34-7.28 (m, 3H), 6.68 (s, 1H), 6.42-6.40 (d, J=8.2 Hz, 1H), 2.48 (s, 3H); MS (ESI) m/z: 452 [M+H]$^+$.

Example 22

4-(6-(1H-Benzo[d]imidazol-1-ylamino)-3-cyanopyridin-2-yl)phenyl sulfamate

Step A. 2-(4-Methoxyphenyl)nicotinonitrile

The procedure described in Example 1 step C was repeated using 2-chloronicotinonitrile (5 g) and 4-methoxyphenylboronic acid to obtain the title compound as a white solid (7.5 g, 95%). MS (ESI) m/z: 211 [M+H]$^+$.

Step B. 3-Cyano-2-(4-methoxyphenyl)pyridine 1-oxide

To a solution of 2-(4-methoxyphenyl)nicotinonitrile (8 g, 40 mmol) in CH$_2$Cl$_2$ (180 mL), at 0° C., was added m-CPBA (13.7 g, 80 mmol). The mixture was stirred at 25° C. for 20 hours before addition of solid Na$_2$S$_2$O$_3$ and further stirring for 10 minutes. The reaction mixture was quenched with water and extracted with EtOAc (3×200 mL). The organic solutions were collected and washed with a saturated aqueous solution of Na$_2$CO$_3$ then brine. After drying over MgSO$_4$, filtration and evaporation under reduced pressure, the residue was purified by silica gel chromatography using Petroleum Ether:EtOAc (50:1-10:1) to afford 3-cyano-2-(4-methoxyphenyl)pyridine 1-oxide as a white solid (7.5 g, 83%). MS (ESI) m/z: 227 [M+H]$^+$.

Step C. 6-Chloro-2-(4-methoxyphenyl)nicotinonitrile

A solution of 3-cyano-2-(4-methoxyphenyl)pyridine 1-oxide (7.5 g, 35.4 mmol) in POCl$_3$ (100 mL) was heated at 100° C. for 20 hours. Ice-water was slowly added to the reaction mixture followed by dry Na$_2$CO$_3$ until pH 8. After extraction with EtOAc (3×200 mL), the organic solutions were combined, dried over Na$_2$SO$_4$, filtered and were evaporated under reduced pressure. The residue was purified by silica gel chromatography using Petroleum Ether:EtOAc (70:1-20:1) to afford 6-chloro-2-(4-methoxyphenyl)nicotinonitrile as a white solid (2.1 g, 24.4%). MS (ESI) m/z: 345 [M+H]$^+$.

Step D. 6-(1H-Benzo[d]imidazol-1-ylamino)-2-(4-methoxyphenyl)nicotinonitrile

The procedure described in Example 2 Step B was repeated using 6-chloro-2-(4-methoxyphenyl)nicotinonitrile (750 mg) and 1H-benzo[d]imidazol-1-amine to afford the title compound as a white solid (780 mg, 75%). MS (ESI) m/z: 342 [M+H]$^+$.

Step E. 4-(6-(1H-Benzo[d]imidazol-1-ylamino)-3-cyanopyridin-2-yl)phenyl sulfamate The procedures described in Example 2 steps D and E were repeated using 6-(1H-benzo[d]imidazol-1-ylamino)-2-(4-methoxyphenyl)nicotinonitrile (190 mg) to afford the title compound as white solid (26 mg, 6%). $^1$H NMR (500 MHz, DMSO-d$_6$) δ (ppm) 11.10 (brs, 1H), 8.45 (s, 1H), 8.13-8.10 (m, 3H), 7.75-7.73 (m, 3H), 7.37-7.35 (m, 3H), 7.29-7.28 (m, 2H), 6.56 (brs, 1H); MS (ESI) m/z: 407 [M+H]$^+$.

Example 23

4-(6-((1H-Benzo[d]imidazol-1-yl)(methyl)amino)-3-cyanopyridin-2-yl)phenyl sulfamate Compound of Example 23 was prepared in the same manner as described for compound of Example 16 starting from 6-((1H-benzo[d]imidazol-1-yl)(methyl)amino)-2-(4-methoxyphenyl)nicotinonitrile. The title compound was obtained as a white solid (110 mg, 32%). $^1$H NMR (500 MHz, DMSO-d$_6$) δ (ppm) 8.61 (s, 1H), 8.17 (s, 2H), 8.06 (d, J=8.5 Hz, 1H), 7.94 (d, J=8.5 Hz, 2H), 7.81-7.80 (m, 1H), 7.46-7.41 (m, 3H), 7.34-7.32 (m, 2H), 6.18 (brs, 1H), 3.74 (s, 3H); MS (ESI) m/z: 421 [M+H]+.

Example 24

2'-Cyano-5'-((5,6-difluoro-1H-benzo[d]imidazol-1-yl)methyl)biphenyl-4-yl sulfamate Step A. 5,6-Difluoro-1H-benzo[d]imidazole A solution of 4,5-difluorobenzene-1,2-diamine (1.5 g, 10 mmol) in formic acid (20 mL) was heated at 80° C. for 12 hours. The reaction mixture was cooled to 25° C. and concentrated under reduced pressure. The residue was recrystallized form Petroleum ether:EtOAc (15:1) to afford 5,6-difluoro-1 H-benzo[d]imidazole as a yellow solid (1.4 g, 88%). MS (ESI) m/z: 155 [M+H]+.

Step B. 2-Bromo-4-((5,6-difluoro-1H-benzo[d]imidazol-1-yl)methyl)benzonitrile

A solution of 5,6-difluoro-1H-benzo[d]imidazole (1.4 g, 9 mmol), 2-bromo-4-(bromomethyl) benzonitrile (2.5 g, 9 mmol) [see Example 1 Step A] and $K_2CO_3$ (3.8 g, 27 mmol) in $CH_3CN$ (50 mL) was heated at 25° C. for 12 hours. The reaction mixture was cooled to 25° C., filtered and concentrated under reduced pressure. The residue was purified by silica gel chromatography using Petroleum ether:EtOAc (30:13:1) as eluting solvents to afford 2-bromo-4-((5,6-difluoro-1H-benzo[d]imidazol-1-yl)methyl)benzonitrile as a yellow solid (1.3 g, 39%). MS (ESI) m/z: 348 [M+H]+.

Step C. 2'-Cyano-5'-((5,6-difluoro-1H-benzo[d]imidazol-1-yl)methyl)biphenyl-4-yl sulfamate The procedures described in Example 1 steps C, D and E were repeated using 2-bromo-4-((5,6-difluoro-1H-benzo[d]imidazol-1-yl)methyl)benzonitrile to afford the title compound as yellow solid (38 mg, 27%). $^1$H NMR (500 MHz, DMSO-$d_6$) δ (ppm) 8.56 (s, 1H), 8.15 (brs, 2H), 7.95 (d, J=7.5 Hz, 1H), 7.83 (dd, $J_1$=2 Hz, $J_2$=10.5 Hz, 1H), 7.75 (d, J=10.5 Hz, 1H), 7.65 (d, J=6.5 Hz, 2H), 7.64 (s, 1H), 7.46 (s, 1H), 7.45 (d, J=6.5 Hz, 2H), 5.63 (s, 2H). MS (ESI) m/z: 441 [M+H]+.

Example 25

4-(2-((3H-Imidazo[4,5-b]pyridin-3-yl)methyl)-5-cyanopyrimidin-4-yl)phenyl sulfamate Step A.
2-(3H-Imidazo[4,5-b]pyridin-3-yl)acetonitrile A mixture of 1H-benzo[d]imidazole (3.57 g, 30 mmol), $ClCH_2CN$ (2.7 g, 36 mmol), $K_2CO_3$ (8.28 g, 60 mmol) and KI (0.99 g, 6 mmol) in MeCN (50 mL) was stirred at room temperature overnight. The reaction mixture was concentrated under reduced pressure. The residue was purified by silica gel chromatograph using $CH_2Cl_2$:MeOH (40:1) as eluting solvents to afford 2-(3H-imidazo[4,5-b]pyridin-3-yl)acetonitrile as a yellow solid (2.0 g, 40%). MS (ESI) m/z: 159 [M+H]+.

Step B.
2-(3H-Imidazo[4,5-b]pyridin-3-yl)acetimidamide

A mixture of 2-(3H-imidazo[4,5-b]pyridin-3-yl)acetonitrile (1.0 g, 6.33 mmol) and MeONa (0.034 g, 0.64 mmol) in THF (6 mL) and MeOH (15 mL) was heated at 45° C. overnight. After the reaction mixture was cooled, $NH_4Cl$ (0.68 g, 12.74 mmol) and MeOH (5 mL) were added. The mixture was stirred at 80° C. for 4 hours, quenched by $H_2O$ (5 mL), concentrated under reduced pressure, and recrystallized by $H_2O$ and EtOH to afford 2-(3H-imidazo[4,5-b]pyridin-3-yl)acetimidamide as a white solid (900 mg, 81%). MS (ESI) m/z: 176 [M+H]+.

Step C. 2-((3H-Imidazo[4,5-b]pyridin-3-yl)methyl)-4-(4-methoxyphenyl)pyrimidine-5-carbonitrile A mixture of 3-(dimethylamino)-2-(4-methoxybenzoyl)acrylonitrile (690 mg, 3 mmol), 2-(3H-imidazo[4,5-b]pyridin-3-yl)acetimidamide (525 mg, 3 mmol) [Example 9 Step C], and DIPEA (1161 mg, 9 mmol) in 2-pentanol (20 mL) was heated at 130° C. for 3 hours. The reaction mixture was cooled to 25° C., concentrated under reduced pressure and purified by silica gel chromatography using $CH_2Cl_2$:MeOH (80:1) as eluting solvents to afford 2-((3H-imidazo[4,5-b]pyridin-3-yl)methyl)-4-(4-methoxyphenyl)pyrimidine-5-carbonitrile as a yellow solid (600 mg, 58%). MS (ESI) m/z: 343 [M+H]+.

Step D. 4-(2-((3H-Imidazo[4,5-b]pyridin-3-yl)methyl)-5-cyanopyrimidin-4-yl)phenyl sulfamate The procedures described in Example 2 steps D and E were repeated using 2-((3H-imidazo[4,5-b]pyridin-3-yl)methyl)-4-(4-methoxyphenyl)pyrimidine-5-carbonitrile (150 mg) to afford the title compound as a white solid (60 mg, 32%). $^1$HNMR (500 MHz, DMSO-$d_6$) δ (ppm) 9.31 (s, 1H), 8.62 (d, J=6 Hz, 1H), 8.31-8.30 (m, 1H), 8.21 (s, 2H), 8.15-8.13 (m, 1H), 7.98-7.96 (m, 2H), 7.50-7.46 (m, 2H), 7.31-7.29 (m, 1H), 5.93 (s, 2H); MS (ESI) m/z: 408 [M+H]+

Example 26

4-(2-(1H-Benzo[d]imidazol-1-ylamino)-5-cyanopyridin-4-yl)phenyl sulfamate

Step A. 4-Chloro-5-iodopyridin-2-amine

A mixture of 4-chloropyridin-2-amine (2 g, 15.6 mmol) and N-iodosuccinimide (4.2 g, 18.7 mmol) in DMF (20 mL) was heated at 40° C. overnight. The reaction mixture was diluted by $H_2O$ (80 mL), extracted by EtOAc (40 mL*3). The combined organic solutions were dried over $Na_2SO_4$, filtered and concentrated under reduced pressure. The residue was purified by silica gel chromatography using Petroleum Ether:EtOAc (4:1) as eluting solvents to afford 4-chloro-5-iodopyridin-2-amine as a red solid (2.8 g, 70%). MS (ESI) m/z: 255 [M+H]+.

Step B.
2-(3H-Imidazo[4,5-b]pyridin-3-yl)acetimidamide

A mixture of 4-chloro-5-iodopyridin-2-amine (2.8 g, 11 mmol), $Pd(PPh_3)_4$ (1.9 g, 1.65 mmol), and $Zn(CN)_2$ (0.7 g, 6.05 mmol) in NMP (30 mL) was heated at 130° C. for 5 hours. The reaction mixture was cooled to 23° C., diluted by $H_2O$ (200 mL) and filtered. The solid was purified by silica gel chromatography using Petroleum Ether:EtOAc (3:1) as eluting solvents to afford 2-(3H-imidazo[4,5-b]pyridin-3-yl)acetimidamide as a yellow solid (1.18 g, 70%). MS (ESI) m/z: 154 [M+H]+.

Step C.
6-Amino-4-(4-methoxyphenyl)nicotinonitrile

A mixture of 2-(3H-imidazo[4,5-b]pyridin-3-yl)acetimidamide (1.18 g, 7.7 mmol), 4-methoxyphenylboronic acid (1.28 g, 8.4 mmol), Pd(OAc)$_2$ (0.093 g, 0.385 mmol), X-Phos (0.366 g, 0.77 mmol), and K$_3$PO$_4$ (4.89 g, 23.1 mmol) in toluene (40 mL) was heated at 85° C. overnight. The reaction mixture was cooled to 23° C., concentrated under reduced pressure and the residue purified by silica gel chromatography using Petroleum Ether:EtOAc (3:1) as eluting solvents to afford 6-amino-4-(4-methoxyphenyl)nicotinonitrile as a yellow solid (800 mg, 45%). MS (ESI) m/z: 226 [M+H]$^+$.

Step D.
6-Fluoro-4-(4-methoxyphenyl)nicotinonitrile

To a mixture of pyridine/HF (10 mL) in pyridine (10 mL) in an ice-bath was added 6-amino-4-(4-methoxyphenyl)nicotinonitrile (800 mg, 3.55 mmol). The mixture was stirred at 23° C. for 0.5 hour. After cooling down to −20° C., NaNO$_2$ (367 mg, 5.32 mmol) was added and stirred at room temperature for 2 hours. After quenching by addition of a saturated aqueous solution of K$_2$CO$_3$ and extraction by EtOAc (20 mL*3), the combined organic layers were dried over Na$_2$SO$_4$, filtered and concentrated under reduced pressure. The residue was purified by silica gel chromatography using Petroleum Ether:EtOAc (70:1) as eluting solvents to afford 6-fluoro-4-4-methoxyphenyl)nicotinonitrile as a white solid (400 mg, 49%). MS (ESI) m/z: 229 [M+H]$^+$.

Step E. 6-(1H-Benzo[d]imidazol-1-ylamino)-4-(4-methoxyphenyl)nicotinonitrile A mixture of 6-fluoro-4-(4-methoxyphenyl)nicotinonitrile (400 mg, 1.75 mmol), Cs$_2$CO$_3$ (1137 mg, 3.5 mmol), and 1H-benzo[d]imidazol-1-amine (279 mg, 2.1 mmol) in DMF (10 mL) was stirred at 70° C. overnight. After cooling at 23° C., the reaction mixture was then quenched by H$_2$O (80 mL) and extracted by EtOAc (30 mL*3). The combined organic layers were dried over Na$_2$SO$_4$, filtered and concentrated under reduced pressure. The residue was purified by silica gel chromatography using CH$_2$Cl$_2$:MeOH (100:1) as eluting solvents to afford 6-(1H-benzo[d]imidazol-1-ylamino)-4-(4-methoxyphenyl)nicotinonitrile as a yellow solid (300 mg, 52%). MS (ESI) m/z: 342 [M+H]$^+$.

Step F. 4-(2-(1H-Benzo[d]imidazol-1-ylamino)-5-cyanopyridin-4-yl)phenyl sulfamate The procedures described in Example 2 steps D and E were repeated using 6-(1H-benzo[d]imidazol-1-ylamino)-4-(4-methoxyphenyl)nicotinonitrile to afford the title compound as a white solid (95 mg, 42%). $^1$HNMR (500 MHz, DMSO-d$_6$) δ (ppm) 8.63 (s, 1H), 8.42 (s, 1H), 8.25 (br, 2H), 7.75-7.73 (m, 2H), 7.68 (d, J=8.5 Hz, 2H), 7.45 (d, J=8.5 Hz, 2H), 7.36-7.34 (m, 1H), 7.30-7.26 (m, 2H), 6.65 (br, 1H); MS (ESI) m/z: 407 [M+H]$^+$.

Example 27

5'-((1H-Benzo[d]imidazol-1-yl)(methyl)amino)-2'-cyano-3-(methylthio)-[1,1'-biphenyl]-4-yl sulfamate

Step A. 5-((1H-Benzo[d]imidazol-1-yl)(methyl)amino)-4'-methoxy-3'-(methylthio)-[1,1'-biphenyl]-2-carbonitrile and 5-((1H-benzo[d]imidazol-1-yl)(methyl)amino)-3'-methoxy-4'-(methylthio)-[1,1'-biphenyl]-2-carbonitrile To a mixture of 5-((1H-benzo[d]imidazol-1-yl)amino)-4'-methoxy-3'-(methylthio)-[1,1'-biphenyl]-2-carbonitrile and 5-((1H-benzo[d]imidazol-1-yl)amino)-3'-methoxy-4'-(methylthio)-[1,1'-biphenyl]-2-carbonitrile (860 mg, 2.22 mmol) [see Example 20] in THF (40 mL) was added NaH (501 mg, 3.34 mmol) at 0° C. The mixture was stirred at 0° C. for one hour before a dropwise addition of CH$_3$I (474 mg, 3.34 mmol). After two more hours at 0° C., the reaction mixture was evaporated under reduced pressure. The residue was purified by silica gel column using Petroleum Ether:EtOAc (1:1) as solvents to afford 5-((1H-benzo[d]imidazol-1-yl)(methyl)amino)-4'-methoxy-3'-(methylthio)biphenyl-2-carbonitrile and 5-((1H-benzo[d]imidazol-1-yl)(methyl)amino)-3'-methoxy-4'-(methylthio)biphenyl-2-carbonitrile as a yellow solid (806 mg, 90%). MS (ESI) m/z: 401 [M+H]$^+$.

Step B. 5-((1H-Benzo[d]imidazol-1-yl)(methyl)amino)-4'-hydroxy-3'-(methylthio)-[1,1'-biphenyl]-2-carbonitrile and 5-((1H-benzo[d]imidazol-1-yl)(methyl)amino)-3'-hydroxy-4'-(methylthio)-[1,1'-biphenyl]-2-carbonitrile The procedure describe in Example 18 step D was repeated using a mixture of 5-((1H-benzo[d]imidazol-1-yl)(methyl)amino)-4'-methoxy-3'-(methylthio)biphenyl-2-carbonitrile and 5-((1H-benzo[d] imidazol-1-yl)(methyl)amino)-3'-methoxy-4'-(methylthio)biphenyl-2-carbonitrile to afford the title compounds as 5-((1H-benzo[d]imidazol-1-yl)(methyl)amino)-4'-hydroxy-3'-(methylthio)-[1,1'-biphenyl]-2-carbonitrile as a white solid (200 mg, 25.9%). $^1$H NMR (500 MHz, DMSO-d$_6$) δ (ppm) 10.22 (s, 1H), 8.57 (s, 1H), 7.79-7.77 (d, J=8.9 Hz, 1H), 7.72-7.70 (d, J=8.7 Hz, 1H), 7.37-7.35 (m, 1H), 7.31-7.30 (m, 2H), 7.13-7.11 (m, 2H), 6.88-6.86 (d, J=8.1 Hz, 1H), 6.64 (s, 1H), 6.43-6.41 (d, J=8.7 Hz, 1H), 3.64 (s, 3H), 2.33 (s, 3H); MS (ESI) m/z: 387 [M+H]+ and 5-((1H-benzo[d]imidazol-1-yl)(methyl)amino)-3'-hydroxy-4'-(methylthio)-[1,1'-biphenyl]-2-carbonitrile as a white solid (160 mg, 20.7%). $^1$H NMR (500 MHz, DMSO-d$_6$) δ (ppm) 10.12 (s, 1H), 8.58 (s, 1H), 7.79-7.78 (m, 1H), 7.75-7.73 (d, J=8.7 Hz, 1H), 7.39-7.37 (m, 1H), 7.32-7.29 (m, 2H), 7.18-7.16 (d, J=7.9 Hz, 1H), 6.91-6.89 (m, 2H) 6.58 (s, 1H), 6.51-6.49 (d, J=8.7 Hz, 1H), 3.63 (s, 3H), 2.39 (s, 3H); MS (ESI) m/z: 387 [M+H]$^+$.

Step C. 5'-((1H-Benzo[d]imidazol-1-yl)(methyl)amino)-2'-cyano-3-(methylthio)-[1,1'-biphenyl]-4-yl sulfamate The procedure described in Example 18 step E was repeated using 5-((1H-benzo[d]imidazol-1-yl)(methyl)amino)-4'-hydroxy-3'-(methylthio)-[1,1'-biphenyl]-2-carbonitrile to afford the title compound as a white solid (90 mg, 41%). $^1$H NMR (500 MHz, DMSO-d$_6$) δ (ppm) 8.58 (s, 1H), 8.26 (s, 2H), 7.80-7.77 (m, 2H), 7.48-7.46 (d, J=8.3 Hz, 1H), 7.37-7.36 (m, 2H), 7.34-7.31 (m, 3H), 6.74 (s, 1H), 6.48-6.46 (d, J=8.7, 1H), 3.66 (s, 3H), 2.44 (s, 3H); MS (ESI) m/z: 466 [M+H]$^+$.

Example 28

5'-((1H-Benzo[d]imidazol-1-yl)(methyl)amino)-2'-cyano-4-(methylthio)-[1,1'-biphenyl]-3-yl sulfamate Compound of Example 28 was prepared in the same manner as described for compound of Example 27 starting from 5-((1H-benzo[d]imidazol-1-yl)(methyl)amino)-3'-hydroxy-4'-(methylthio)-[1,1'-biphenyl]-2-carbonitrile. The title compound was obtained as a white solid (80 mg, 47%). $^1$H NMR (500 MHz, DMSO-d$_6$) δ (ppm) 8.58 (s, 1H), 8.22 (s, 2H), 7.80-7.78 (m, 1H), 7.76-7.74 (d, J=8.8 Hz, 1H), 7.52 (s, 1H), 7.46 (s, 2H), 7.38-7.36 (m, 1H), 7.32-7.30 (m, 2H), 6.84 (s, 1H), 6.39-6.37 (d, J=8.8 Hz, 1H), 3.64 (s, 3H), 2.49 (s, 3H); MS (ESI) m/z: 466 [M+H]$^+$.

Example 29

4-(2-((1H-Benzo[d]imidazol-1-yl)(methyl)amino)-5-cyanopyridin-4-yl)phenyl sulfamate Compound of Example 29 was prepared in the same manner as described for compound of Example 16 using 6-(1H-benzo[d]imidazol-1-ylamino)-4-(4-methoxyphenyl)nicotinonitrile to afford the title compound as a white solid (90 mg, 56%). $^1$HNMR (500 MHz, DMSO-d$_6$) δ (ppm) 8.77 (s, 1H), 8.57 (s, 1H), 8.10 (br, 2H), 7.78-7.76 (m, 1H), 7.69 (d, J=8.5 Hz, 2H), 7.41-7.39 (m, 3H), 7.31-7.29 (m, 2H), 6.35 (s, 1H), 3.73 (s, 3H); MS (ESI) m/z: 421 [M+H]$^+$.

Example 30

6-(5-((1H-Benzo[d]imidazol-1-yl)methyl)-2-cyanophenyl)pyridin-3-yl sulfamate

Step A. 2-Bromo-5-((2-(trimethylsilyl)ethoxy)methoxy)pyridine

To a suspension of 6-bromopyridin-3-ol (8.63 g, 49.6 mmol) in CH$_2$Cl$_2$ (130 mL) was added diisopropylethylamine (6.4 g, 49.6 mmol). A clear solution was thus obtained and 2-(trimethylsilyl)ethoxy methyl chloride (8.3 g, 49.6 mmol) was added. After overnight stirring, the mixture was diluted with CH$_2$Cl$_2$ (250 mL) and washed with a saturated aqueous solution of NaHCO$_3$ (150 mL) and brine (150 mL). The organic layer was dried over MgSO$_4$, filtered and concentrated under reduced pressure. The residue was purified by silica gel chromatography using Petroleum Ether:EtOAc (100:1-80:1) as eluting solvents to afford 2-bromo-5-((2-(trimethylsilyl)ethoxy)methoxy)pyridine as a pale yellow oil (13.32 g, 88%). MS (ESI) m/z: 304 [M+H]$^+$.

Step B. 2-(Tributylstannyl)-5-((2-(trimethylsilyl)ethoxy)methoxy)pyridine

A mixture of 2-bromo-5-((2-(trimethylsilyl)ethoxy)methoxy)pyridine (7.74 g, 25.4 mmol), bis(tributyltin) (22.2 g, 38.3 mmol), and Pd(PPh$_3$)$_4$ (2.93 g, 2.54 mmol) in toluene (100 mL) was purged with nitrogen and heated at 120° C. overnight. The reaction mixture was cooled to 23° C. and filtered. The filtrate was concentrated under reduced pressure and the residue was purified by silica gel chromatography using Petroleum Ether:EtOAc (200:1) as eluting solvents to afford 2-(tributylstannyl)-5-((2-(trimethylsilyl)ethoxy)methoxy)pyridine as a yellow oil (1.33 g, 10%). MS (ESI) m/z: 516 [M+H]$^+$.

Step C. 4-((1H-Benzo[d]imidazol-1-yl)methyl)-2-(5-((2-(trimethylsilyl)ethoxy)methoxy)pyridin-2-yl)benzonitrile A mixture of 2-(tributylstannyl)-5-((2-(trimethylsilyl)ethoxy)methoxy)pyridine (1.33 g, 2.59 mmol), 4-((1H-benzo[d]imidazol-1-yl)methyl)-2-bromobenzonitrile (888 mg, 2.84 mmol), and Pd(PPh$_3$)$_4$ (324 mg, 0.28 mmol) in toluene (20 mL) was purged with nitrogen and heated at 120° C. for 48 hours. The reaction mixture was cooled to 23° C. and filtered. The filtrate was concentrated under reduced pressure. The residue was purified by silica gel chromatography using Petroleum Ether:EtOAc (4:1-1:1) as eluting solvents to afford 4-((1H-benzo[d]imidazol-1-yl)methyl)-2-(5-((2-(trimethylsilyl)ethoxy)methoxy)pyridin-2-yl)benzonitrile (830 mg, 70%). MS (ESI) m/z: 457 [M+H]$^+$.

Step D. 4-((1H-Benzo[d]imidazol-1-yl)methyl)-2-(5-hydroxypyridin-2-yl)benzonitrile A mixture of 4-((1H-benzo[d]imidazol-1-yl)methyl)-2-(5-((2-(trimethylsilyl)ethoxy)methoxy)pyridin-2-yl)benzonitrile (680 mg, 1.49 mmol) and tetrabutylammonium fluoride (1.95 g, 7.45 mmol) in tetrahydrofuran (20 mL) was stirred at ambient temperature for 48 hours. The reaction mixture was quenched by adding water (20 mL) and extracted with CH$_2$Cl$_2$ (3×30 mL). The organic extracts were dried over Na$_2$SO$_4$, filtered and concentrated under reduced pressure. The residue was purified by silica gel chromatography using CH$_2$Cl$_2$:CH$_3$OH (15:1) as eluting solvents to afford 4-((1H-benzo[d]imidazol-1-yl)methyl)-2-(5-hydroxypyridin-2-yl)benzonitrile as a solid (140 mg, 29%). MS (ESI) m/z: 327 [M+H]$^+$.

Step E. 6-(5-((1H-Benzo[d]imidazol-1-yl)methyl)-2-cyanophenyl)pyridin-3-yl sulfamate The procedure described in Example 1 Step D was repeated using 4-((1H-benzo[d]imidazol-1-yl)methyl)-2-(5-hydroxypyridin-2-yl)benzonitrile (140 mg, 0.43 mmol) and sulfamoyl chloride (495 mg, 4.3 mmol) to afford the title compound as a white solid (34 mg, 20%). $^1$H NMR (500 MHz, DMSO-d$_6$) δ (ppm) 8.65 (d, 1H), 8.51 (s, 1H), 8.32 (s, 2H), 7.92-7.98 (m, 3H), 7.86 (d, 1H), 7.68 (d, 1H), 7.56 (d, 1H), 7.49 (q, 1H), 7.21-7.23 (m, 2H), 5.70 (s, 2H); MS (ESI) m/z: 406 [M+H]$^+$.

Example 31

4-(5-((1H-Benzo[d]imidazol-1-yl)methyl)-2-cyanopyridin-3-yl)phenyl sulfamate

Step A. (5,6-Dichloropyridin-3-yl)methanol

To a solution of ethyl-5,6-dichloronicotinate (22 g, 100 mmol) in MeOH (220 mL) at 0° C. was added sodium borohydride (18.9 g, 500 mmol) in several small portions. After stirring with at 23° C. for 5 hours, the reaction was quenched by addition of water (100 mL). The mixture was extracted with CH$_2$Cl$_2$ (3×200 mL). The extracts were combined, dried over MgSO$_4$, filtered, and concentrated under reduced pressure. The residue was purified by silica gel chromatography using Petroleum Ether:EtOAc (10:1-6:

1) as eluting solvents to afford (5,6-dichloropyridin-3-yl)methanol as a clear oil (9.7 g, 55%). MS (ESI) m/z: 178 [M+H]+.

Step B. 3-Chloro-5-(hydroxymethyl)picolinonitrile

A mixture of (5,6-dichloropyridin-3-yl)methanol (9.7 g, 54.5 mmol), zinc cyanide (3.52 mg, 30 mmol), and Pd(PPh₃)₄ (6.3 g, 8.18 mmol) in NMP (100 mL) was purged with nitrogen and heated at 100° C. for 48 hours. After cooling to 23° C., water (100 mL) was added. The mixture was extracted with EtOAc (3×150 mL) and the extracts were combined, dried over MgSO₄, filtered and concentrated under reduced pressure. The residue was purified by silica gel chromatography using Petroleum Ether:EtOAc (6:12:1) as eluting solvents to afford 3-chloro-5-(hydroxymethyl)picolinonitrile as a white solid (1.96 g, 21%). MS (ESI) m/z: 169 [M+H]+.

Step C. 5-(Bromomethyl)-3-chloropicolinonitrile

To a solution of 3-chloro-5-(hydroxymethyl)picolinonitrile (1.96 g, 11.63 mmol) in THF (35 mL) was added phosphorus tribromide (4.10 g, 15.11 mmol) in a dropwise manner. After 2 hours stirring at 23° C., the reaction mixture was cooled to 0° C. before the slow addition of a saturated aqueous solution of NaHCO₃ (20 mL). This mixture was extracted with CH₂Cl₂ (3×40 mL), the combined organic solutions were dried over MgSO₄, filtered, and concentrated under reduced pressure. The residue was purified by silica gel chromatography using Petroleum Ether:EtOAc (15:1-10:1) as eluting solvents to afford 5-(bromomethyl)-3-chloropicolinonitrile as a oil (2.01 g, 75%). MS (ESI) m/z: 231 [M+H]+.

Step D. 5-((1H-Benzo[d]imidazol-1-yl)methyl)-3-chloropicolinonitrile

To a solution of 5-(bromomethyl)-3-chloropicolinonitrile (2.01 g, 8.68 mmol) in CH₃CN (20 mL) was added benzimidazole (1.13 g, 9.55 mmol) and K₂CO₃ (2.40, 17.37 mmol). After stirring at 40° C. for 2 hours, the mixture was cooled and filtered. The filtrate was concentrated under reduced pressure.
The residue was purified by silica gel chromatography to afford 5-((1H-benzo[d]imidazol-1-yl)methyl)-3-chloropicolinonitrile as a white solid (1.2 g, 51%). MS (ESI) m/z: 269 [M+H]+.

Step E. 5-((1H-Benzo[d]imidazol-1-yl)methyl)-3-(4-(benzyloxy)phenyl)picolinonitrile The procedure described in Example 1 step C was repeated using 5-((1H-benzo[d]imidazol-1-yl)methyl)-3-chloropicolinonitrile (402 mg, 1.50 mmol) and 4-(benzyloxy)phenylboronic acid (513 mg, 2.25 mmol), the title compound was obtained as a solid (680 mg, 80%). MS (ESI) m/z: 417 [M+H]+.

Step F. 5-((1H-Benzo[d]imidazol-1-yl)methyl)-3-(4-hydroxyphenyl)picolinonitrile

To a solution of Pd(OAc)₂ (75 mg, 0.32 mmol) and triethylsilane (4.5 mL) in CH₂Cl₂ (10 mL) was added triethylamine (2.2 mL). After the mixture was stirred at ambient temperature for 15 minutes, a solution of 5-((1H-benzo[d]imidazol-1-yl)methyl)-3-(4-(benzyloxy)phenyl)picolinonitrile (600 mg, 1.28 mmol) in CH₂Cl₂ (15 mL) was added. The reaction mixture was stirred for 4 hours, filtered and concentrated under reduced pressure. The residue was purified by silica gel chromatography to afford 5-((1H-benzo[d]imidazol-1-yl)methyl)-3-(4-hydroxyphenyl)-picolinonitrile as a solid (115 mg, 22%). MS (ESI) m/z: 327 [M+H]+.

Step G. 4-(5-((1H-Benzo[d]imidazol-1-yl)methyl)-2-cyanopyridin-3-yl)phenyl sulfamate The procedure described in Example 1 step E was repeated using 5-((1H-benzo[d]imidazol-1-yl)methyl)-3-(4-hydroxyphenyl)picolinonitrile (115 mg, 0.35 mmol) and sulfamoyl chloride (407 mg, 3.5 mmol), the title compound was obtained as a white solid (81 mg, 57%). ¹H NMR (500 MHz, DMSO-d₆) δ (ppm) 8.80 (d, 1H), 8.50 (s, 1H), 8.17 (s, 2H), 8.06 (d, 1H), 7.64-7.73 (m, 4H), 7.45-7.47 (m, 2H), 7.20-7.26 (m, 2H), 5.72 (s, 2H); MS (ESI) m/z: 406 [M+H]+.

Example 32

4-(6-(1H-Benzo[d]imidazol-1-ylamino)-3-cyanopyrazin-2-yl)phenyl sulfamate

Step A. 6-Chloro-5-iodopyrazin-2-amine

To a solution of 6-chloropyrazin-2-amine (10 g, 77.2 mmol) in DMSO (100 mL) was added NIS (17.4 g, 77.2 mmol) and the solution was stirred at 25° C. overnight. After the mixture was poured into water and extracted with EtOAc, the organic solutions were collected, washed with brine, dried over NaSO₄ and filtered. The filtrate was evaporated under reduced pressure and the residue purified by silica gel chromatograph using Petroleum Ether:EtOAc 1:4 as eluting solvents to afford 6-chloro-5-iodopyrazin-2-amine as a yellow solid (17.2 g, 88%). MS (ESI) m/z: 255 [M+H]+.

Step B. 5-Amino-3-chloropyrazine-2-carbonitrile

A mixture of 6-chloro-5-iodopyrazin-2-amine (17.2 g, 67.7 mmol), Zn(CN)₂ (4.35 g, 37.2 mmol) and Pd(PPh₃)₄ (3.9 g, 3.4 mmol) in NMP was heated at 100° C. for 14 hours. The reaction mixture was concentrated under reduced pressure and the residue was purified by silica gel chromatography using Petroleum Ether:EtOAc 1:4 as eluting solvents to afford 5-amino-3-chloropyrazine-2-carbonitrile as a yellow solid (9.4 g, 90%). MS (ESI) m/z: 155 [M+H]+.

Step C. 5-Amino-3-(4-(benzyloxy)phenyl)pyrazine-2-carbonitrile

The procedure described in Example 1 step C was repeated using 5-amino-3-chloropyrazine-2-carbonitrile (6 g, 39 mmol) and 4-(benzyloxy)phenylboronic acid (9.3 g, 41 mmol) to afford the title compound as a yellow solid (10 g, 85%). MS (ESI) m/z: 303 [M+H]+.

Step D. 3-(4-(Benzyloxy)phenyl)-5-bromopyrazine-2-carbonitrile

A mixture of CuBr₂ (8 g, 35.7 mmol), t-butylnitrite (4.6 g, 45 mmol) in CH₃CN (100 mL) was heated at 60° C. for 5 minutes before addition of 5-amino-3-(4-(benzyloxy)phenyl)pyrazine-2-carbonitrile (9 g, 29.7 mmol). The reaction mixture was stirred for another 10 minutes before pouring into a 2.0 N aqueous solution of HCl (100 mL). After extraction with EtOAc and washing with a 2.0 N aqueous solution of HCl, the organic solution was dried over sodium sulfate, filtered and concentrated under reduced pressure to afford 3-(4-(benzyloxy)phenyl)-5-bromopyrazine-2-carbonitrile as a yellow solid (5.8 g, 45%). MS (ESI) m/z: 367 [M+H]+.

Step E. 5-(1H-Benzo[d]imidazol-1-ylamino)-3-(4-(benzyloxy)phenyl)pyrazine-2-carbonitrile The procedure described in Example 2 step B was repeated using 3-(4-(benzyloxy)phenyl)-5-bromopyrazine-2-carbonitrile (2.5 g, 6.8 mmol) to afford the title compound as a yellow solid (1 g, 35%). MS (ESI) m/z: 419 [M+H]+.

Step F. 5-(1H-Benzo[d]imidazol-1-ylamino)-3-(4-hydroxyphenyl)pyrazine-2-carbonitrile A solution of 5-(1H-benzo[d]imidazol-1-ylamino)-3-(4-(benzyloxy)phenyl) pyrazine-2-carbonitrile (500 mg, 1.37 mmol) in $CF_3CO_2H$ (10 mL) was heated at 90° C. for 10 hours. The reaction mixture was concentrated under reduced pressure. The residue was purified by silica gel chromatography using Petroleum Ether:EtOAc 1:1 as eluting solvents to afford 5-(1H-benzo[d]imidazol-1-ylamino)-3-(4-hydroxyphenyl)pyrazine-2-carbonitrile as a white solid (150 mg, 38%). MS (ESI) m/z: 329 [M+H]+.

Step G. 4-(6-(1H-Benzo[d]imidazol-1-ylamino)-3-cyanopyrazin-2-yl)phenyl sulfamate The procedure described in Example 1 step E was repeated using 5-(1H-benzo[d]imidazol-1-ylamino)-3-(4-hydroxyphenyl)pyrazine-2-carbonitrile (150 mg, 0.46 mmol) to afford the title compound as a yellow solid (30 mg, 16%). $^1H$ NMR (500 MHz, DMSO-$d_6$) δ (ppm) 11.70 (s, 1H), 8.46 (s, 1H), 8.22 (br, 1H), 8.11 (s, 2H), 7.74 (d, J=7.2 Hz, 1H), 7.70 (m, 2H), 7.46 (d, J=5.6 Hz, 1H), 7.36 (d, J=8.2 Hz, 2H), 7.29 (m, 2H); MS (ESI) m/z: 408 [M+H]+.

Example 33

6-(5-((3H-Imidazo[4,5-b]pyridin-3-yl)methyl)-2-cyanophenyl)pyridin-3-yl sulfamate Step A. 4-((3H-Imidazo[4,5-b]pyridin-3-yl)methyl)-2-(5-((2-(trimethylsilyl)ethoxy) methoxy)pyridin-2-yl)benzonitrile The procedure described in Example 30 step C was repeated using 2-(tributylstannyl)-5-((2-(trimethylsilyl)ethoxy)methoxy)pyridine (800 mg, 1.52 mmol) and 4-((3H-imidazo[4,5-b]pyridin-3-yl)methyl)-2-bromobenzonitrile (400 mg, 1.38 mmol) [Example 12 step A] to afford the title compound as a brown solid (560 mg, 89%). MS (ESI) m/z: 458 [M+H]+.

Step B. 4-((3H-Imidazo[4,5-b]pyridin-3-yl)methyl)-2-(5-hydroxypyridin-2-yl)benzonitrile To a solution of 4-((3H-imidazo[4,5-b]pyridin-3-yl)methyl)-2-(5-((2-(trimethylsilyl)ethoxy) methoxy)pyridin-2-yl)benzonitrile (300 mg, 0.656 mmol) in $CH_2Cl_2$ (50 mL) at 0° C. was added $CF_3CO_2H$ (0.5 mL). The mixture was stirred at room temperature for 4 hours. After evaporation under reduced pressure, the residue was purified by preparative HPLC to afford 4-((3H-imidazo[4,5-b]pyridin-3-yl)methyl)-2-(5-hydroxypyridin-2-yl)benzonitrile as a white solid (97 mg, 45%). MS (ESI) m/z: 328 [M+H]+.

Step C. 6-(5-((3H-Imidazo[4,5-b]pyridin-3-yl)methyl)-2-cyanophenyl)pyridin-3-yl sulfamate The procedure described in Example 1 step E was repeated using 4-((3H-imidazo[4,5-b]pyridin-3-yl)methyl)-2-(5-hydroxypyridin-2-yl)benzonitrile (90 mg) and sulfamoyl chloride, the title compound was obtained as yellow solid (55 mg, 49%). $^1H$ NMR (500 MHz, DMSO-$d_6$) δ (ppm) 8.68 (s, 1H), 8.65 (d, J=2.5 Hz, 1H), 8.36 (d, J=5.0 Hz, 1H), 8.33 (s, 2H), 8.12 (d, J=8.0 Hz, 1H), 7.92-7.97 (m, 3H), 7.87 (s, 1H), 7.53 (d, J=8.0 Hz, 1H), 7.30 (t, J=8.0 Hz, 1H), 5.69 (s, 2H); MS (ESI) m/z: 407 [M+H]+.

Example 34

4-(6-((1H-Benzo[d]imidazol-1-yl)(methyl)amino)-3-cyanopyrazin-2-yl)phenyl sulfamate Step A. 5-((1H-Benzo[d]imidazol-1-yl)(methyl)amino)-3-(4-(benzyloxy)phenyl)pyrazine-2-carbonitrile The procedure described in Example 5 step A was repeated using 5-(1H-benzo[d]imidazol-1-ylamino)-3-(4-(benzyloxy)phenyl)pyrazine-2-carbonitrile (2 g, 4.8 mmol) to afford the title compound as a yellow solid (1.86 g, 90%). MS (ESI) m/z: 433 [M+H]+.

Step B. 5-((1H-Benzo[d]imidazol-1-yl)(methyl)amino)-3-(4-hydroxyphenyl)pyrazine-2-carbonitrile The procedure described in Example 32 step F was repeated using 5-((1H-benzo[d]imidazol-1-yl)(methyl)amino)-3-(4-(benzyloxy)phenyl)pyrazine-2-carbonitrile (1.6 g, 3.68 mmol) to afford the title compound as a white solid (400 mg, 31.5%). MS (ESI) m/z: 343 [M+H]+.

Step C. 4-(6-((1H-Benzo[d]imidazol-1-yl)(methyl)amino)-3-cyanopyrazin-2-yl)phenyl sulfamate The procedure described in Example 1 step E was repeated using 5-((1H-benzo[d]imidazol-1-yl)(methyl)amino)-3-(4-hydroxyphenyl)pyrazine-2-carbonitrile (350 mg, 1.02 mmol) to afford the title compound as a white solid (67 mg, 15.6%). $^1H$ NMR (500 MHz, DMSO-$d_6$) δ (ppm) 8.62 (s, 1H), 8.18 (s, 2H), 7.93 (s, 2H), 8.38 (m, 1H), 7.52 (m, 1H), 7.46 (d, J=8.5 Hz, 2H), 7.35 (m, 2H), 3.77 (s, 3H); MS (ESI) m/z: 422 [M+H]+.

Example 35

5'-(3H-[1,2,3]Triazolo[4,5-b]pyridin-3-ylamino)-2'-cyano-[1,1'-biphenyl]-4-yl sulfamate Step A. 2-Hydrazinyl-3-nitropyridine To a solution of 2-chloro-3-nitropyridine (50 g, 316 mmol) in acetonitrile (500 mL) at 0° C. was added hydrazine hydrate (28 g, 474 mmol) and stirred at 20° C. for 20 hours. The reaction mixture was concentrated under reduced pressure to afford 2-hydrazinyl-3-nitropyridine as a yellow solid (48 g, 100%). MS (ESI) m/z: 155.1 [M+H]+.

Step B. tert-Butyl 2-(3-nitropyridin-2-yl)hydrazinecarboxylate

To a solution of 2-hydrazinyl-3-nitropyridine (48 g, 316 mmol) and $K_2CO_3$ (129 g, 948 mmol) in 1,4-dioxane (500 ml) at 0° C. was added neat di-tert-butyl dicarbonate (71 g, 327 mmol) in a dropwise manner. The mixture was stirred at room temperature for 12 hours before filtration and concentration under reduced pressure. The residue was purified by silica gel chromatography using Petroleum Ether:EtOAc (5:1-3:1) as eluting solvents to afford tert-butyl 2-(3-nitropyridin-2-yl)hydrazinecarboxylate as a yellow solid (49 g, 50%). MS (ESI) m/z: 255.1 [M+H]$^+$.

Step C. tert-Butyl 2-(3-aminopyridin-2-yl)hydrazinecarboxylate

To a solution of tert-butyl 2-(3-nitropyridin-2-yl)hydrazinecarboxylate (49 g, 193 mmol) in MeOH (500 ml) was added 10% Pd/C (2 g). The mixture was stirred under hydrogen atmosphere at room temperature for 12 hours. The reaction mixture was filtered and concentrated under reduced pressure to afford tert-butyl 2-(3-aminopyridin-2-yl)hydrazinecarboxylate as a brown solid (40 g, 93%). MS (ESI) m/z: 225.2 [M+H]$^+$.

Step D. tert-Butyl 3H-[1,2,3]triazolo[4,5-b]pyridin-3-ylcarbamate

To a solution of tert-butyl 2-(3-aminopyridin-2-yl)hydrazinecarboxylate (40 g, 179 mmol) and acetic acid (50 mL) in THF 400 (mL) at 0° C. was added neat tert-butyl nitrite (28 g, 269 mmol) dropwise. The reaction mixture was stirred at 20° C. for 8 hours and then quenched by addition of an aqueous solution of $NaHCO_3$ (10%, 200 mL). After extraction with EtOAc (200 mL), the organic solution was dried over $MgSO_4$, filtered, and concentrated under reduced pressure. The residue was purified by silica gel chromatography using Petroleum Ether:EtOAc (5:1-2:1) as eluting solvents to afford tert-butyl 3H-[1,2,3]triazolo[4,5-b]pyridin-3-ylcarbamate as a brownish solid (30 g, 73%). MS (ESI) m/z: 236.1 [M+H]$^+$.

Step E. 3H-[1,2,3]Triazolo[4,5-b]pyridin-3-amine

To a solution of tert-butyl 3H-imidazo[4,5-b]pyridin-3-ylcarbamate (30 g, 128 mmol) in $CH_2Cl_2$ (300 ml) at 0° C. was added trifluoroacetic acid (60 mL) dropwise. The resulting mixture was stirred at 23° C. for 4 hours before concentration under reduced pressure. An aqueous solution of $NaHCO_3$ (10%, 300 mL) was added to the residue which was extracted with EtOAc (300 mL). The extract was dried over $MgSO_4$, filtered and concentrated under reduced pressure. The residue was purified by silica gel chromatography using Petroleum Ether:EtOAc (3:1-0:1) as eluting solvents to afford 3H-[1,2,3]triazolo [4,5-b]pyridin-3-amine as a yellow solid (12 g, 70%). MS (ESI) m/z: 136.1 [M+H]$^+$.

Step F. 5'-(3H-[1,2,3]Triazolo[4,5-b]pyridin-3-ylamino)-2'-cyano-[1,1'-biphenyl]-4-yl sulfamate The procedures described in Example 2 steps B, C, D and were repeated using 3H-[1,2,3]triazolo [4,5-b]pyridin-3-amine and 2-bromo-4-fluorobenzonitrile to afford the title compound as a white solid (110 mg). $^1$H NMR (500 MHz, DMSO-$d_6$) δ (ppm) 11.21 (s, 1H), 8.80 (dd, J=1.0 Hz and 4.5 Hz, 1H), 8.71 (dd, J=1.5 Hz and 10.0 Hz, 1H), 8.11 (s, 2H), 7.76 (d, J=8.0 Hz, 1H), 7.62-7.60 (m, 1H), 7.57 (d, J=8.5 Hz, 1H), 7.38 (d, J=8.5 Hz, 1H), 6.67 (d, J=2.0 Hz, 2H), 6.54 (dd, J=2.0 and 8.5 Hz, 2H); MS (ESI) m/z: 408.0 [M+H]$^+$.

Example 36

4-(2-((3H-Imidazo[4,5-b]pyridin-3-yl)methyl)-5-cyanopyridin-4-yl)phenyl sulfamate

Step A. 4-Chloro-6-methylnicotinonitrile

A solution of 4-hydroxy-6-methylnicotinamide (15 g, 92.6 mmol) in $POCl_3$ (50 mL) was heated at 110° C. for 12 hours. After evaporation of the excess of $POCl_3$ under reduced pressure, the residue was poured into ice-water and its pH was adjusted to about 8 with a saturated aqueous solution of $Na_2CO_3$. The mixture was extracted with EtOAc (150 mL×3). The combined organic layer was dried over $Na_2SO_4$, filtered and concentrated under reduced pressure. The crude product was purified by silica gel chromatography using Petroleum Ether:EtOAc (100:1-10:1) as eluting solvents to afford 4-chloro-6-methylnicotinonitrile as a white solid (8.5 g, 61%). MS (ESI) m/z: 153 [M+H]$^+$.

Step B. 6-(Bromomethyl)-4-chloronicotinonitrile

To a solution of 4-chloro-6-methylnicotinonitrile (7.0 g, 46 mmol) in $CCl_4$ (50 mL) was added NBS (9.0 g, 50.6 mmol) and benzoyl peroxide (5.5 g, 23 mmol). The mixture was heated at 110° C. for 12 hours before cooling down to 25° C. and filtration of the precipitate. The filtrate was concentrated under reduced pressure. The residue was purified by silica gel chromatography using Petroleum Ether:EtOAc (100:1) as eluting solvents to afford 6-(bromomethyl)-4-chloronicotinonitrile as a brown oil (4.0 g, 38%). MS (ESI) m/z: 231 [M+H]$^+$.

Step C. 6-((3H-Imidazo[4,5-b]pyridin-3-yl)methyl)-4-chloronicotinonitrile

The procedure described in Example 1 step B was repeated using 6-(bromomethyl)-4-chloronicotinonitrile (1.6 g, 4.8 mmol) and 3H-imidazo[4,5-b]pyridine (0.58 g, 4.8 mmol) to afford the title compound as yellow solid (160 mg, 13%). MS (ESI) m/z: 270 [M+H]$^+$.

Step D. 4-(2-((3H-Imidazo[4,5-b]pyridin-3-yl)methyl)-5-cyanopyridin-4-yl)phenyl sulfamate The procedures described in Example 2 steps C, D and E were repeated using 6-((3H-imidazo[4,5-b]pyridin-3-yl)methyl)-4-chloronicotinonitrile to afford the title compound as a yellow solid (90 mg, 36%). $^1$H NMR (500 MHz, DMSO-$d_6$) δ (ppm) 9.00 (s, 1H), 8.61 (s, 1H), 8.31 (d, J=5.0 Hz, 1H), 8.19 (s, 2H), 8.11 (d, J=7.0 Hz, 1H), 7.78 (d, J=8.5 Hz, 2H), 7.72 (s, 1H), 7.49 (d, J=8.5 Hz, 2H), 7.28 (t, J=8.0 Hz, 1H); 5.80 (s, 2H); MS (ESI) m/z: 407 [M+H]$^+$.

Example 37

6-(5-((1H-Benzo[d]imidazol-1-yl)(methyl)amino)-2-cyanophenyl)pyridin-3-yl sulfamate

Step A. 4-((1H-Benzo[d]imidazol-1-yl)(methyl)amino)-2-bromobenzonitrile

The procedure described in Example 5 step A was repeated using 4-((1H-benzo[d]imidazol-1-yl)(methyl)

amino)-2-bromobenzonitrile (1.8 g, 5.75 mmol) and MeI (1.22 g, 8.62 mmol) to afford the title compound as a white solid (1.83 g, 97%). MS (ESI) m/z: 327 [M+H]+.

Step B. 6-(5-((1H-Benzo[d]imidazol-1-yl)(methyl) amino)-2-cyanophenyl)pyridin-3-yl sulfamate The procedures described in Example 33 steps A, B and C were repeated using 4-((1H-benzo[d]imidazol-1-yl) (methyl)amino)-2-bromobenzonitrile to afford the title compound as a brown solid (85 mg, 49%). $^1$H NMR (500 MHz, DMSO-d$_6$) δ (ppm) 8.62 (t, 2H), 8.31 (s, 2H), 7.88-7.93 (m, 2H), 7.79-7.82 (m, 2H), 7.38 (q, 1H), 7.30-7.34 (m, 2H), 6.97 (d, 1H), 6.60 (q, 1H), 3.65 (s, 3H); MS (ESI) m/z: 421 [M+H]+.

Example 38

4-(5-(1H-Benzo[d]imidazol-1-ylamino)-2-cyanopyridin-3-yl)phenyl sulfamate

Step A.
3-(4-(Benzyloxy)phenyl)-5-chloropyridin-2-amine

A mixture of 3-bromo-5-chloropyridin-2-amine (10.0 g, 48.2 mmol), 2-(4-(benzyloxy)phenyl)-4,4,5,5-tetramethyl-1,3-dioxaborolane (17.94 g, 57.8 mmol), Pd(PPh$_3$)$_4$ (2.78 g, 2.41 mmol), and K$_2$CO$_3$ (13.32 g, 96.4 mmol) in toluene (80 mL), EtOH (20 mL), and H$_2$O (10 mL) was purged with nitrogen and heated at 85° C. overnight. The reaction mixture was cooled to 25° C., diluted by EtOAc (200 mL), and filtered. The filtrate was concentrated under reduced pressure. The residue was purified by crystallization in EtOAc to afford 3-(4-(benzyloxy)phenyl)-5-chloropyridin-2-amine as a white solid (12.71 g, 85%). MS (ESI) m/z: 311 [M+H]+.

Step B.
3-(4-(Benzyloxy)phenyl)-5-chloro-2-fluoropyridine

To a solution of 3-(4-(benzyloxy)phenyl)-5-chloropyridin-2-amine (12.71 g, 40.9 mmol), Olah's reagent (100 mL) (J. Fluorine Chemistry 1986, 33, 377) at −20° C. was added NaNO$_2$ (5.65 g, 81.8 mmol) in small portions. After the addition of NaNO$_2$, the solution was allowed to warm to 23° C. slowly and stirred for 2 hours. The reaction mixture was neutralized to pH=7 by adding a saturated aqueous solution of NaHCO$_3$ and extracted with EtOAc (3×100 mL). The combined EtOAc layers were dried over Na$_2$SO4, filtered, concentrated under reduced pressure and purified by silica gel chromatography using Petroleum Ether and EtOAc as eluting solvents to afford 3-(4-(benzyloxy)phenyl)-5-chloro-2-fluoropyridine as a white solid (12.24 g, 94%). MS (ESI) m/z: 314 [M+H].

Step C.
3-(4-(Benzyloxy)phenyl)-5-chloropicolinonitrile

A solution of 3-(4-(benzyloxy)phenyl)-5-chloro-2-fluoropyridine (12.24 g, 39.01 mmol), KCN (12.70 g, 195.06 mmol) in NMP (100 mL) was stirred at 115° C. overnight. The solution was cooled to room temperature and concentrated under reduced pressure. The residue was purified by silica gel chromatography using Petroleum Ether and EtOAc as eluting solvents to afford 3-(4-(benzyloxy)phenyl)-5-chloropicolinonitrile as a white solid (5.10 g, 41%). MS (ESI) m/z: 321 [M+H]+.

Step D. 5-(1H-Benzo[d]imidazol-1-ylamino)-3-(4-(benzyloxy)phenyl)picolinonitrile The procedure described in Example 2 step B was repeated using 3-(4-(benzyloxy)phenyl)-5-chloropicolinonitrile (2.0 g, 6.24 mmol) to afford the title compound as a white solid (1.40 g, 54%). MS (ESI) m/z: 418 [M+H]+.

Step E. 5-(1H-Benzo[d]imidazol-1-ylamino)-3-(4-hydroxyphenyl)picolinonitrile

A solution of 5-(1H-benzo[d]imidazol-1-ylamino)-3-(4-(benzyloxy)phenyl)picolinonitrile (500 mg, 1.2 mmol), 10% Pd—C (50 mg), pyridine (1 mL), and MeOH (10 mL) under hydrogen atmosphere was stirred at room temperature for 2 hours. The solution was filtered, the filtrate was concentrated under reduced pressure to afford 5-(1H-benzo[d]imidazol-1-ylamino)-3-(4-hydroxyphenyl)picolinonitrile as a white solid (360 mg, 92%), which was without further purification. MS (ESI) m/z: 328 [M+H]+.

Step F. 4-(5-(1H-Benzo[d]imidazol-1-ylamino)-2-cyanopyridin-3-yl)phenyl sulfamate The procedure described in Example 1 step E was repeated using 5-(1H-benzo[d]imidazol-1-ylamino)-3-(4-hydroxyphenyl)picolinonitrile (495 mg, 4.28 mmol), the title compound was obtained as a white solid (200 mg, 57%). $^1$H NMR (500 MHz, DMSO-d$_6$) δ (ppm) 10.70 (s, 1H), 8.49 (s, 1H), 8.11 (s, 3H), 7.76 (d, J=9.0 Hz, 1H), 7.59 (d, J=9.0 Hz, 2H), 7.39 (m, 3H), 7.30 (m, 2H), 6.70 (s, 1H); MS (ESI) m/z: 407 [M+H]+.

Example 39

4-(5-((1H-Benzo[d]imidazol-1-yl)(methyl)amino)-2-cyanopyridin-3-yl)phenyl sulfamate Step A. 5-((1H-Benzo[d]imidazol-1-yl)(methyl) amino)-3-(4-(benzyloxy)phenyl)-picolinonitrile The procedure described in Example 5 step A was repeated using 5-(1H-benzo[d]imidazol-1-ylamino)-3-(4-(benzyloxy)phenyl)picolinonitrile (550 mg, 1.32 mmol) [Example 38 step D] to afford the title compound as a yellow solid (568 mg, 100%). MS (ESI) m/z: 432 [M+H]+.

Step B. 4-(5-((1H-Benzo[d]imidazol-1-yl)(methyl) amino)-2-cyanopyridin-3-yl)phenyl sulfamate The procedures described in Example 38 steps E and F were repeated using 5-((1H-Benzo[d]imidazol-1-yl) (methyl)amino)-3-(4-(benzyloxy)phenyl)picolinonitrile to afford the title compound as a white solid (160 mg, 43%). $^1$H NMR (500 MHz, DMSO-d$_6$) δ (ppm) 8.60 (s, 1H), 8.14 (s, 2H), 7.90 (d, J=2.5 Hz, 1H), 7.79 (d, J=9.0 Hz, 1H), 7.67 (d, J=8.0 Hz, 2H), 7.43 (m, 3H), 7.32 (m, 2H), 7.06 (d, J=2.5 Hz, 1H), 3.68 (s, 3H); MS (ESI) m/z: 421 [M+H]+.

Example 40

4-(6-(3H-Imidazo[4,5-b]pyridin-3-ylamino)-3-cyanopyrazin-2-yl)phenyl sulfamate

Step A. tert-Butyl 3H-imidazo[4,5-b]pyridin-3-ylcarbamate

A solution of tert-butyl 2-(3-aminopyridin-2-yl)hydrazinecarboxylate (40 g, 178 mmol) [Example 35 step C] in triethyl orthoformate (200 mL) was stirred at 130° C. for 3 hours. Then the reaction mixture was concentrated under reduced pressure and the residue purified by silica gel chromatography using Petroleum Ether:EtOAc (1:0-3:1) as eluting solvents to afford tert-butyl 3H-imidazo[4,5-b]pyridin-3-ylcarbamate as a white solid (30 g, 72%). MS (ESI) m/z: 235.1 [M+H]$^+$.

Step B. 3H-Imidazo[4,5-b]pyridin-3-amine

To a solution of tert-butyl 3H-imidazo[4,5-b]pyridin-3-ylcarbamate (30 g, 128 mmol) in CH$_2$Cl$_2$ (300 ml) at 0° C. was added trifluoroacetic acid (60 mL) dropwise. The resulting mixture was stirred at room temperature for 4 hours before concentration under reduced pressure. An aqueous solution of NaHCO$_3$ (10%, 300 mL) was added to the residue which was extracted with EtOAc (300 mL). The extract was dried over Na$_2$SO$_4$, filtered and concentrated under reduced pressure. The residue was purified by silica gel chromatography using Petroleum Ether:EtOAc (3:1-0:1) as eluting solvents to afford 3H-imidazo[4,5-b]pyridin-3-amine as a yellow solid (12 g, 70%). MS (ESI) m/z: 135.1 [M+H]$^+$.

Step C. 4-(6-(3H-Imidazo[4,5-b]pyridin-3-ylamino)-3-cyanopyrazin-2-yl)phenyl sulfamate The procedures described in Example 32 steps E, F and G were repeated using 3-(4-(benzyloxy)phenyl)-5-bromopyrazine-2-carbonitrile and 3H-imidazo[4,5-b]pyridin-3-amine to afford the title compound as a white solid (80 mg, 64%). $^1$H NMR (500 MHz, DMSO-d$_6$) δ (ppm) 11.80 (s, 1H), 8.70 (s, 1H), 8.36 (d, J=4.3 Hz, 1H), 8.21 (d, J=8.1 Hz, 1H), 8.12 (s, 2H), 7.66 (s, 2H), 7.37 (m, 3H); MS (ESI) m/z: 409 [M+H]$^+$.

Example 41

6-(5-(1H-Benzo[d]imidazol-1-ylamino)-2-cyanophenyl)pyridin-3-yl sulfamate

The procedures described in Example 33 steps A, B and C were repeated using 4-(1H-benzo[d]imidazol-1-ylamino)-2-bromobenzonitrile (757 mg, 2.42 mmol) [Example 2 step B] and 2-(tributylstannyl)-5-((2-(trimethylsilyl)ethoxy)methoxy)pyridine (1.24 g, 2.42 mmol) [Example 30 Step B] to afford the title compound as a brown solid (31 mg, 5%). $^1$H NMR (500 MHz, DMSO-d$_6$) δ (ppm) 10.44 (s, 1H), 8.60 (d, 1H), 8.49 (s, 1H), 7.85-7.87 (m, 2H), 7.75-7.80 (m, 2H), 7.28-7.34 (m, 3H), 6.86 (s, 1H), 6.60 (d, 1H); MS (ESI) m/z: 407 [M+H]$^+$.

Example 42

6'-((1H-Benzo[d]imidazol-1-yl)methyl)-3'-cyano-[2,2'-bipyridin]-5-yl sulfamate

Step A. 6-((1H-Benzo[d]imidazol-1-yl)methyl)-5'-((2-(trimethylsilyl)ethoxy) methyoxy)-2,2'-bipyridine-3-carbonitrile A mixture of 6-((1H-benzo[d]imidazol-1-yl)methyl)-2-chloronicotinonitrile (1.2 g, 4.5 mmol) [see Example 10 Step B], 2-(tributylstannyl)-5-((2-(trimethylsilyl)ethoxy)methoxy)pyridine (2.3 g, 4.5 mmol) [Example 30 Step B], Pd(PPh$_3$)$_4$ (260 mg, 0.225 mmol), LiCl (381 mg, 9 mmol), and CuI (171 mg, 0.9 mmol) in toluene (10 mL) was purged with nitrogen and heated at 120° C. overnight.

The reaction mixture was cooled to 23° C. and filtered. The filtrate was concentrated under reduced pressure and purified by silica gel chromatography using Petroleum Ether:EtOAc (10:1~1:1) as eluting solvents to afford 6-((1H-benzo[d]imidazol-1-yl)methyl)-5'-((2-(trimethylsilyl)ethoxy)-methyoxy)-2,2'-bipyridine-3-carbonitrile as a brown solid (600 mg, 29%). MS (ESI) m/z: 458 [M+H]$^+$.

Step B. 6-((1H-Benzo[d]imidazol-1-yl)methyl)-5'-hydroxy-2,2'-bipyridine-3-carbonitrile To a solution of 6-((1H-benzo[d]imidazol-1-yl)methyl)-5'-((2-(trimethylsilyl)ethoxy)-methoxy)2,2'-bipyridine-3-carbonitrile (654 mg, 2 mmol) in CH$_2$Cl$_2$ (40 mL) at room temperature was added CF$_3$CO$_2$H (2 mL). The mixture was stirred at 20° C. for 2 hours before evaporation of the solvent under reduced pressure. The residue was purified by preparative HPLC to afford 6-((1H-benzo[d]imidazol-1-yl)methyl)-5'-hydroxy-2,2'-bipyridine-3-carbonitrile as a white solid (350 mg, 82%). MS (ESI) m/z: 328 [M+H]$^+$.

Step C. 6'-((1H-Benzo[d]imidazol-1-yl)methyl)-3'-cyano-[2,2'-bipyridin]-5-yl sulfamate The procedure described in Example 1 step E was repeated using 6-((1H-benzo[d]imidazol-1-yl)methyl)-5'-hydroxy-2,2'-bipyridine-3-carbonitrile (350 mg, 1.07 mmol) and sulfamoyl chloride to afford the title compound as a white solid (281 mg, 65%). $^1$H NMR (500 MHz, DMSO-d$_6$) δ ppm 8.63 (d, J=2.0 Hz, 1H), 8.57 (s, 1H), 8.45 (d, J=8.0 Hz, 1H), 8.34 (s, 2H), 8.09 (d, J=9.0 Hz, 1H), 7.92 (dd, J=2.5 Hz and J=8.5 Hz, 1H), 7.71 (d, J=8.5 Hz, 1H), 7.60 (d, J=7.5 Hz, 1H), 7.55 (d, J=8.0 Hz, 1H), 7.26 (m, 2H), 5.84 (s, 2H); MS (ESI) m/z: 406 [M+H]$^+$.

Example 43

4-(5-(3H-Imidazo[4,5-b]pyridin-3-ylamino)-2-cyanopyridin-3-yl)phenyl sulfamate

Compound of Example 43 was prepared in the same manner as described for compound of Example 38 starting from 3-(4-(benzyloxy)phenyl)-5-chloropicolinonitrile and 3H-imidazo[4,5-b]pyridin-3-amine [see Example 40 Step A-E]. The title compound was obtained as a white solid (74 mg, 45%). $^1$H NMR (500 MHz, DMSO-d$_6$) δ (ppm) 8.70 (s, 1H), 8.36 (m, 1H), 8.21 (dd, J=8.0 Hz, 1H), 8.14 (d, J=2.5 Hz, 1H), 7.61 (d, J=8.0 Hz, 2H), 7.38 (m, 3H), 6.87 (d, J=2.5 Hz, 1H); MS (ESI) m/z: 408 [M+H]$^+$.

Example 44

4-(6-((3H-Imidazo[4,5-b]pyridin-3-yl)(methyl)amino)-3-cyanopyrazin-2-yl)phenyl sulfamate Compound of Example 44 was prepared in the same manner as described for compound of Example 34 starting from 5-(3H-imidazo[4,5-b]pyridin-3-ylamino)-3-(4-(benzyloxy)phenyl)pyrazine-2-carbonitrile. The title compound was obtained as a white solid (110 mg, 25.6%). $^1$H NMR (500 MHz, DMSO-d$_6$) δ (ppm) 8.83 (s, 1H), 8.38 (d, J=4.7 Hz, 1H), 8.27 (d, J=8.0 Hz, 1H), 8.18 (s, 2H), 7.92 (s, 2H), 7.44 (m, 3H), 3.80 (s, 3H); MS (ESI) m/z: 423 [M+H]$^+$.

Example 45

4-(5-((3H-Imidazo[4,5-b]pyridin-3-yl)(methyl)amino)-2-cyanopyridin-3-yl)phenyl sulfamate Compound of Example 45 was prepared in the same manner as described for compound of Example 39 starting from 5-(3H-imidazo[4,5-b]pyridin-3-ylamino)-3-(4-(benzyloxy)phenyl)picolinonitrile. The title compound was obtained as a white solid (46 mg, 25%). $^1$H NMR (500 MHz, DMSO-$d_6$) δ (ppm) 8.81 (s, 1H), 8.36 (d, J=4.5 Hz, 1H), 8.24 (d, J=7.5 Hz, 1H), 8.13 (s, 2H), 7.95 (d, J=2.5 Hz, 1H), 7.71 (d, J=8.5 Hz, 2H), 7.42 (m, 3H), 7.22 (d, J=2.5 Hz, 1H), 3.69 (s, 3H); MS (ESI) m/z: 422 [M+H]$^+$.

Example 46

4-(6-(3H-Imidazo[4,5-b]pyridin-3-ylamino)-3-cyanopyridin-2-yl)phenyl sulfamate

Step A. 6-(3H-imidazo[4,5-b]pyridin-3-ylamino)-2-(4-methoxyphenyl)nicotinonitrile A mixture of 6-chloro-2-(4-methoxyphenyl)nicotinonitrile (3.0 g, 12.3 mmol), tert-butyl 3H-imidazo[4,5-b]pyridin-3-yl carbamate (2.88 g, 12.3 mmol) [see Example 40 Step A-D], Pd$_2$(dba)$_3$ (563 mg, 0.615 mmol), xantphos (711 mg, 1.23 mmol), and Cs$_2$CO$_3$ (10.0 g, 30.75 mmol) in toluene (15 mL) in a sealed vial was purged with nitrogen and heated at 110° C. for 12 hours. The reaction mixture was cooled and purified by silica gel chromatography using Petroleum Ether:EtOAc (1:2-1:1) as eluting solvents to afford 6-(3H-imidazo[4,5-b]pyridin-3-ylamino)-2-(4-methoxy phenyl)nicotinonitrile (2 g, 47.6%). MS (ESI) m/z: 343 [M+H]$^+$.

Step B. 4-(6-(3H-Imidazo[4,5-b]pyridin-3-ylamino)-3-cyanopyridin-2-yl)phenyl sulfamate The procedures described in Example 2 steps D and E were repeated using 6-(3H-imidazo[4,5-b]pyridin-3-ylamino)-2-(4-methoxy phenyl)nicotinonitrile to afford the title compound as a white solid (256 mg, 31%). $^1$H NMR (500 MHz, DMSO-$d_6$) δ (ppm): 11.19 (s, 1H), 8.69 (s, 1H), 8.34 (dd, J=1.5 Hz, J=5.0 Hz, 1H), 8.20-8.11 (m, 5H), 7.64 (s, 2H), 7.35 (m, 3H); MS (ESI) m/z: 408 [M+H]$^+$.

Example 47

4-(2-(3H-Imidazo[4,5-b]pyridin-3-ylamino)-5-cyanopyrimidin-4-yl)phenyl sulfamate

Step A. 2-(3H-Imidazo[4,5-b]pyridin-3-ylamino)-4-(4-methoxyphenyl)pyrimidine-5-carbonitrile A mixture of 2-chloro-4-(4-methoxyphenyl) pyrimidine-5-carbonitrile (3.0 g, 12.2 mmol) [Example 10 Step C], tert-butyl 3H-imidazo[4,5-b]pyridin-3-yl carbamate (2.9 mg, 12.2 mmol) [see Example 40 Step A-D], Cs$_2$CO$_3$ (9.9 g, 30.5 mmol), Pd$_2$(dba)$_3$ (558 mg, 0.61 mmol), and xantphos (1.80 mmol, 1.22 mmol) in 1,4-dioxane (15 mL) in a sealed vial was purged with nitrogen and heated at 110° C. for 12 hours. The reaction mixture was cooled and purified by silica gel chromatography using Petroleum Ether:EtOAc (1:1-1:2) as eluting solvents to afford 2-(3H-imidazo[4,5-b]pyridin-3-ylamino)-4-(4-methoxyphenyl)pyrimidine-5-carbonitrile (3.00 g, 71%). MS (ESI) m/z: 343 [M+H]$^+$.

Step B. 4-(2-(3H-Imidazo[4,5-b]pyridin-3-ylamino)-5-cyanopyrimidin-4-yl)phenyl sulfamate The procedures described in Example 2 steps D and E were repeated using 2-(3H-imidazo[4,5-b]pyridin-3-ylamino)-4-(4-methoxyphenyl)pyrimidine-5-carbonitrile to afford the title compound as a white solid (123 mg, 13%). $^1$H NMR (500 MHz, DMSO-$d_6$) δ (ppm): 11.87 (s, 1H), 813-8.68 (m, 2H), 8.36-8.09 (m, 5H), 7.60 (d, J=7.5 Hz, 1H), 7.55 (d, J=8.0 Hz, 1H), 7.37 (s, 1H), 7.32 (d, J=8.0 Hz, 1H); MS (ESI) m/z: 409 [M+H]$^+$.

Example 48

4-(2-((3H-Imidazo[4,5-b]pyridin-3-yl)(methyl)amino)-5-cyanopyrimidin-4-yl)phenyl sulfamate Compound of Example 48 was prepared in the same manner as described for compound of Example 5 starting from 2-(3H-imidazo[4,5-b]pyridin-3-ylamino)-4-(4-methoxyphenyl)pyrimidine-5-carbonitrile [see Example 47 Step A]. The title compound was obtained as a white solid (315 mg, 27%). $^1$H NMR (500 MHz, DMSO-$d_6$) δ (ppm): 9.22-9.77 (m, 2H), 8.36 (d, J=3.5 Hz, 1H), 8.25-8.12 (m, 4H), 7.55 (s, 2H), 7.39 (m, 1H), 7.30 (s, 1H), 3.88 (s, 3H); MS (ESI) m/z: 423 [M+H]$^+$.

Example 49

4-(6-((3H-Imidazo[4,5-b]pyridin-3-yl)(methyl)amino)-3-cyanopyridin-2-yl)phenyl sulfamate Compound of Example 49 was prepared in the same manner as described for compound of Example 5 starting from 6-(3H-imidazo[4,5-b]pyridin-3-ylamino)-2-(4-methoxyphenyl)nicotinonitrile [see Example 46 Step A]. The title compound was obtained as a white solid (177 mg, 24%). $^1$H NMR (500 MHz, DMSO-$d_6$) δ (ppm): 8.82 (s, 1H), 8.37 (dd, J=1.5 Hz and 4.5 Hz, 1H), 8.25 (dd, J=1.0 Hz and 8.0 Hz, 1H), 8.17 (s, 2H), 8.08 (d, J=9.0 Hz, 1H), 7.87 (s, 2H), 7.43-7.40 (m, 3H); 6.41 (s, 1H), 3.77 (s, 3H). MS (ESI) m/z: 422 [M+H]$^+$.

Example 50

4-(5-((3H-imidazo[4,5-b]pyridin-3-yl)methyl)-2-cyanopyridin-3-yl)phenyl sulfamate Compound of Example 50 was prepared in the same manner as described for compound of Example 31 starting from 3H-imidazo[4,5-b]pyridine. The title compound was obtained as a white solid (252 mg, 58%). $^1$H NMR (500 MHz, DMSO-$d_6$) δ (ppm) 8.83 (d, 1H), 8.69 (s, 1H), 8.38 (q, 1H), 8.18 (s, 2H), 8.10-8.13 (m, 2H), 7.73 (q, 2H), 7.46 (q, 2H), 7.31 (q, 1H), 5.73 (s, 2H); MS (ESI) m/z: 407 [M+H]$^+$.

Example 51

4-(2-Cyano-5-((5,6-difluoro-1H-benzo[d]imidazol-1-yl)methyl)pyridin-3-yl)phenyl sulfamate Compound of Example 51 was prepared in the same manner as described for compound of Example 31 starting from 5,6-difluoro-1H-benzo[d]imidazole. The title compound was obtained as a brown solid (213 mg, 65%). $^1$H NMR (500 MHz, DMSO-d$_6$) δ (ppm) 8.83 (d, 1H), 8.63 (s, 1H), 8.19 (s, 2H), 8.11 (d, 1H), 7.94 (q, 1H), 7.73-7.78 (m, 3H), 7.48 (d, 2H), 5.70 (s, 2H); MS (ESI) m/z: 442 [M+H]$^+$.

Example 52

4-(5-Cyano-2-((5,6-difluoro-1H-benzo[d]imidazol-1-yl)methyl)pyrimidin-4-yl)phenyl sulfamate Compound of Example 52 was prepared in the same manner as described for compound of Example 9 starting from 5,6-difluoro-1H-benzo[d]imidazole. The title compound was obtained as a white solid (148 mg, 10%). $^1$H NMR (500 MHz, DMSO-d$_6$) δ (ppm) 9.33 (s, 1H), 8.45 (s, 1H), 8.23 (s, 2H), 7.99 (d, J=9.0 Hz, 2H), 7.76 (t, J=8.8 Hz, 2H), 7.50 (dd, J=7.0 Hz, 2H), 5.95 (s, 2H); MS (ESI) m/z: 443 [M+H]$^+$.

Pharmacologic Study of the Compounds of the Present Invention

1—Aromatase and Steroid Sulfatase Inhibition

Aromatase and steroid sulfatase enzymes inhibitions were evaluated in the human chorionic carcinoma cell line JEG-3 which constitutively expresses high amount of aromatase and steroid sulfatase.

For aromatase inhibition assay, JEG-3 cells were seeded into 96-well plates at 35,000 cells/well and maintained in MEM containing supplements. When reaching 80% confluent, the cells were washed once with serum-free MEM, incubated with [1β-$^3$H] androstenedione (A4, 0.2 μCi/ml) for 1.25 hour in the presence of the test substances added in a concentration series. The product, tritiated water ($^3$H$_2$O), was separated using 2.5% (w/v) dextran-coated charcoal at 4-8° C. for 2 hours. The supernatant radioactivity was measured by a MicroBeta scintillation counter.

For STS assay, JEG-3 cells were seeded into 24-well culture plates at 150,000 cells/ml/well and maintained in MEM containing supplements overnight. When reaching 80% confluent, the cells were washed once with serum-free MEM, loaded with 1 ml of substrate mix containing [6,7-3H] Estrone sulfate (E1S, 0.6 μCi/ml) and [4-14C] Estrone (E1, 4 nCi/ml) in the presence of compounds in a concentration series, and incubated for 1 hour at 37° C. The product [3H]E1 was separated from E1S by toluene partition using [4-14C]E1 to monitor extraction procedural losses, and the toluene fraction radioactivity was measured by a MicroBeta scintillation counter.

Experiments are performed in duplicate. The inhibitory concentration of 50% of the enzymatic activity is calculated. Results for some examples are shown in the Table 1 below.

TABLE 1

| Example | Aromatase Inhibition IC50 (nM) | Steroid Sulfatase Inhibition IC50 (nM) |
|---|---|---|
| 1 | 1.2 | 2.0 |
| 2 | 2.0 | 6.8 |
| 3 | * | 18.9 |
| 4 | 4.8 | 12.1 |
| 5 | 3.2 | 25.6 |
| 6 | 53.2 | * |
| 7 | * | 16.4 |
| 8 | 6.3 | 23.6 |
| 9 | 3.5 | 1.8 |
| 10 | 3.2 | 9.1 |
| 11 | 1.2 | 18.4 |
| 12 | 0.5 | 7.0 |
| 13 | 13.1 | * |

TABLE 1-continued

| Example | Aromatase Inhibition IC50 (nM) | Steroid Sulfatase Inhibition IC50 (nM) |
|---|---|---|
| 14 | 7.0 | 21.7 |
| 15 | 17.5 | 14.6 |
| 16 | 6.4 | 22.0 |
| 17 | 2.2 | 3.9 |
| 18 | 1.2 | 26.4 |
| 19 | 2.2 | * |
| 20 | 2.9 | 52.3 |
| 21 | 2.2 | * |
| 22 | 3.7 | 6.0 |
| 23 | 6.5 | 7.1 |
| 24 | 0.9 | 2.0 |
| 25 | 6.2 | 10.7 |
| 26 | 2.7 | 11.8 |
| 27 | 4.6 | 17.8 |
| 28 | 5.8 | * |
| 29 | 2.5 | 37.6 |
| 30 | 5.9 | 7.2 |
| 31 | 4.6 | 10.5 |
| 32 | 37.6 | 19.5 |
| 33 | 9.0 | 17.6 |
| 34 | 8.4 | 35.7 |
| 35 | 5.1 | 29.4 |
| 36 | 2.0 | 10.5 |
| 37 | 2.4 | 41.8 |
| 38 | 2.7 | 19.1 |
| 39 | 1.5 | * |
| 40 | * | 18.8 |
| 41 | 2.0 | 9.3 |
| 42 | 41.9 | * |
| 43 | 11.8 | * |
| 44 | 5.8 | * |
| 45 | 2.1 | * |
| 46 | 21.7 | 39.5 |
| 47 | 56.1 | 44.1 |
| 48 | 5.8 | * |
| 49 | 3.7 | * |
| 50 | 16.3 | * |
| 51 | 2.2 | 15.5 |
| 52 | 2.9 | 5.4 |

*IC$_{50}$ > 60 nM

2—Cytochrome P450 Inhibition

Inhibitory activity of the compounds towards CYP1A2, 2C9, 2C19, 2D6, and 3A4 was evaluated using human recombinant CYPs.

Test compounds and reference inhibitors were initially prepared from their stock solutions in a mixture solvent of DMSO/ACN (10/90) at a concentration of 200-fold of the final. A 3-fold serial dilution (1/3, 1/9, 1/27 etc.) was made in the DMSO/ACN mixture solvent to generate 7 consecutive concentrations. The serially diluted solutions of test compounds and reference inhibitors (positive controls) were further diluted directly in recombinant human CYP enzymes in assay buffer (0.1 M potassium phosphate buffer, pH7.4) to reach the concentration of 2-fold of the final (2×).

Aliquots of 30 μL of 2× compound/enzyme solutions were loaded to a 96-well assay plates and preincubated at 37° C. for 10 minutes. An aliquot of 15 μL of prewarmed 4× substrate solutions made in the assay buffer was added into each of the wells containing the 2× compound/enzyme mixtures. Finally, the reaction was initiated by adding an aliquot of 15 μL of 4×NADPH made in the assay buffer and the assay plates were further incubated at 37° C. for a time period designated for each isoform (5 minutes for 3A4, 20 minutes for 2C9, 10 minutes for 2D6 and 2C19, and 15 minutes for 1A2). The reactions were stopped by adding 120 μL ACN containing the stable isotopes of the metabolites for corresponding CYP isoforms, followed by vortexing for 5 minutes and centrifugation at 4000 rpm for 15 minutes. The resulting supernatants were transferred into new 96-well plates for LC-MS/MS analysis.

Experiments are performed in duplicate. The inhibitory concentration of 50% of the enzymatic activity is calculated. Results for some examples are shown in the Table 2 below.

TABLE 2

| Example | CYP1A2 IC50 (μM) | CYP2C9 IC50 (μM) | CYP2C19 IC50 (μM) | CYP2D6 IC50 (μM) | CYP3A4 IC50 (μM) |
|---|---|---|---|---|---|
| 9  | >5 | >5 | >5 | >5 | 3.68 |
| 17 | >5 | >5 | >5 | >5 | >5 |
| 22 | >5 | >5 | >5 | >5 | >5 |
| 24 | >5 | >5 | >5 | >5 | 3.26 |
| 26 | >5 | >5 | >5 | >5 | 2.54 |
| 31 | >5 | >5 | >5 | >5 | >5 |
| 36 | >5 | >5 | >5 | >5 | >5 |

The invention claimed is:

1. A compound of the formula (Ia)

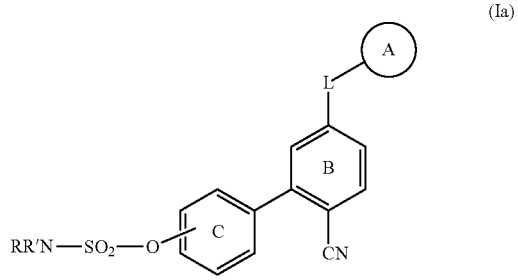

(Ia)

wherein
- A represents an aromatic bicyclic ring of up to 10 ring members, containing at least two nitrogen atoms as ring member, and being optionally substituted by one or more substituents selected from halo, alkyl and haloalkyl;
- B represents an aromatic monocyclic ring of 6 ring members, containing optionally nitrogen atoms as ring member;
- C represents an aromatic monocyclic ring of 6 ring members, containing optionally nitrogen atoms as ring member and optionally substituted by an alkyl-sulfonyle, the radical RR'N—SO2—O being in meta or para position;
- R and R' represent, independently, hydrogen or alkyl;
- L is a linker selected from —CH2-, —NH—, —N(alkyl)- and —N(cycloalkyl-methyl)-; or any pharmaceutically acceptable salt thereof.

2. A compound according to claim 1, of the formula (I)

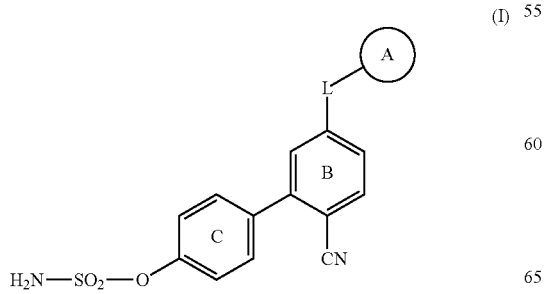

(I)

wherein
- A represents an aromatic bicyclic ring of up to 10 ring members, containing at least two nitrogen atoms as ring member, and being optionally substituted by one or more substituents selected from halo;
- B represents an aromatic monocyclic ring of 6 ring members, containing optionally nitrogen atoms as ring member;
- C represents an aromatic monocyclic ring of 6 ring members, containing optionally nitrogen atoms as ring member;
- L is a linker selected from —CH2-, —NH— and —N(Me)-; or any pharmaceutically acceptable salt thereof.

3. A compound according to claim 1, wherein L is a linker selected from —CH2- and —NH—; or any pharmaceutically acceptable salt thereof.

4. A compound according to claim 1, wherein A represents an aromatic bicyclic ring of 9 ring members, containing at least two nitrogen atoms as ring member, and being optionally substituted by one or more substituents selected from halo; or any pharmaceutically acceptable salt thereof.

5. A compound according to claim 1, wherein A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members; or any pharmaceutically acceptable salt thereof.

6. A compound according to claim 1, wherein A represents an aromatic bicyclic ring of 9 ring members, containing from two to four nitrogen atoms as ring member, and being optionally substituted by one or more substituents selected from halo, the bicyclic ring being the fusion of a ring of 5 ring members and a ring of 6 ring members, the ring of 5 ring members containing at least 2 nitrogen atoms and being linked to the linker L; or any pharmaceutically acceptable salt thereof.

7. A compound according to claim 1, wherein A represents an aromatic bicyclic ring selected from

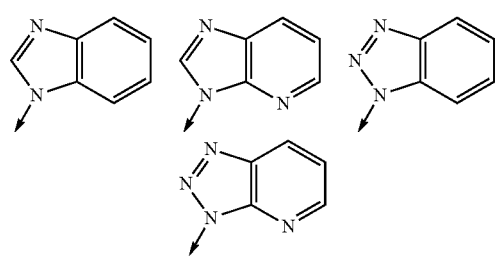

and being optionally substituted by one or more substituents selected from halo; or any pharmaceutically acceptable salt thereof.

8. A compound according to claim 1, wherein A represents a unsubstituted ring; or any pharmaceutically acceptable salt thereof.

9. A compound according to claim 1, wherein the B ring contains at least one nitrogen atom as ring member; or any pharmaceutically acceptable salt thereof.

10. A compound according to claim 1, wherein the B ring contains from one or two nitrogen atoms as ring member; or any pharmaceutically acceptable salt thereof.

11. A compound according to claim 1, wherein B represents an aromatic monocyclic ring selected from

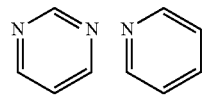

or any pharmaceutically acceptable salt thereof.

12. A compound according to claim 1, wherein the C ring contains no nitrogen atom as ring member; or any pharmaceutically acceptable salt thereof.

13. A compound according to claim 1, wherein C represents an aromatic monocyclic ring containing one nitrogen atoms as ring member; or any pharmaceutically acceptable salt thereof.

14. A compound according to claim 1, wherein the B and C rings contain no nitrogen atom as ring member; or any pharmaceutically acceptable salt thereof.

15. A compound according to claim 1, wherein at least one of the B and C rings contains at least one nitrogen atom as ring member; or any pharmaceutically acceptable salt thereof.

16. A pharmaceutical composition containing, as active ingredient, at least one compound of the general formula according to claim 1, in association with a pharmaceutically acceptable support.

* * * * *